United States Patent
Xu et al.

(10) Patent No.: US 12,365,686 B2
(45) Date of Patent: Jul. 22, 2025

(54) COMPOUND AS PORCUPINE INHIBITOR AND USE THEREOF

(71) Applicant: JIANGSU KANION PHARMACEUTICAL CO., LTD., Lianyungang (CN)

(72) Inventors: Xiongbin Xu, Shanghai (CN); Yi Chen, Shanghai (CN); Cailin Wang, Shanghai (CN); Ru Feng, Shanghai (CN); Wen Jiang, Shanghai (CN); Lingyun Wu, Shanghai (CN); Jian Li, Shanghai (CN); Shuhui Chen, Shanghai (CN)

(73) Assignee: JIANGSU KANION PHARMACEUTICAL CO., LTD., Lianyungang (CN)

( * ) Notice: Subject to any disclaimer, the term of this patent is extended or adjusted under 35 U.S.C. 154(b) by 823 days.

(21) Appl. No.: 17/626,001

(22) PCT Filed: Jul. 8, 2020

(86) PCT No.: PCT/CN2020/100771
§ 371 (c)(1),
(2) Date: Jan. 10, 2022

(87) PCT Pub. No.: WO2021/004467
PCT Pub. Date: Jan. 14, 2021

(65) Prior Publication Data
US 2022/0281873 A1    Sep. 8, 2022

(30) Foreign Application Priority Data
Jul. 8, 2019  (CN) .................. 201910613678.X

(51) Int. Cl.
*C07D 487/04* (2006.01)
*A61P 35/00* (2006.01)
(52) U.S. Cl.
CPC ............ *C07D 487/04* (2013.01); *A61P 35/00* (2018.01)

(58) Field of Classification Search
CPC ............................... C07D 487/04; A61P 35/00
See application file for complete search history.

(56) References Cited

U.S. PATENT DOCUMENTS

2007/0105864 A1* 5/2007 Guzi ................ A61K 31/498
514/249

OTHER PUBLICATIONS

Ali et al., "Input of Isosteric and Bioisosteric Approach in Drug Design" J.Chem. Soc. Pak., vol. 36, No. 1, 2014 (Year: 2014).*

* cited by examiner

*Primary Examiner* — Danah Al-Awadi
*Assistant Examiner* — Donna M Nestor
(74) *Attorney, Agent, or Firm* — Mintz Levin Cohn Ferris Glovsky and Popeo, P.C.

(57) ABSTRACT

Disclosed is a class of porcupine inhibitors, specifically a compound as represented by formula (I), and a pharmaceutically acceptable salt or an isomer thereof.

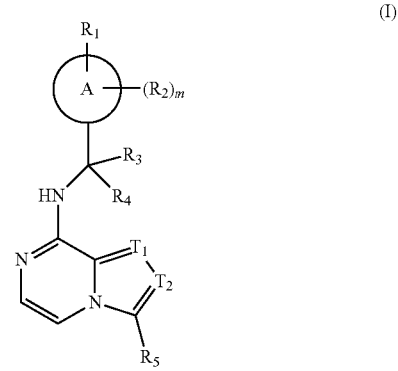

16 Claims, No Drawings

COMPOUND AS PORCUPINE INHIBITOR AND USE THEREOF

The present application is a United States National Phase under 35 U.S.C. § 371 of International Application No. PCT/CN2020/100771, filed Jul. 8, 2020, which claims the priority of: Application No. CN201910613678.X, filed on Jul. 8, 2019.

FIELD OF THE INVENTION

The present disclosure relates to a class of porcupine inhibitors, in particular, to a compound represented by formula (I), a pharmaceutically acceptable salt or an isomer thereof.

BACKGROUND OF THE INVENTION

Wnt/β-Catenin signaling pathway is crucial for embryonic development and adult homeostasis. The Wnt/β-Catenin pathway regulates the protein network composition of the following three processes: 1. Production and secretion of WNT protein; 2. WNT protein binds to Frz and LRP5/6 on the cell surface to form a trimer, which transmits the signal and activates Dishevelled proteins Dsh or Dvl in the cytoplasm; after signaling, the stability of the degradation complex composed of (3-catenin, axin, glycogen synthase kinase-3β (GSK-3β), and colorectal adenomatous polyposis coli (APC) gene can be weakened, and phosphorylation-dependent degradation of β-catenin can be prevented, so that the concentration of β-catenin in the cytoplasm is increased. 3. β-catenin then transfers into the nucleus and interacts with T cell transcription factor/lymphoid enhancer factor TCF/LEF, thereby activating the Wnt/β-catenin signaling pathway, and ultimately activating the expression of downstream target genes.

Porcupine (PORCN) protein is an acyltransferase that activates the extracellular secretion of Wnt protein through palmitoylation of WNT protein. The extracellular Wnt protein binds to the Frizzled receptor on the cell membrane to activate the Wnt/β-Catenin pathway, so that the β-Catenin accumulates and enters the nucleus, and binds to the TCF/LEF transcription factor in the nucleus, thereby regulating downstream target gene transcription, and promoting tumor cell proliferation and activation.

Many tumors (including gastric cancer, colorectal cancer, liver cancer and pancreatic cancer, etc.) have excessive activated WNT/β-Catenin signaling pathway. Porcupine inhibitors inhibit the activity of Porcupine protein, and block the palmitoylation and extracellular secretion of Wnt protein, thereby inhibiting the abnormal activation of Wnt/β-Catenin signaling pathway, and in turn inhibiting the proliferation of a variety of tumor cells. At present, porcupine inhibitors entering clinical trials include LGK974 (the patent application for this compound is WO2010101849) and ETC-1922159 (the patent application for this compound is WO2014189466). These clinically researched porcupine inhibitors have problems such as fast metabolism, short half-life, and greater side effects. In view of this, the development of new porcupine inhibitors to regulate Wnt/β-Catenin pathway signaling has important clinical value and social significance.

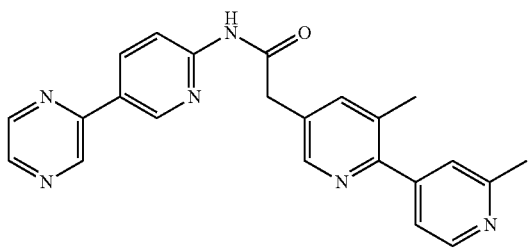

LGK974

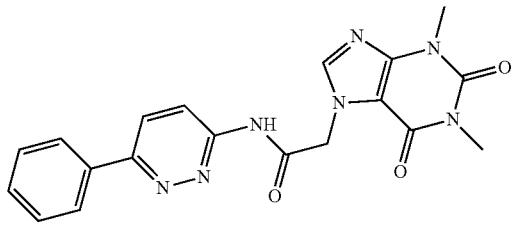

ETC-1922159

SUMMARY OF THE INVENTION

In one aspect, provided is a compound of formula (I), a pharmaceutically acceptable salt thereof or an isomer thereof,

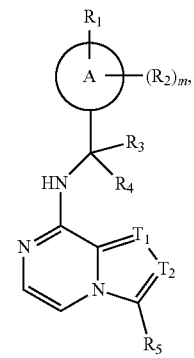

(I)

wherein $T_1$ and $T_2$ are each independently CH or N;

ring A is $C_{6-10}$ aryl, 5- to 6-membered heteroaryl, 5- to 6-membered heterocycloalkyl or $C_{5-6}$ cycloalkyl;

$R_1$ is pyrazolyl or 6-membered heteroaryl, wherein the pyrazolyl and 6-membered heteroaryl are optionally substituted with 1, 2 or 3 $R_a$;

each $R_a$ is independently H, F, Cl, Br, I, CN, —OH, —OCH$_3$ or $C_{1-3}$ alkyl, wherein the $C_{1-3}$ alkyl is optionally substituted with 1, 2 or 3 substituents independently selected from F, Cl, Br, I, —OH or —CN;

each $R_2$ is independently H, F, Cl, Br, I, CN, —OH,

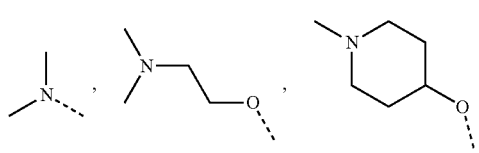

or $C_{1-3}$ alkyl, wherein the $C_{1-3}$ alkyl is optionally substituted with 1, 2 or 3 substituents independently selected from F, Cl, Br, I, —OH or —CN;

$R_3$ and $R_4$ are each independently H or $C_{1-3}$ alkyl, wherein the $C_{1-3}$ alkyl is optionally substituted with 1 or 2 substituents independently selected from F, Cl, Br, I or —OH;

$R_5$ is —C(=O)—$NR_bR_c$, $C_{6-10}$ aryl, 5- to 6-membered heteroaryl, 5- to 6-membered heterocycloalkyl or $C_{3-6}$ cycloalkyl, wherein the $C_{6-10}$ aryl, 5- to 6-membered heteroaryl, 5- to 6-membered heterocycloalkyl and $C_{3-6}$ cycloalkyl are optionally substituted with 1, 2 or 3 $R_d$;

each $R_d$ is independently H, F, Cl, Br, I, CN, —C(=O)—$C_{1-3}$ alkyl, $C_{1-3}$ alkyl or $C_{1-3}$ alkoxy, wherein the $C_{1-3}$ alkyl and $C_{1-3}$ alkoxy are optionally substituted with 1, 2 or 3 substituents independently selected from F, Cl, Br, I, —OH or —CN;

m is 0, 1, 2 or 3;

$R_b$ and $R_c$ are each independently H, $C_{1-6}$ alkyl or phenyl, or $R_b$ and $R_c$ together with the N atom to which they are attached form 5- to 6-membered heteroaryl or 5- to 6-membered heterocycloalkyl, wherein the $C_{1-6}$ alkyl, phenyl, 5- to 6-membered heteroaryl and 5- to 6-membered heterocyclyl are optionally substituted with 1, 2 or 3 R;

each R is independently F, Cl, Br, I, CN, —OH or $C_{1-3}$ alkyl, wherein the $C_{1-3}$ alkyl is optionally substituted with 1, 2 or 3 substituents independently selected from F, Cl, Br, I, —OH or —CN;

the 5- to 6-membered heteroaryl and 5- to 6-membered heterocycloalkyl contain 1, 2, 3 or 4 heteroatoms independently selected from N, —O— and —S—.

The present disclosure also provides a compound of formula (I), a pharmaceutically acceptable salt thereof or an isomer thereof,

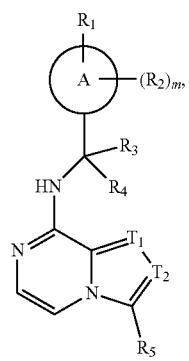
(I)

wherein $T_1$ and $T_2$ are each independently CH or N;

ring A is $C_{6-10}$ aryl, 5- to 6-membered heteroaryl, 5- to 6-membered heterocycloalkyl or $C_{5-6}$ cycloalkyl;

$R_1$ is 6-membered heteroaryl, wherein the 6-membered heteroaryl is optionally substituted with 1, 2 or 3 $R_a$;

each $R_a$ is independently H, F, Cl, Br, I, CN, —OH or $C_{1-3}$ alkyl, wherein the $C_{1-3}$ alkyl is optionally substituted with 1, 2 or 3 substituents independently selected from F, Cl, Br, I, —OH or —CN;

each $R_2$ is independently H, F, Cl, Br, I, CN, —OH or $C_{1-3}$ alkyl, wherein the $C_{1-3}$ alkyl is optionally substituted with 1, 2 or 3 substituents independently selected from F, Cl, Br, I, —OH or —CN;

$R_3$ and $R_4$ are each independently H or $C_{1-3}$ alkyl;

$R_5$ is —C(=O)—$NR_bR_c$, $C_{6-10}$ aryl, 5- to 6-membered heteroaryl, 5- to 6-membered heterocycloalkyl or $C_{3-6}$ cycloalkyl, wherein the $C_{6-10}$ aryl, 5- to 6-membered heteroaryl, 5- to 6-membered heterocycloalkyl and $C_{3-6}$ cycloalkyl are optionally substituted with 1, 2 or 3 $R_d$;

each $R_d$ is independently H, F, Cl, Br, I, CN, —C(=O)—$C_{1-3}$ alkyl, $C_{1-3}$ alkyl or $C_{1-3}$ alkoxy, wherein the $C_{1-3}$ alkyl or $C_{1-3}$ alkoxy are optionally substituted with 1, 2 or 3 substituents independently selected from F, Cl, Br, I, —OH or —CN;

m is 0, 1, 2 or 3;

$R_b$ and $R_c$ are each independently H or $C_{1-6}$ alkyl, or $R_b$ and $R_c$ together with the N atom to which they are attached form 5- to 6-membered heteroaryl or 5- to 6-membered heterocycloalkyl, wherein the $C_{1-6}$ alkyl, 5- to 6-membered heteroaryl and 5- to 6-membered heterocyclyl are optionally substituted with 1, 2 or 3 R;

each R is independently F, Cl, Br, I, CN, —OH or $C_{1-3}$ alkyl, wherein the $C_{1-3}$ alkyl is optionally substituted with 1, 2 or 3 substituents independently selected from F, Cl, Br, I, —OH or —CN;

the 5- to 6-membered heteroaryl and 5- to 6-membered heterocycloalkyl contain 1, 2, 3 or 4 heteroatoms independently selected from N, —O— and —S—.

In some embodiments of the present disclosure, the above compound has a structure as shown in formula (I-1) or (I-2):

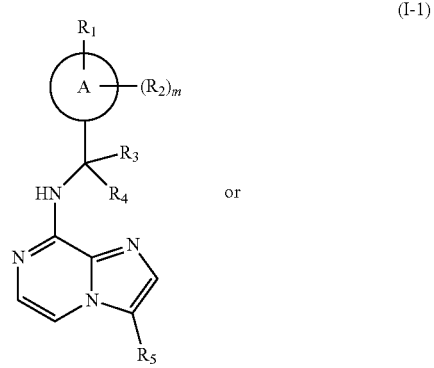
(I-1)

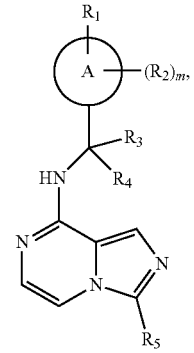
(I-2)

wherein ring A, $R_1$, $R_2$, $R_3$, $R_4$, $R_5$ and m are as defined herein.

In some embodiments of the present disclosure, the $T_1$ is N, $T_2$ is CH, and other variables are as defined herein.

In some embodiments of the present disclosure, the ring A is phenyl, pyridyl, piperidinyl or cyclohexyl, and other variables are as defined herein.

In some embodiments of the present disclosure, the moiety

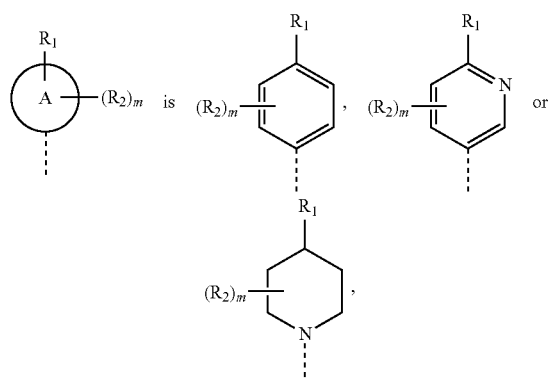

and $R_1$, $R_2$ and m and other variables are as defined herein.

In some embodiments of the present disclosure, the moiety

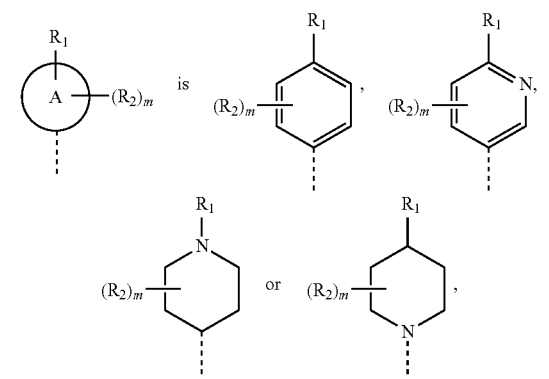

and $R_1$, $R_2$ and m and other variables are as defined herein.

In some embodiments of the present disclosure, the moiety

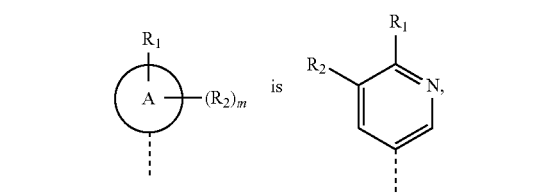

and $R_1$ and $R_2$ and other variables are as defined herein.

In some embodiments of the present disclosure, the moiety

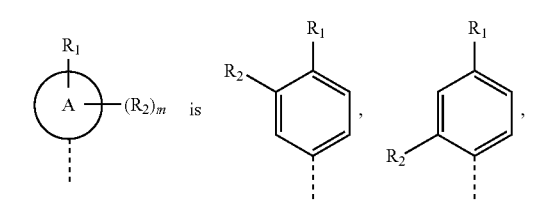

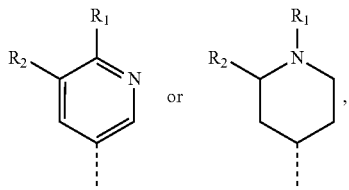

and $R_1$ and $R_2$ and other variables are as defined herein.

In some embodiments of the present disclosure, the moiety

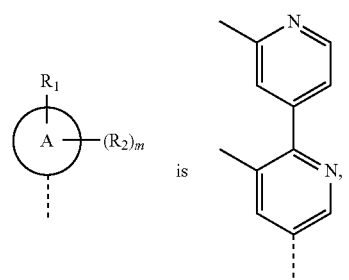

and other variables are as defined herein.

In some embodiments of the present disclosure, the moiety

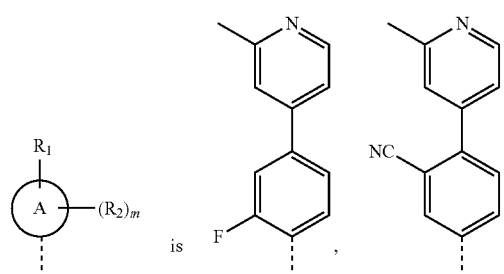

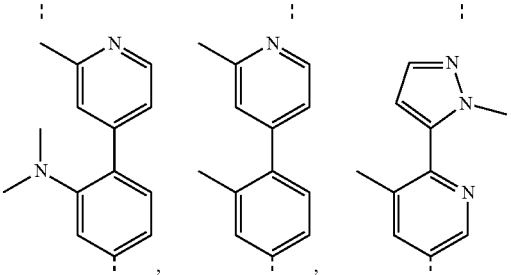

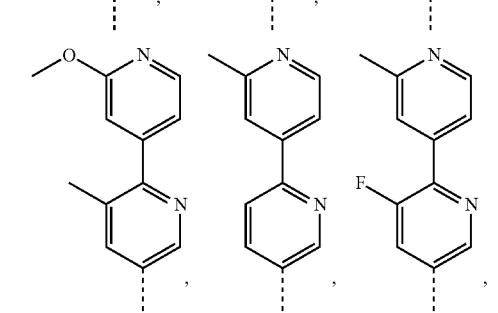

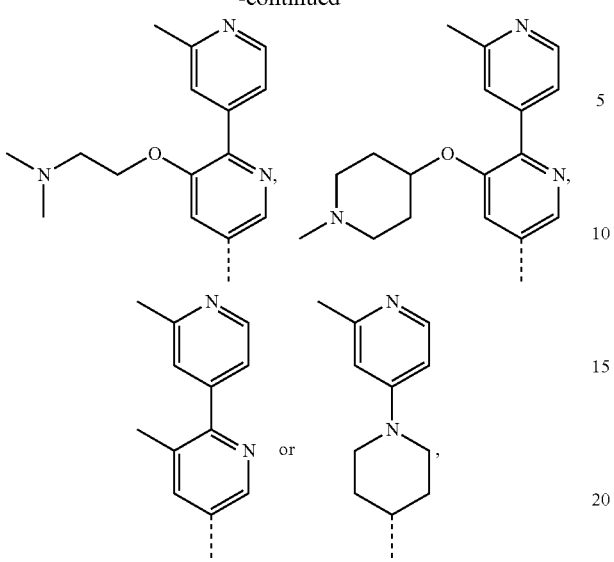

and other variables are as defined herein.

In some embodiments of the present disclosure, the above compound has a structure as shown in formula (I-3) or (I-4):

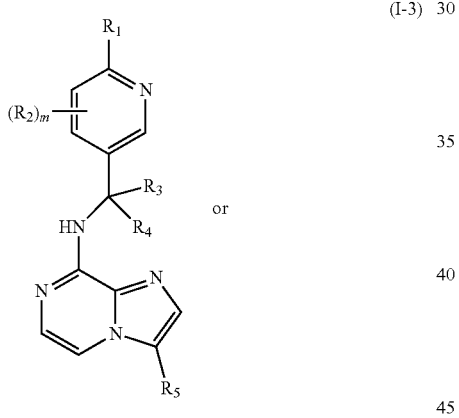

wherein R₁, R₂, R₃, R₄, R₅ and m are as defined herein.

In some embodiments of the present disclosure, the above compound has a structure as shown in formula (II-1):

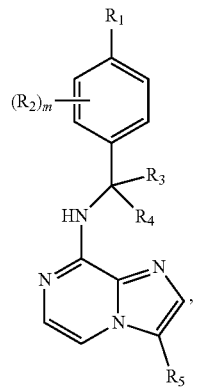

wherein $R_1$, $R_2$, $R_3$, $R_4$, $R_5$ and m are as defined herein.

In some embodiments of the present disclosure, the $R_1$ is pyridyl, wherein the pyridyl is optionally substituted with 1, 2 or 3 $R_a$, and $R_a$ and other variables are as defined herein.

In some embodiments of the present disclosure, the $R_1$ is pyrazolyl or pyridyl, wherein the pyrazolyl and pyridyl are optionally substituted with 1, 2 or 3 $R_a$, and $R_a$ and other variables are as defined herein.

In some embodiments of the present disclosure, the $R_1$ is

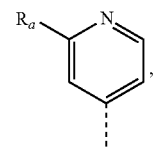

and $R_a$ and other variables are as defined herein.

In some embodiments of the present disclosure, the $R_1$ is

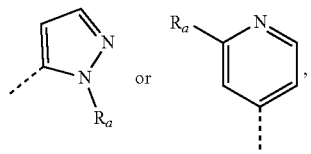

and $R_a$ and other variables are as defined herein.

In some embodiments of the present disclosure, the $R_1$ is

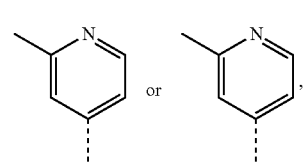

and other variables are as defined herein.

In some embodiments of the present disclosure, the $R_1$ is

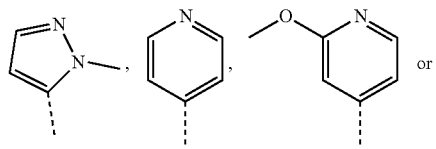

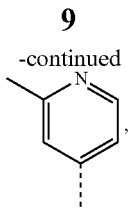

and other variables are as defined herein.

In some embodiments of the present disclosure, the above compound has a structure as shown in formula (I-5) or (I-6):

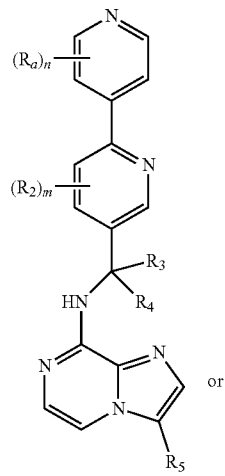

(I-5)

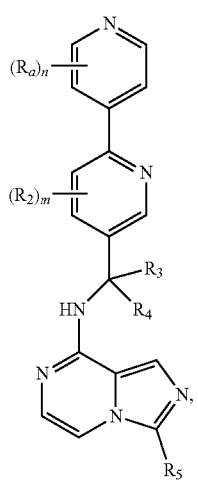

(I-6)

wherein $R_2$, $R_3$, $R_4$, $R_5$, m and each $R_a$ are as defined herein, and n is 1 or 2.

In some embodiments of the present disclosure, the above compound has a structure as shown in formula (II-2) or (II-3):

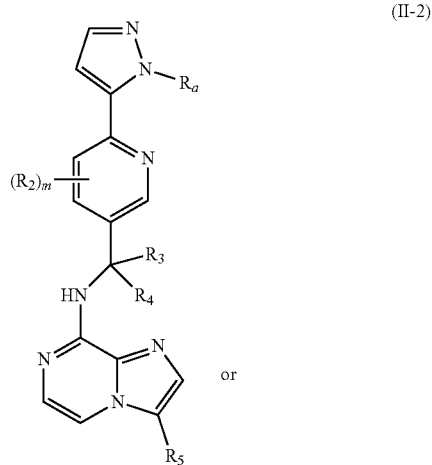

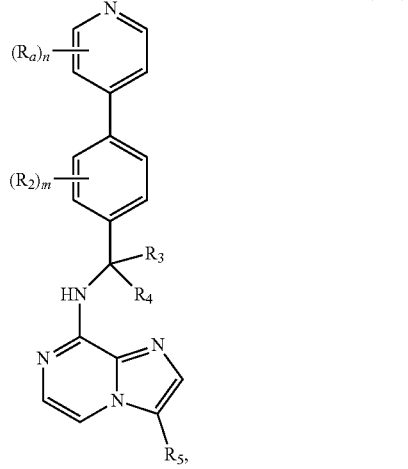

wherein $R_2$, $R_3$, $R_4$, $R_5$, m and each $R_a$ are as defined herein, and n is 1 or 2.

In some embodiments of the present disclosure, the each R is independently F, Cl, Br, CN, —$CH_3$ or —$CF_3$, and other variables are as defined herein.

In some embodiments of the present disclosure, the $R_b$ and $R_c$ are each independently H or —$CH_3$, or $R_b$ and $R_c$ together with the N atom to which they are attached form piperidinyl or morpholinyl, wherein the —$CH_3$, piperidinyl and morpholinyl are optionally substituted with 1, 2 or 3 R, and R and other variables are as defined herein.

In some embodiments of the present disclosure, the $R_b$ and $R_c$ are each independently H, —$CH_3$ or phenyl, or $R_b$ and $R_c$ together with the N atom to which they are attached form piperidinyl or morpholinyl, wherein the —$CH_3$, phenyl, piperidinyl and morpholinyl are optionally substituted with 1, 2 or 3 R, and R and other variables are as defined herein.

In some embodiments of the present disclosure, the $R_5$ is —C(=O)—$NR_bR_c$, phenyl, pyrazolyl, pyridyl, pyrazinyl, piperazinyl or cyclopropyl, wherein the phenyl, pyrazolyl, pyridyl, pyrazinyl, piperazinyl and cyclopropyl are optionally substituted with 1, 2 or 3 $R_d$, and $R_d$ and other variables are as defined herein.

In some embodiments of the present disclosure, the $R_5$ is —C(=O)—$NR_bR_c$, phenyl, pyrazolyl, pyridyl, pyrazinyl, piperidinyl, piperazinyl or cyclopropyl, wherein the phenyl, pyrazolyl, pyridyl, pyrazinyl, piperidinyl, piperazinyl and cyclopropyl are optionally substituted with 1, 2 or 3 $R_d$, and $R_d$ and other variables are as defined herein.

In some embodiments of the present disclosure, the $R_5$ is —C(=O)—$NR_bR_c$,

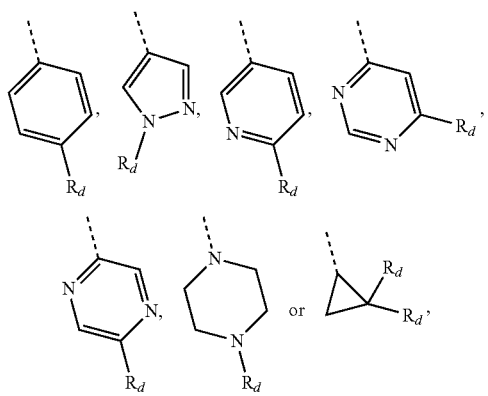

and $R_b$, $R_c$ and $R_d$ and other variables are as defined herein.

In some embodiments of the present disclosure, the $R_5$ is C(=O)—$NR_bR_c$,

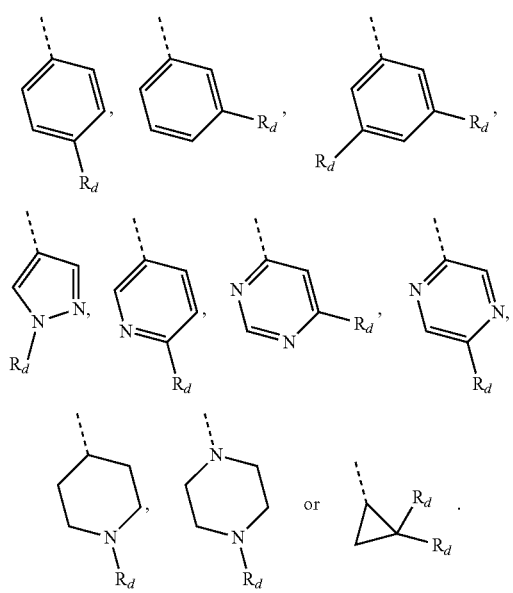

and $R_b$, $R_c$ and $R_d$ and other variables are as defined herein.

In some embodiments of the present disclosure, the $R_5$ is

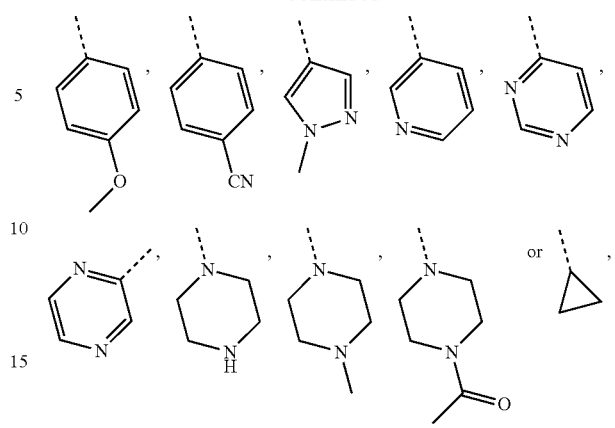

and other variables are as defined herein.

In some embodiments of the present disclosure, the $R_5$ is

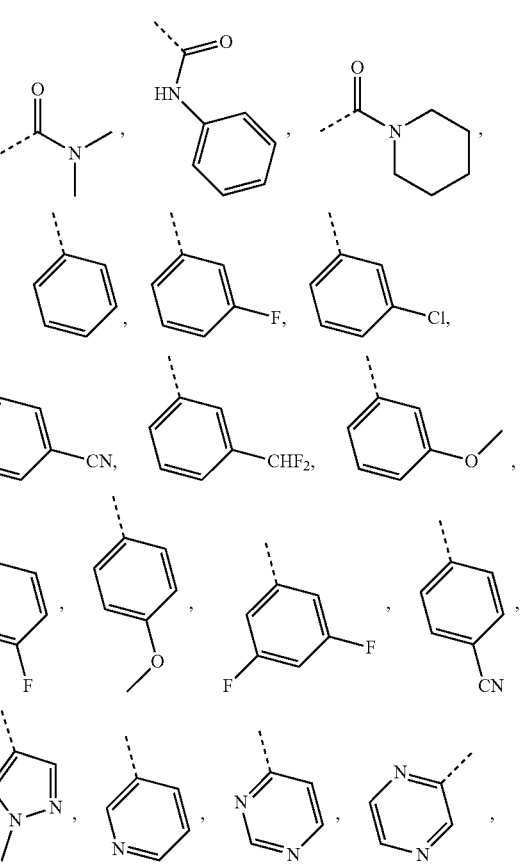

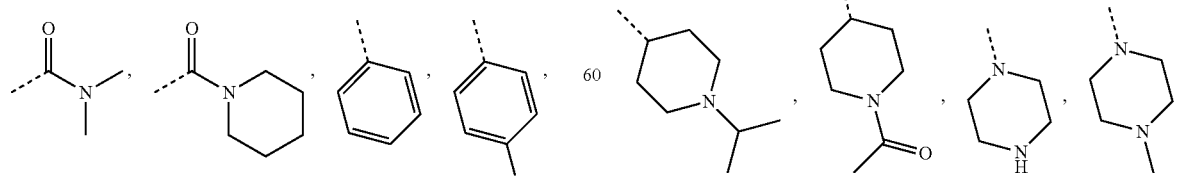

-continued
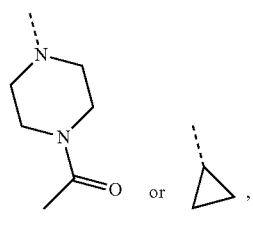
and other variables are as defined herein.
In some embodiments of the present disclosure, the compound has a structure as shown in any of formulas (I-7) to (I-13):
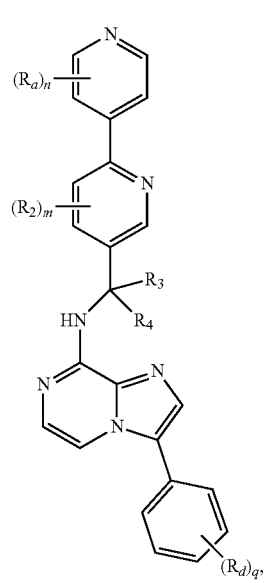
(I-7)
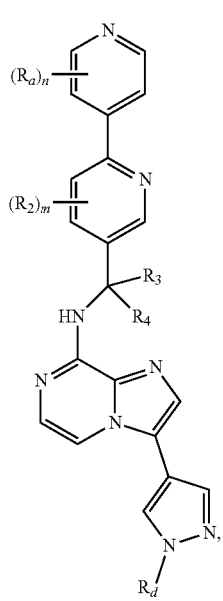
(I-8)
-continued
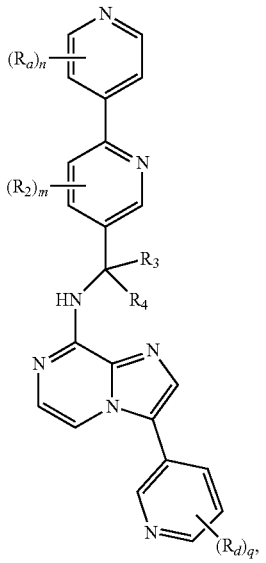
(I-9)
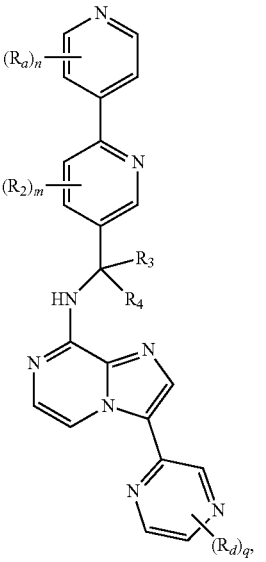
(I-10)

(I-11)

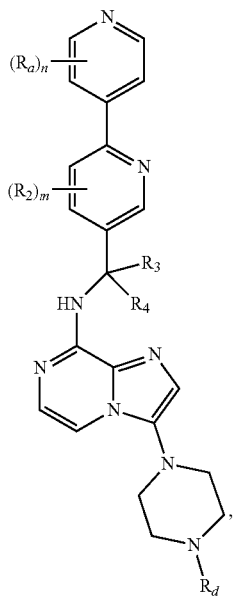

(I-12)

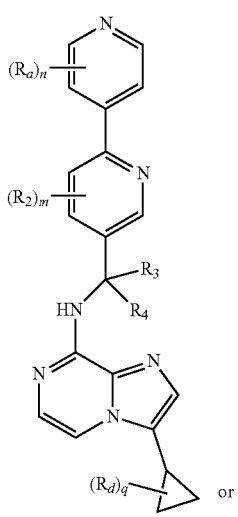 or (I-13)

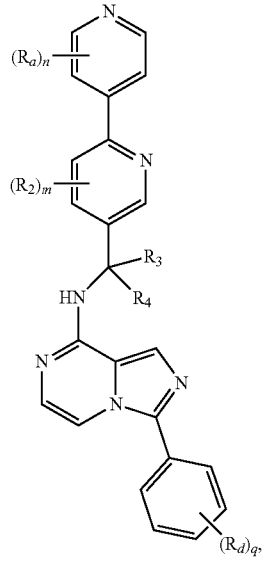

wherein $R_2$, $R_3$, $R_4$, m, n, $R_a$ and $R_d$ are as defined herein, and q is 1 or 2.

In some embodiments of the present disclosure, the compound has a structure as shown in formula (II-4):

(II-4)

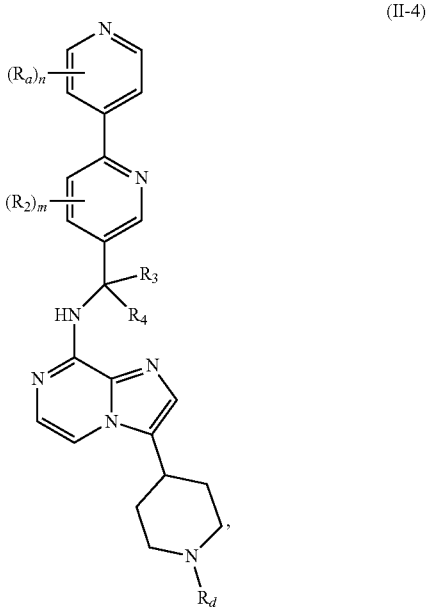

wherein $R_2$, $R_3$, $R_4$, m, n, $R_a$ and $R_d$ are as defined above.

In some embodiments of the present disclosure, the each $R_a$ is independently H, F, Cl, Br, I, CN, —$CH_3$, —$CH_2CH_3$ or —$CF_3$, and other variables are as defined herein.

In some embodiments of the present disclosure, the each $R_a$ is independently H, F, Cl, Br, I, CN, —$OCH_3$, —$CH_3$, —$CH_2CH_3$ or —$CF_3$, and other variables are as defined herein.

In some embodiments of the present disclosure, the each $R_d$ is independently H, F, Cl, CN, —C(=O)—$CH_3$, —$CH_3$, —$CH_2CH_3$, —$OCH_3$ or —$CF_3$, and other variables are as defined herein.

In some embodiments of the present disclosure, the each $R_d$ is independently H, F, Cl, CN, —C(=O)—CH$_3$, —CH$_3$, —CH$_2$CH$_3$, —CH$_2$(CH$_3$)$_2$, —OCH$_3$, —CHF$_2$ or —CF$_3$, and other variables are as defined herein.

In some embodiments of the present disclosure, the each $R_2$ is independently H, F, Cl, Br, I, CN, —CH$_3$, —CH$_2$CH$_3$ or —CF$_3$, and other variables are as defined herein.

In some embodiments of the present disclosure, the each $R_2$ is independently H, F, Cl, Br, I, CN,

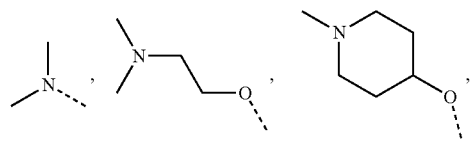

—CH$_3$, —CH$_2$CH$_3$ or —CF$_3$, and other variables are as defined herein.

In some embodiments of the present disclosure, the $R_3$ and $R_4$ are each independently H or —CH$_3$, and other variables are as defined herein.

In some embodiments of the present disclosure, the $R_3$ and $R_4$ are each independently H, —CH$_3$ or —CH$_2$OH, and other variables are as defined herein.

The present disclosure also includes some embodiments that are obtained by combining any of the above variables.

In some embodiments of the present disclosure, the above compound is a compound of the following formulas, a pharmaceutically acceptable salt thereof or an isomer thereof:

1

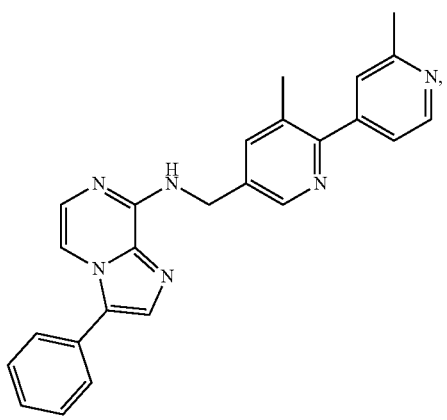

2

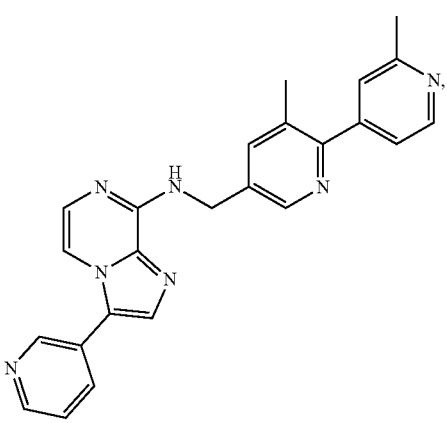

-continued

3

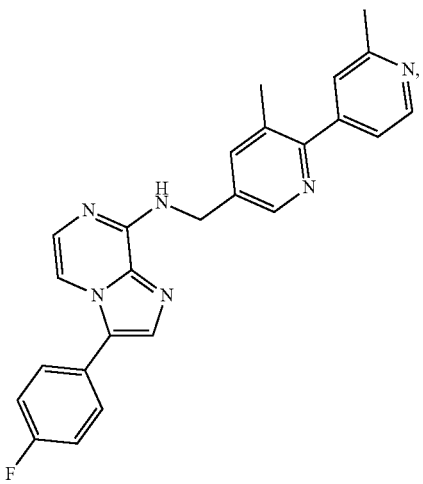

4

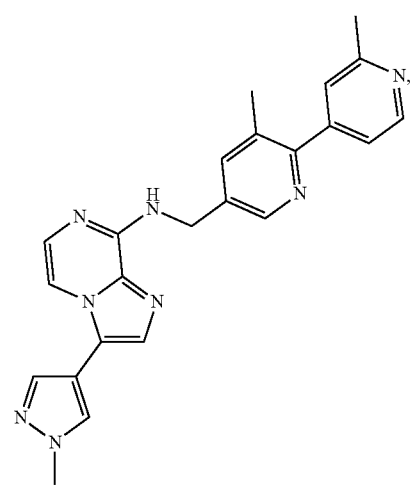

5

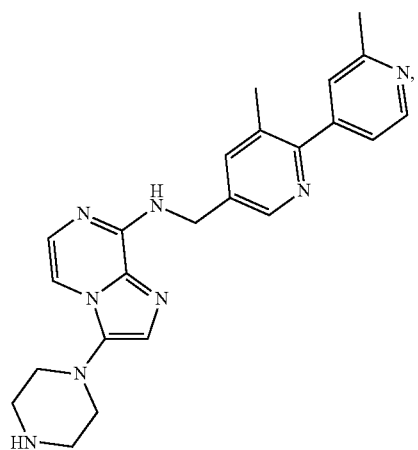

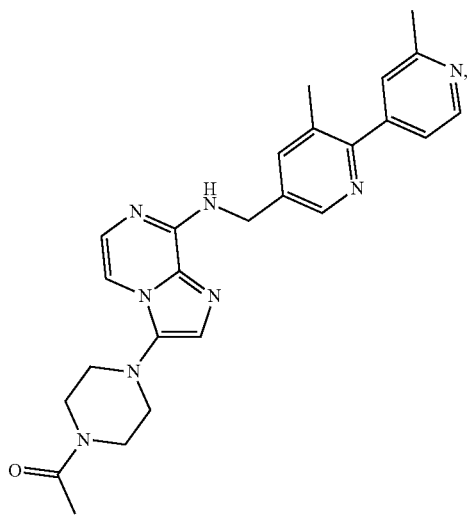
6
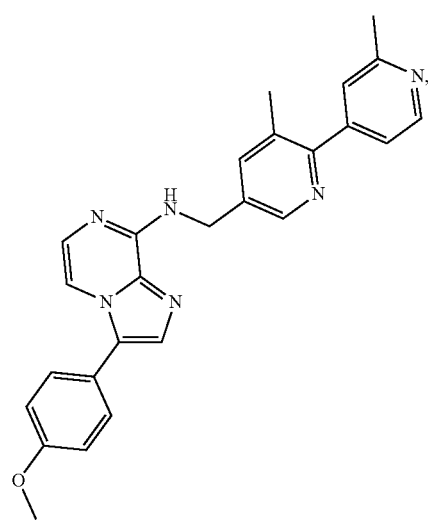
9
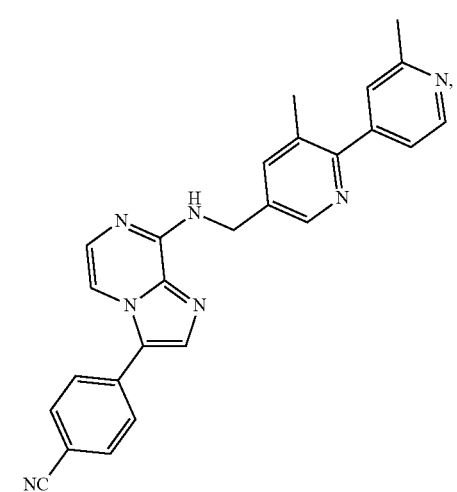
7
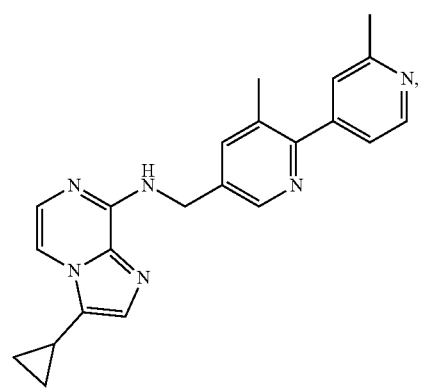
10
8
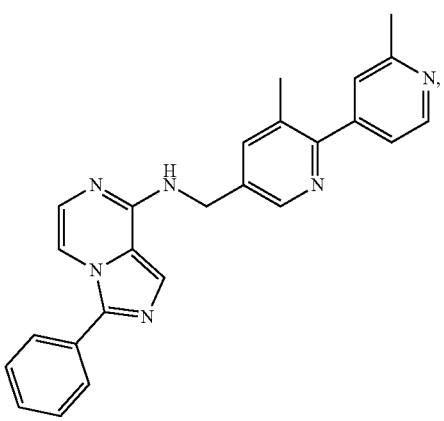
11

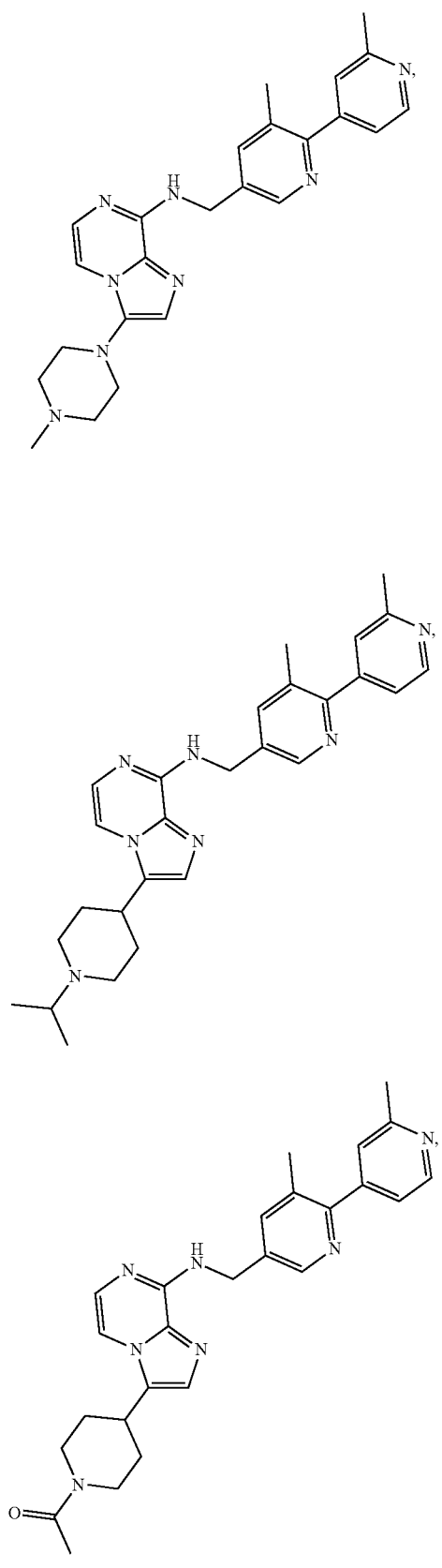
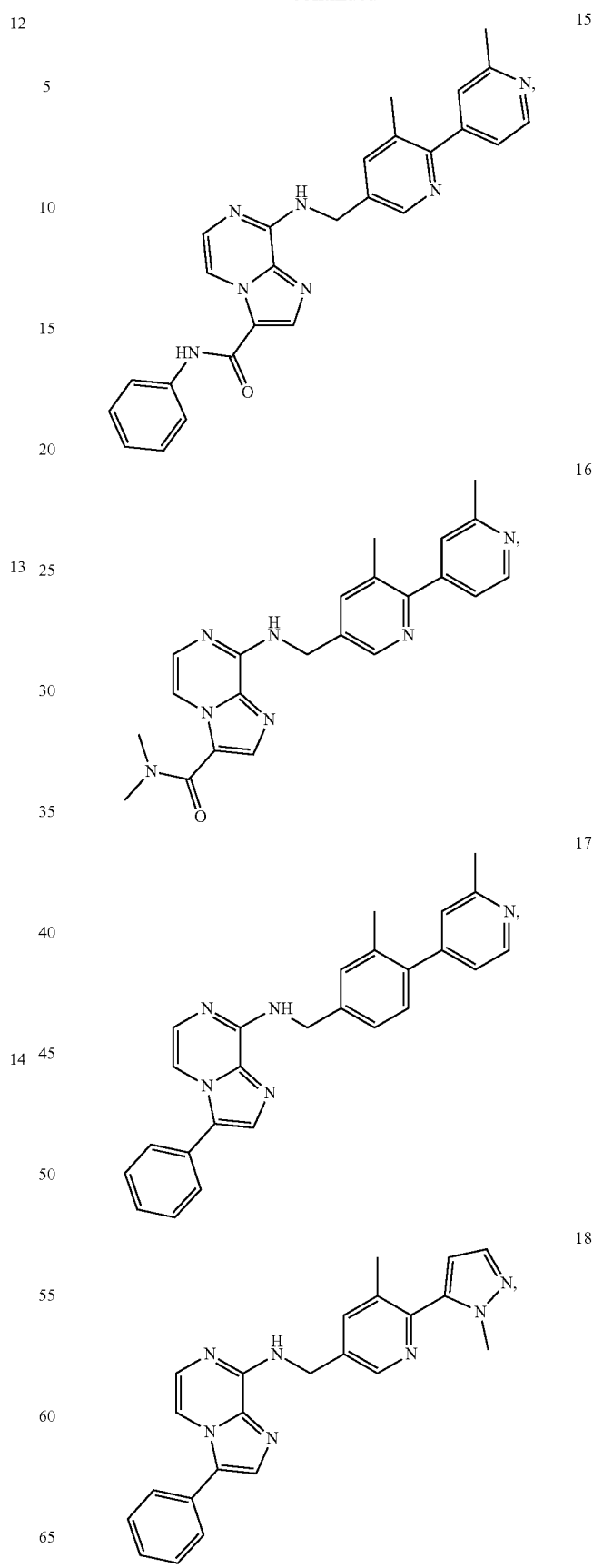

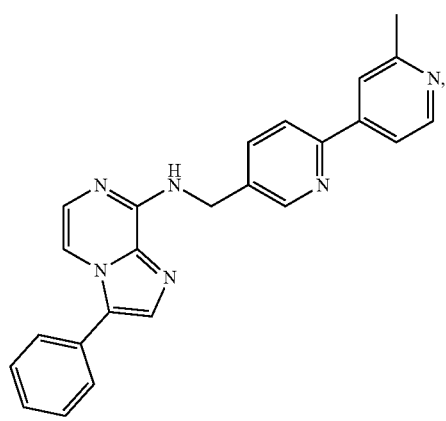
19
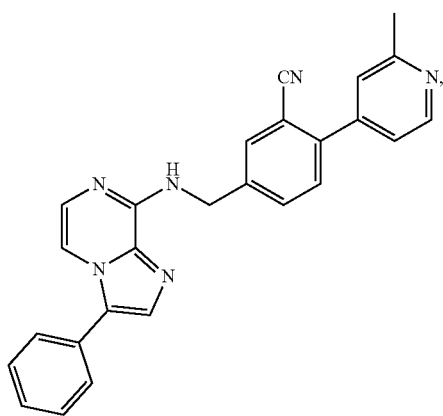
22
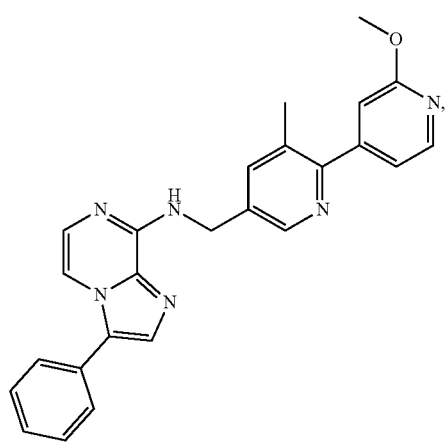
20
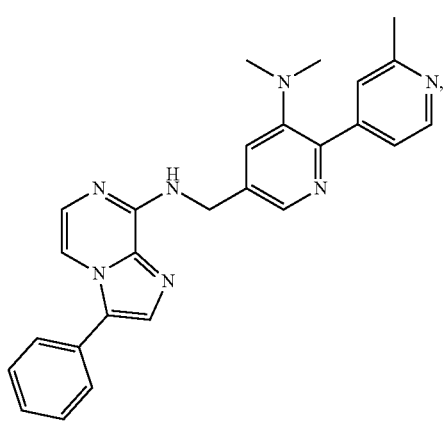
23
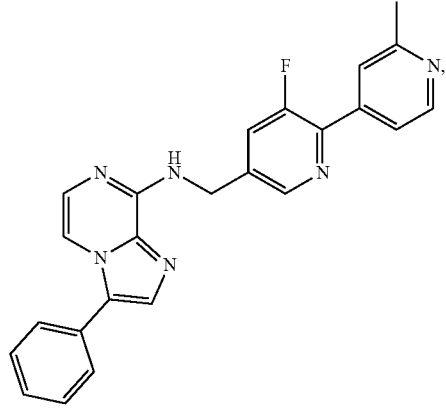
21
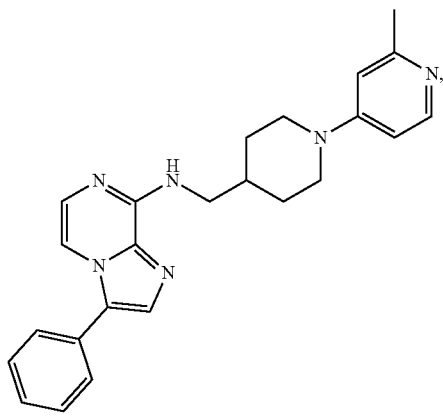
24

25
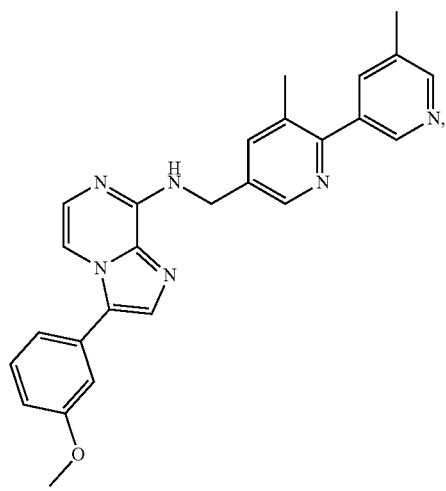
26
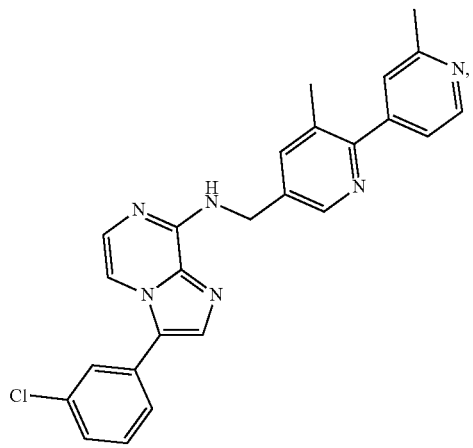
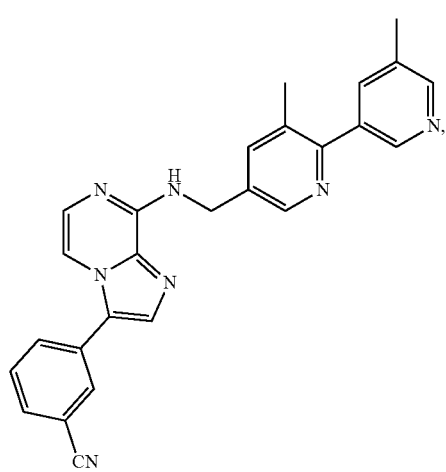
27
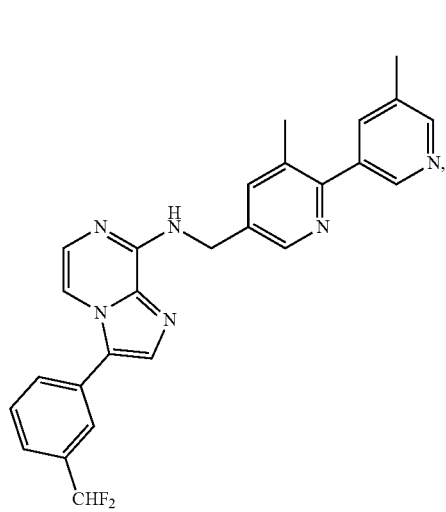
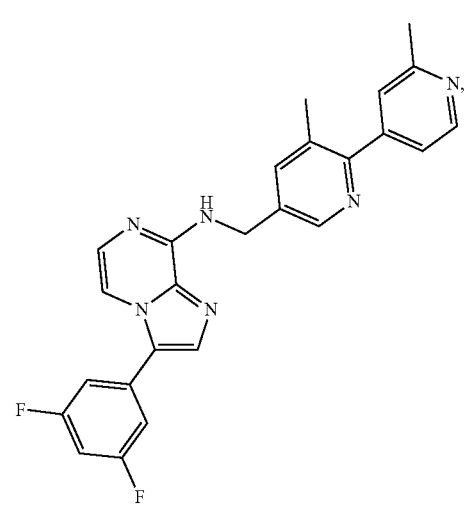

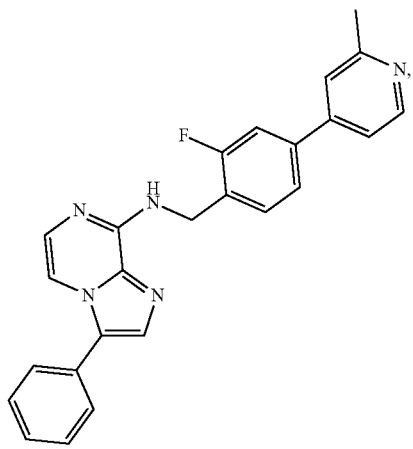

31

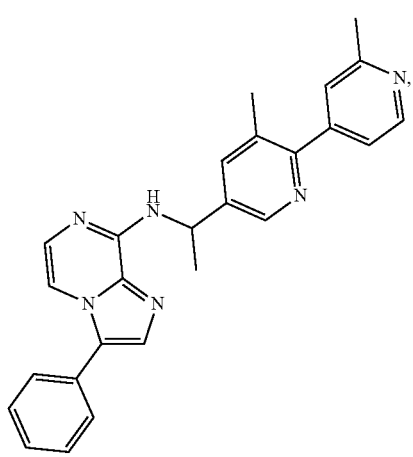

32

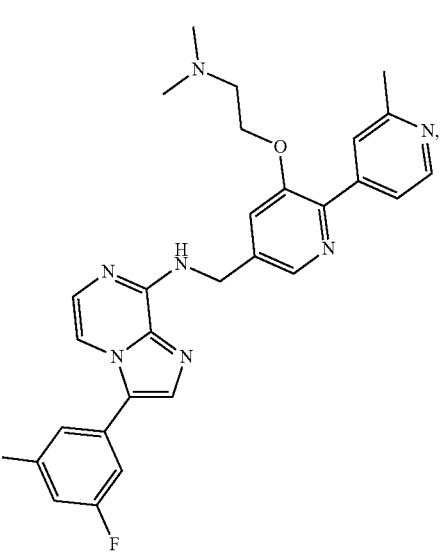

33

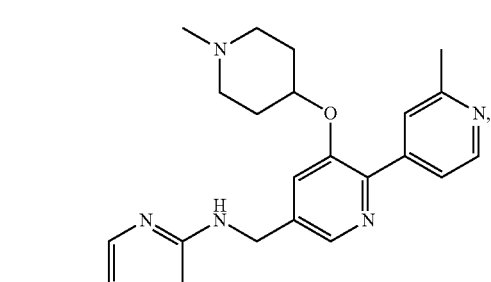

34

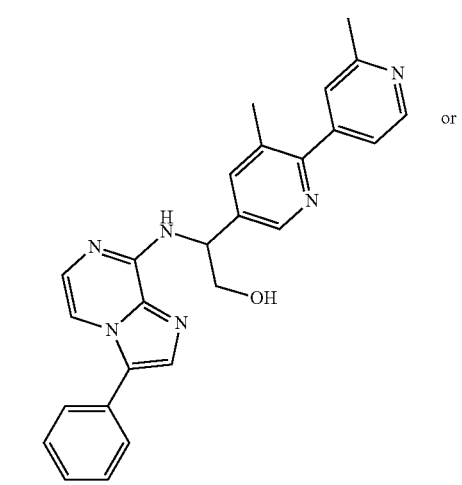

35 or

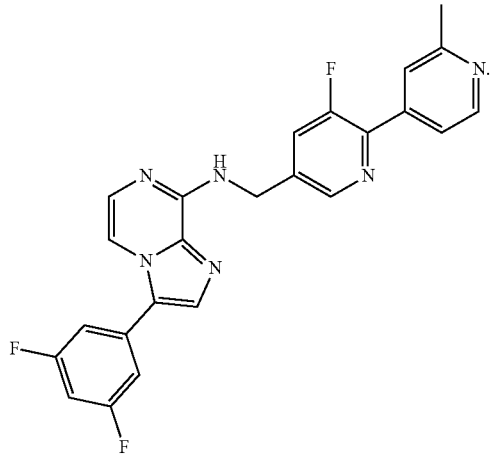

36

In another aspect, the present disclosure also provides a pharmaceutical composition, which contains a therapeutically effective amount of the above compound, a pharmaceutically acceptable salt thereof or an isomer thereof, and a pharmaceutically acceptable carrier.

The present disclosure also provides use of the above compound, the pharmaceutically acceptable salt thereof or the isomer thereof, and the above pharmaceutical composition in the manufacture of a medicament as a porcupine inhibitor.

The present disclosure also provides use of the above compound, the pharmaceutically acceptable salt thereof or the isomer thereof, and the above pharmaceutical composition in the manufacture of a medicament for the treatment of pancreatic cancer.

Technical Effects

The compound of the present disclosure has a good inhibitory effect on the excessive activation of the WNT/β-Catenin signaling pathway, thereby obtaining excellent tumor growth inhibitory activity. In vivo efficacy results of mouse pancreatic cancer Capan-2 xenograft tumor model show that, under the same dose, the tumor growth rate of mice given the compound of the present disclosure is significantly lower than that of LGK974, which further proves that the compound of the present disclosure has better activity of inhibiting a tumor.

Definitions and Terms

Unless otherwise specified, the following terms and phrases used herein are intended to have the following meanings. A specific term or phrase should not be considered indefinite or unclear in the absence of a particular definition, but should be understood in the conventional sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" means a salt of compounds disclosed herein that is prepared by reacting the compound having a specific substituent disclosed herein with a relatively non-toxic acid or base. When compounds disclosed herein contain a relatively acidic functional group, a base addition salt can be obtained by bringing the compound into contact with a sufficient amount of base in a pure solution or a suitable inert solvent. The pharmaceutically acceptable base addition salt includes a salt of sodium, potassium, calcium, ammonium, organic amine or magnesium or similar salts. When compounds disclosed herein contain a relatively basic functional group, an acid addition salt can be obtained by bringing the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds disclosed herein contain both basic and acidic functional groups and can be converted to any base or acid addition salt.

The pharmaceutically acceptable salt disclosed herein can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof.

Compounds disclosed herein may be present in a specific geometric or stereoisomeric form. The present disclosure contemplates all such compounds, including cis and trans isomers, (−)- and (+)-enantiomers, (R)- and (S)-enantiomers, diastereoisomer, (D)-isomer, (L)-isomer, and a racemic mixture and other mixtures, for example, a mixture enriched in enantiomer or diastereoisomer, all of which are encompassed within the scope disclosed herein. The substituent such as alkyl may have an additional asymmetric carbon atom. All these isomers and mixtures thereof are encompassed within the scope disclosed herein.

Unless otherwise specified, the term "enantiomer" or "optical isomer" means stereoisomers that are in a mirrored relationship with each other.

Unless otherwise specified, the term "cis-trans isomer" or "geometric isomer" is produced by the inability of a double bond or a single bond between ring-forming carbon atoms to rotate freely.

Unless otherwise specified, the term "diastereomer" means a stereoisomer in which two or more chiral centers of are contained in a molecule and is in a non-mirrored relationship between molecules.

Unless otherwise specified, "(+)" means dextroisomer, "(−)" means levoisomer, and "(±)" means racemate.

Unless otherwise specified, a wedged solid bond ( ⭯ ) and a wedged dashed bond ( ⭯ ) indicate the absolute configuration of a stereocenter; a straight solid bond ( ⭯ ) and a straight dashed bond ( ⭯ ) indicate the relative configuration of a stereocenter; a wavy line ( ⭯ ) indicates a wedged solid bond ( ⭯ ) or a wedged dashed bond ( ⭯ ); or a wavy line ( ⭯ ) indicates a straight solid bond ( ⭯ ) and a straight dashed bond ( ⭯ ).

Compounds disclosed herein may be present in a particular form. Unless otherwise specified, the terms "tautomer" or "tautomeric form" means that different functional groups are in dynamic equilibrium at room temperature and can be rapidly converted into each other. If tautomers are possible (as in solution), a chemical equilibrium of tautomers can be achieved. For example, proton tautomers (also known as prototropic tautomers) include interconversions by proton transfer, such as keto-enol isomerization and imine-enamine isomerization. Valence tautomers include interconversions by recombination of some bonding electrons. A specific example of keto-enol tautomerization is interconversion between two tautomers pentane-2, 4-dione and 4-hydroxypent-3-en-2-one.

Unless otherwise specified, the term "enriched in one isomer", "isomer enriched", "enriched in one enantiomer" or "enantiomeric enriched" means that the content of one isomer or enantiomer is less than 100%, and the content of the isomer or enantiomer is 60% or more, or 70% or more, or 80% or more, or 90% or more, or 95% or more, or 96% or more, or 97% or more, 98% or more, 99% or more, 99.5% or more, 99.6% or more, 99.7% or more, 99.8% or more, or 99.9% or more.

Unless otherwise specified, the term "isomer excess" or "enantiomeric excess" means the difference between the relative percentages of two isomers or two enantiomers. For example, if one isomer or enantiomer is present in an amount of 90% and the other isomer or enantiomer is present in an amount of 10%, the isomer or enantiomeric excess (ee value) is 80%.

Optically active (R)- and (S)-isomer, or D and L isomer can be prepared using chiral synthesis or chiral reagents or other conventional techniques. If one kind of enantiomer of certain compound disclosed herein is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (for example, carbamate generated from amine) Compounds disclosed herein may contain an unnatural proportion of atomic isotopes at one or more of the atoms that make up the compounds. For example, a compound may be labeled with a radioisotope such as tritium ($^3$H), iodine-125 ($^{125}$I) or C-14 ($^{14}$C). For another example, hydrogen can be replaced by heavy hydrogen to form a deuterated drug. The bond between deuterium and carbon is stronger than that between ordinary hydrogen and carbon. Compared with undeuterated drugs, deuterated drugs have advantages of reduced toxic side effects, increased drug stability, enhanced efficacy, and prolonged biological half-life of drugs. All changes in the isotopic composition of compounds disclosed herein, regardless of radioactivity, are included within the scope of the present disclosure. The term "optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted by a substituent, including deuterium and hydrogen variants, as long as the valence of the specific atom is normal and the substituted compound is stable. When the substituent is oxo (i.e., =O), it means two hydrogen atoms are substituted. Positions on an aromatic ring cannot be substituted by oxo. The term "optionally substituted" means an atom can be substituted by a substituent or not, unless otherwise specified, the species and number of the substituent may be arbitrary as long as being chemically achievable.

When any variable (such as R) occurs in the constitution or structure of a compound more than once, the definition of the variable at each occurrence is independent. Thus, for example, if a group is substituted by 0 to 2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When an enumerated substituent does not indicate the atom through which the enumerated substituent is linked to the substituted group, such substituent can be bonded through any of its atoms. For example, a pyridyl group as a substituent may be linked to the substituted group through any one of carbon atoms on the pyridine ring.

When an enumerated linking group does not indicate its linking direction, its linking direction is arbitrary. For example, when the linking group L in

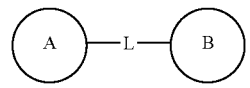

is -M-W—, the -M-W— can be linked to the ring A and the ring B in the same direction as the reading order from left to right to constitute

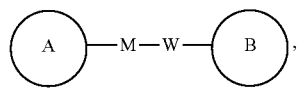

or can be linked to the ring A and the ring B in the reverse direction as the reading order from left to right to constitute

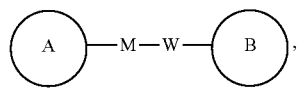

A combination of the linking groups, substituents and/or variants thereof is allowed only when such combination can result in a stable compound.

Unless otherwise specified, when a group has one or more connectable sites, any one or more sites of the group can be connected to other groups through chemical bonds. The chemical bonds between the sites and other groups can be represented by a straight solid bond ( ╱ ), a straight dashed bond ( ╱ ) or a wavy line

For example, the straight solid bond in —OCH$_3$ means that the group is connected to other groups through the oxygen atom in the group; the straight dashed bond in

means that the group is connected to other groups through the two ends of the nitrogen atom in the group; and the wavy line in

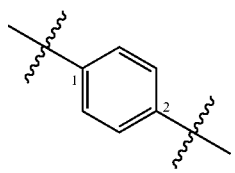 [SMILES: *c1ccc(*)cc1]

means that the group is connected to other groups through the carbon atoms at 1 and 2 sites in the phenyl group.

Unless otherwise specified, the number of atoms in a ring is usually defined as the number of ring members, for example, "5- to 7-membered ring" refers to a "ring" in which 5 to 7 atoms are arranged around.

Unless otherwise specified, "3- to 12-membered ring" means a cycloalkyl, heterocycloalkyl, cycloalkenyl or heterocycloalkenyl group composed of 3 to 12 ring atoms. The ring includes a single ring, and also includes a bicyclic or polycyclic ring system such as a spiro ring, a fused ring and a bridged ring. Unless otherwise specified, the ring optionally contains 1, 2 or 3 heteroatoms independently selected from O, S and N. The 3- to 12-membered ring includes 3- to 10-membered, 3- to 9-membered, 3- to 8-membered, 3- to 7-membered, 3- to 6-membered, 3- to 5-membered, 4- to 10-membered, 4- to 9-membered, 4- to 8-membered, 4- to 7-membered, 4- to 6-membered, 4- to 5-membered, 5- to 10-membered, 5- to 9-membered, 5- to 8-membered, 5- to 7-membered, 5- to 6-membered, 6- to 10-membered, 6- to 9-membered, 6- to 8-membered and 6- to 7-membered ring, etc. The term "5- to 7-membered heterocycloalkyl" includes piperidinyl, etc., but does not include phenyl. The term "ring" also includes a ring system containing at least one ring, wherein each "ring" independently meets the above definition.

Unless otherwise specified, the term "$C_{1-6}$ alkyl" is used to refer to a linear or branched saturated hydrocarbon group composed of 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$ and $C_5$ alkyl, etc. It may be monovalent (e.g., methyl), divalent (e.g., methylene) or multivalent (e.g., methine). Examples of $C_{1-6}$ alkyl include, but are not limited to, methyl (Me), ethyl (Et), propyl (including n-propyl and isopropyl), butyl (including n-butyl, isobutyl, s-butyl and t-butyl), pentyl (including n-pentyl, isopentyl and neopentyl), hexyl, etc.

Unless otherwise specified, the term "$C_{1-4}$ alkyl" is used to refer to a linear or branched saturated hydrocarbon group composed of 1 to 4 carbon atoms. The $C_{1-4}$ group includes $C_{1-2}$, $C_{1-3}$ and $C_{2-3}$ alkyl, etc. It may be monovalent (e.g., methyl), divalent (e.g., methylene) or multivalent (e.g., methine). Examples of $C_{1-4}$ alkyl groups include, but are not limited to, methyl (Me), ethyl (Et), propyl (including n-propyl and isopropyl), butyl (including n-butyl, isobutyl, s-butyl and t-butyl), etc.

Unless otherwise specified, the term "$C_{1-3}$ alkyl" is used to refer to a linear or branched saturated hydrocarbon group composed of 1 to 3 carbon atoms. The $C_{1-3}$ alkyl group includes $C_{1-2}$ and $C_{2-3}$ alkyl groups and the like. It may be monovalent (e.g., methyl), divalent (e.g., methylene) or multivalent (e.g., methine). Examples of $C_{1-3}$ alkyl groups include, but are not limited to, methyl (Me), ethyl (Et), propyl (including n-propyl and isopropyl), and the like.

Unless otherwise specified, the term "$C_{1-3}$ alkoxy" refers to an alkyl group containing 1 to 3 carbon atoms and attached to the remainder of a molecule by an oxygen atom. The $C_{1-3}$ alkoxy group includes $C_{1-2}$, $C_{2-3}$, $C_3$, $C_2$ alkoxy groups, and the like. Examples of $C_{1-3}$ alkoxy groups include, but are not limited to, methoxy, ethoxy, propoxy (including n-propoxy and isopropoxy), and the like.

Unless otherwise specified, "$C_{3-6}$ cycloalkyl" is used to refer to a saturated cyclic hydrocarbon group composed of 3 to 6 carbon atoms, which is a single ring system. The $C_{3-6}$ cycloalkyl includes $C_{3-5}$, $C_{3-4}$, $C_{4-5}$ or $C_{4-6}$ cycloalkyl and the like. It may be monovalent, divalent or multivalent. Examples of $C_{3-6}$ cycloalkyl groups include, but are not limited to, cyclopropyl, cyclobutyl, cyclopentyl, cyclohexyl, etc.

Unless otherwise specified, "$C_{3-5}$ cycloalkyl" is used to refer to a saturated cyclic hydrocarbon group composed of 3 to 5 carbon atoms, which is a single ring system. The $C_{3-5}$ cycloalkyl includes $C_{3-4}$ or $C_{4-5}$ cycloalkyl and the like. It may be monovalent, divalent or multivalent. Examples of $C_{3-5}$ cycloalkyl groups include, but are not limited to, cyclopropyl, cyclobutyl, cyclopentyl, etc.

Unless otherwise specified, "$C_{5-6}$ cycloalkyl" is used to refer to a saturated cyclic hydrocarbon group composed of 5 to 6 carbon atoms, which is a single ring system. The $C_{5-6}$ cycloalkyl includes $C_5$ or $C_6$ cycloalkyl and the like. It may be monovalent, divalent or multivalent. Examples of $C_{5-6}$ cycloalkyl groups include, but are not limited to, cyclopentyl, cyclohexyl, etc.

Unless otherwise specified, the term "$C_{6-10}$ aromatic ring" and "$C_{6-10}$ aryl" can be used interchangeably in the present disclosure. The term "$C_{6-10}$ aromatic ring" or "$C_{6-10}$ aryl" refers to a cyclic hydrocarbon group with a conjugated π-electron system composed of 6 to 10 carbon atoms, which can be monocyclic, fused bicyclic or fused tricyclic system, wherein each ring is aromatic. It may be monovalent, divalent or multivalent. $C_{6-10}$ aryl includes $C_{6-9}$, $C_9$, $C_{10}$ and $C_6$ aryl and the like. Examples of $C_{6-10}$ aryl groups include, but are not limited to, phenyl, naphthyl (including 1-naphthyl, 2-naphthyl, etc.).

Unless otherwise specified, the terms "5- to 6-membered heteroaromatic ring" and "5- to 6-membered heteroaryl" may be used interchangeably in the present disclosure. The term "5- to 6-membered heteroaryl" refers to a monocyclic group having a conjugated π-electron system and composed of 5 to 6 ring atoms, of which 1, 2, 3 or 4 ring atoms are heteroatoms independently selected from O, S and N, and the remainder atoms are carbon atoms, wherein the nitrogen atom is optionally quaternized and the nitrogen and sulfur heteroatoms are optionally oxidized (i.e., NO and $S(O)_p$, p is 1 or 2). The 5- to 6-membered heteroaryl group may be attached to the remainder of a molecule by a heteroatom or a carbon atom. The 5- to 6-membered heteroaryl group includes 5-membered and 6-membered heteroaryl groups. Examples of the 5- to 6-membered heteroaryl group include, but are not limited to, pyrrolyl (including N-pyrrolyl, 2-pyrrolyl, 3-pyrrolyl, and the like), pyrazolyl (including 2-pyrazolyl and 3-pyrazolyl, and the like), imidazolyl (including N-imidazolyl, 2-imidazolyl, 4-imidazolyl, and 5-imidazolyl, and the like), oxazolyl (including 2-oxazolyl, 4-oxazolyl, and 5-oxazolyl, and the like), triazolyl (1H-1,2,3-triazolyl, 2H-1,2,3-triazolyl, 1H-1,2,4-triazolyl and 4H-1,2,4-triazolyl, and the like), tetrazolyl, isoxazolyl (3-isoxazolyl, 4-isoxazolyl and 5-isoxazolyl, and the like), thiazolyl (including 2-thiazolyl, 4-thiazolyl and 5-thiazolyl, and the like), furyl (including 2-furyl and 3-furyl, and the like), thienyl (including 2-thienyl and 3-thienyl, and the like), pyridyl (including 2-pyridyl, 3-pyridyl and 4-pyridyl, and the like), pyrazinyl or pyrimidinyl (including 2-pyrimidinyl and 4-pyrimidinyl, and the like).

Unless otherwise specified, the terms "6-membered heteroaromatic ring" and "6-membered heteroaryl" can be used interchangeably in the present disclosure. The term "6-membered heteroaryl" refers to a monocyclic group with a conjugated π-electron system composed of 6 ring atoms, of which 1, 2, 3 or 4 ring atoms are heteroatoms independently selected from O, S and N, and the remainder atoms are carbon atoms, wherein the nitrogen atom is optionally quaternized and the nitrogen and sulfur heteroatoms are optionally oxidized (i.e., NO and $S(O)_p$, p is 1 or 2). A 6-membered heteroaryl group can be connected to the remainder of a molecule through a heteroatom or a carbon atom. Examples of 6-membered heteroaryl groups include, but are not limited to, pyridyl (including 2-pyridyl, 3-pyridyl, and 4-pyridyl, etc.), pyrazinyl or pyrimidinyl (including 2-pyrimidinyl and 4-pyrimidinyl, etc.).

Unless otherwise specified, the term "5- to 6-membered heterocycloalkyl" by itself or in combination with other terms means a saturated cyclic group composed of 5 to 6 ring atoms, of which 1, 2, 3 or 4 ring atoms are heteroatoms independently selected from O, S and N, and the remainder are carbon atoms, wherein the nitrogen atom is optionally quaternized, and nitrogen and sulfur heteroatoms can be optionally oxidized (i.e., NO and $S(O)_p$, p is 1 or 2). It includes monocyclic and bicyclic ring systems, wherein the bicyclic ring system includes spiro, fused and bridged rings. In addition, as far as the "5- to 6-membered heterocycloalkyl" is concerned, a heteroatom may occupy the connection position of the heterocycloalkyl group with the remainder of the molecule. The 5- to 6-membered heterocycloalkyl includes 5-membered and 6-membered heterocycloalkyl. Examples of 5- to 6-membered heterocycloalkyl groups include, but are not limited to, pyrrolidinyl, pyrazolidinyl, imidazolidinyl, tetrahydrothienyl (including tetrahydrothiophen-2-yl and tetrahydrothiophen-3-yl, etc.), tetrahydrofuranyl (including tetrahydrofuran-2-yl, etc.), tetrahydropyranyl, piperidinyl (including 1-piperidinyl, 2-piperidinyl and 3-piperidinyl, etc.), piperazinyl (including 1-piperazinyl and 2-piperazinyl, etc.), morpholinyl (including 3-morpholinyl and 4-morpholinyl, etc.), dioxanyl, dithiazyl, isoxazolidinyl, isothiazolidinyl, 1,2-oxazinyl, 1,2-thiazinyl, hexahydropyridazinyl, homopiperazinyl or homopiperidinyl, etc.

Unless otherwise specified, $C_{n-n+m}$ or $C_n-C_{n+m}$ includes any one of n to n+m carbons. For example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$. $C_{n-n+m}$ or $C_n-C_{n+m}$ also includes any range of n to n+m. For example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, $C_{9-12}$, and the like. Similarly, the n-membered to n+m-membered ring means that the number of atoms on the ring is n to n+m. For example, 3- to 12-membered ring includes 3-membered ring, 4-membered ring, 5-membered ring, 6-membered ring, 7-membered ring, 8-membered ring, 9-membered ring, 10-membered ring, 11-membered ring, and 12-membered ring. The n-membered to n+m-membered ring also means that the number of atoms on the ring includes any range from n to n+m. For example, 3- to 12-membered ring includes 3- to 6-membered ring, 3- to 9-membered ring, 5- to 6-membered ring, 5- to 7-membered ring, 6- to 7-membered ring, 6- to 8-membered ring, and 6- to 10-membered ring, and the like.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonate and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g., acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

Compounds disclosed herein can be prepared by a variety of synthetic methods well known to those skilled in the art, including the following enumerated embodiment, the embodiment formed by the following enumerated embodiment in combination with other chemical synthesis methods, and equivalent replacement well known to those skilled in the art. Alternative embodiments include, but are not limited to the embodiment disclosed herein.

Solvents used in the present disclosure are commercially available.

The following abbreviations are used in the present disclosure: DMF represents N,N-dimethylformamide; $K_2CO_3$ represents potassium carbonate; EtOAc represents ethyl acetate; EA represents ethyl acetate; THF represents tetrahydrofuran; MeOH represents methanol; DCM represents dichloromethane; DMSO represents dimethyl sulfoxide; PE represents petroleum ether; EtOH represents ethanol; ACN represents acetonitrile; TFA represents trifluoroacetate; FA represents formic acid; $NH_3.H_2O$ represents ammonia; TEA represents triethylamine; DIPEA represents N,N-diisopropylethylamine; $Boc_2O$ represents di-tert-butyl dicarbonate; Boc represents tert-butoxycarbonyl, which is a protecting group for amino; LCMS represents liquid chromatograph mass spectrometry; HPLC represents high-performance liquid chromatography; and TLC represents thin-layer chromatography.

Compounds are named according to general naming principles in the art or by ChemDraw® software, and commercially available compounds are named with their vendor directory names.

DETAILED DESCRIPTION OF THE INVENTION

The present disclosure is described in detail below by means of examples. However, it is not intended that these examples have any disadvantageous limitations to the present disclosure. The present disclosure has been described in detail herein, and embodiments are also disclosed herein. It will be apparent to those skilled in the art that various changes and modifications may be made to the embodiments disclosed herein without departing from the spirit and scope disclosed herein.

Example 1

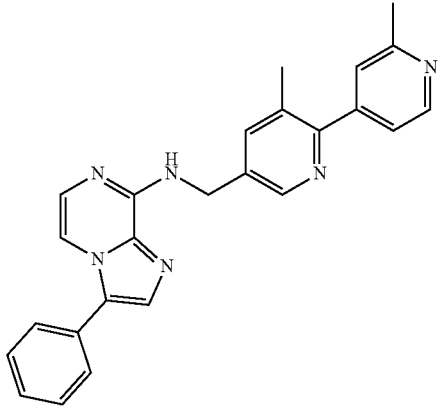

Route for Synthesis:

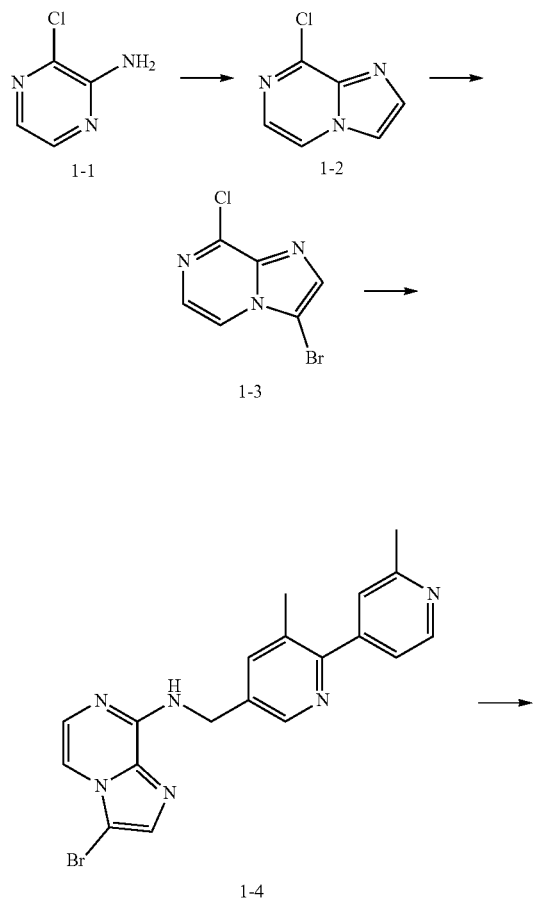

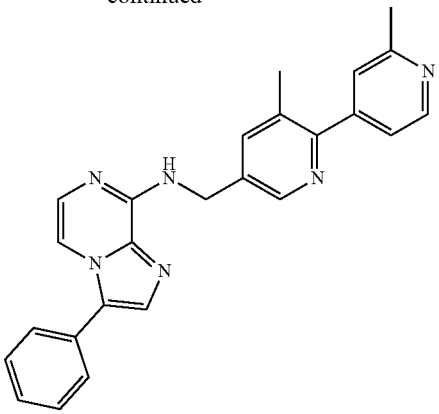

Step 1

The compound bromoacetaldehyde diethyl acetal (7.61 g, 38.60 mmol) was dissolved in water (10 mL) and trifluoroacetic acid (1.14 mL), and stirred at 25° C. for 1 hour. After the reaction was completed, the reaction mixture was diluted with water (30 ml), and the mixture was extracted with ethyl acetate (15 ml×3). The organic phases were combined, dried with anhydrous sodium sulfate, filtered, and concentrated under reduced pressure. The residue and compound 1-1 (2 g, 15.44 mmol) were dissolved in ethylene glycol dimethyl ether (25 ml) and then trifluoroacetic acid (1.14 ml) was added. The reaction mixture was stirred at 90° C. for 3 hours. After the reaction was completed, the reaction solution was poured into water (50 ml) and ethyl acetate (30 ml). The mixture was adjusted to pH 8 with saturated aqueous sodium bicarbonate solution, and extracted with ethyl acetate (30 ml×3). The organic phases were combined, dried with anhydrous sodium sulfate, filtered, and concentrated under reduced pressure to give a crude product of compound 1-2.

$^1$H NMR (400 MHz, CD$_3$OD) δ ppm 8.50 (d, J=4.5 Hz, 1H), 8.05-8.24 (m, 1H), 7.83 (s, 1H), 7.71 (d, J=4.6 Hz, 1H). MS-ESI Calculated [M+H]$^+$ 154, Found 154.

Step 2

Compound 1-2 (2.8 g, 18.23 mmol) was dissolved in dichloromethane (30 ml) and then N-bromosuccinimide (3.25 g, 18.23 mmol) was added. The reaction mixture was stirred at 30° C. for 2 hours. After the reaction was completed, the reaction solution was concentrated under reduced pressure. Water was added (50 ml), and the mixture was extracted with ethyl acetate (30 ml×3). The organic phases were combined, dried with anhydrous sodium sulfate, filtered, and concentrated under reduced pressure. The residue was isolated by column chromatography to give crude product of compound 1-3. MS-ESI Calculated [M+H]$^+$ 231 and 233, Found 231 and 233.

Step 3

Compound 1-3 (120 mg, 516.21 μmol), (2',3-dimethyl-[2,4'-bipyridyl]-5-yl)methylamine (121.10 mg, 567.83 μmol) and diisopropylethylamine (200.15 mg, 1.55 mmol, 269.74 μl) were dissolved in N-methylpyrrolidone (2 ml) and reacted in microwave at 200° C. for 2 hours. After the reaction was completed, the reaction solution was concentrated under reduced pressure. Water was added (50 ml), and the mixture was extracted with dichloromethane (30 ml×3). The organic phases were combined, dried with anhydrous sodium sulfate, filtered, and concentrated under reduced pressure. The residue was isolated by high-performance liquid chromatography (formic acid condition) to give compound 1-4.

$^1$H NMR (400 MHz, CD$_3$OD) δ ppm 8.38-8.69 (m, 2H), 7.84 (s, 1H), 7.62 (d, J=4.8 Hz, 1H), 7.59 (s, 1H), 7.40-7.47 (m, 2H), 7.36 (d, J=5.4 Hz, 1H), 4.84 (br s, 2H), 2.61 (s, 3H), 2.34 (s, 3H).

Step 4

Compound 1-4 (20 mg, 48.87 μmol) was dissolved in dioxane (2 ml), and then phenylboronic acid (7.15 mg, 58.64 μmol), potassium acetate (9.59 mg, 97.73 μmol), 1,1'-bis(diphenylphosphino)ferrocene palladium dichloride (3.58 mg, 4.89 μmol) were added in sequence. The reaction mixture was stirred at 100° C. under nitrogen protection for 7 hours. After the reaction was completed, the reaction solution was concentrated under reduced pressure. Water was added (30 ml), and the mixture was extracted with ethyl acetate (15 ml×3). The organic phases were combined, dried with anhydrous sodium sulfate, filtered, and concentrated under reduced pressure. The residue was isolated by thin-layer chromatography, and then isolated by high-performance liquid chromatography (formic acid condition) to give compound 1.

$^1$H NMR (400 MHz, CD$_3$OD) δ ppm 8.54 (s, 1H), 8.50 (br d, J=4.9 Hz, 1H), 7.86 (s, 1H), 7.77 (d, J=4.8 Hz, 1H), 7.60-7.69 (m, 3H), 7.56 (t, J=7.6 Hz, 2H), 7.45-7.52 (m, 1H), 7.43 (s, 1H), 7.30-7.38 (m, 2H), 4.58 (br s, 5H), 2.60 (s, 3H), 2.34 (s, 3H). MS-ESI Calculated [M+H]$^+$ 407, Found 407.

Example 2

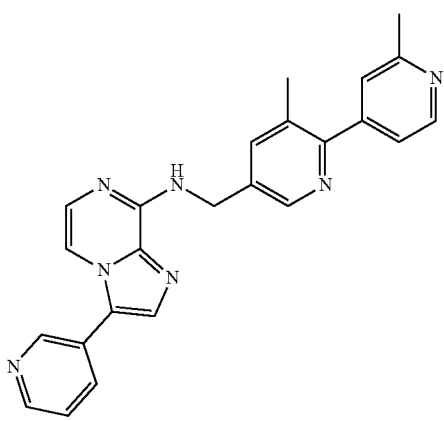

2

Route for Synthesis:

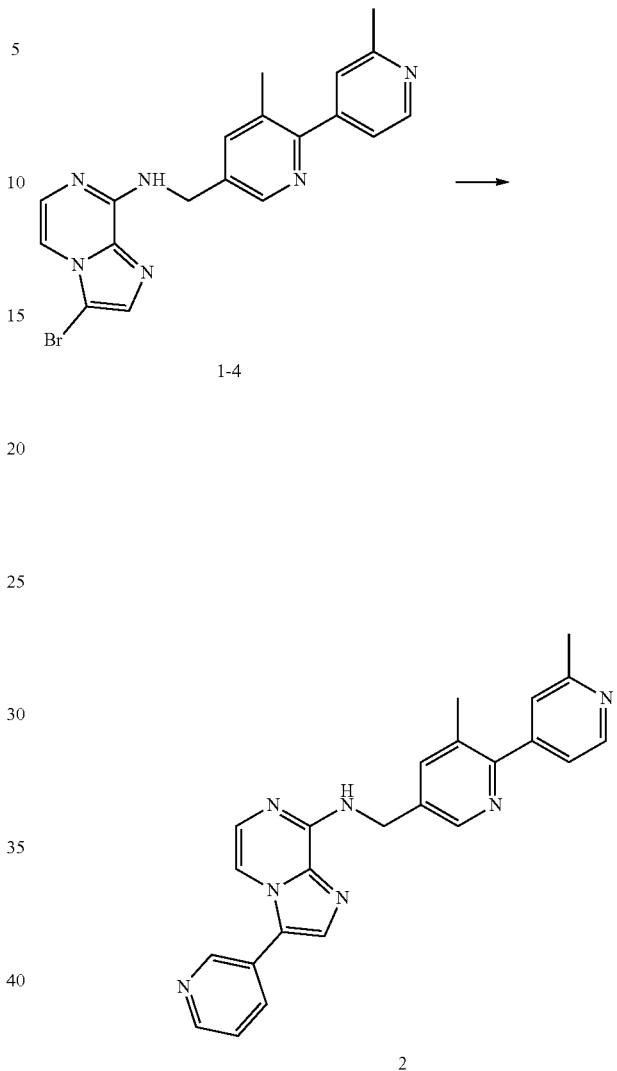

Compound 1-4 (80 mg, 195.46 μmol) was dissolved in dioxane (2 ml) and water (0.5 ml), and then 3-pyridineboronic acid (31.23 mg, 254.10 μmol), sodium carbonate (41.43 mg, 390.93 μmol) and 1,1'-bis(diphenylphosphino)ferrocene palladium dichloride (14.30 mg, 19.55 μmol) were added in sequence. The reaction mixture was stirred at 100° C. under nitrogen protection for 16 hours. After the reaction was completed, the reaction solution was concentrated under reduced pressure. Water was added (30 ml), and the mixture was extracted with ethyl acetate (15 ml×3). The organic phases were combined, dried with anhydrous sodium sulfate, filtered, and concentrated under reduced pressure. The residue was isolated by thin-layer chromatography, and then isolated by high-performance liquid chromatography (formic acid condition) to give compound 2.

$^1$H NMR (400 MHz, CD$_3$OD) δ ppm 8.84 (s, 1H), 8.65 (br d, J=4.5 Hz, 1H), 8.54 (s, 1H), 8.51 (d, J=5.3 Hz, 1H), 8.15 (dt, J=8.1, 1.8 Hz, 1H), 7.87 (d, J=1.4 Hz, 1H), 7.74-7.82 (m, 2H), 7.64 (dd, J=7.7, 4.9 Hz, 1H), 7.44 (s, 1H), 7.40 (d, J=4.9 Hz, 1H), 7.37 (d, J=5.3 Hz, 1H), 4.87 (s, 2H), 2.61 (s, 3H), 2.35 (s, 3H). MS-ESI Calculated [M+H]$^+$ 408, Found 408.

Example 3

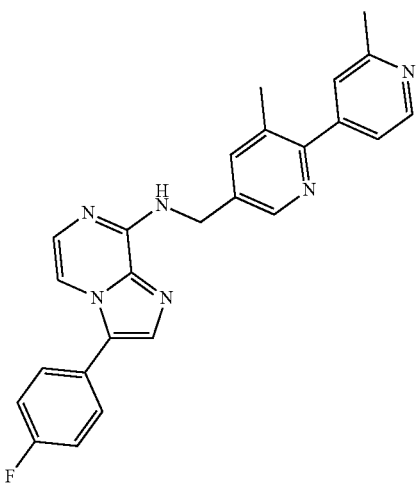

Route for Synthesis:

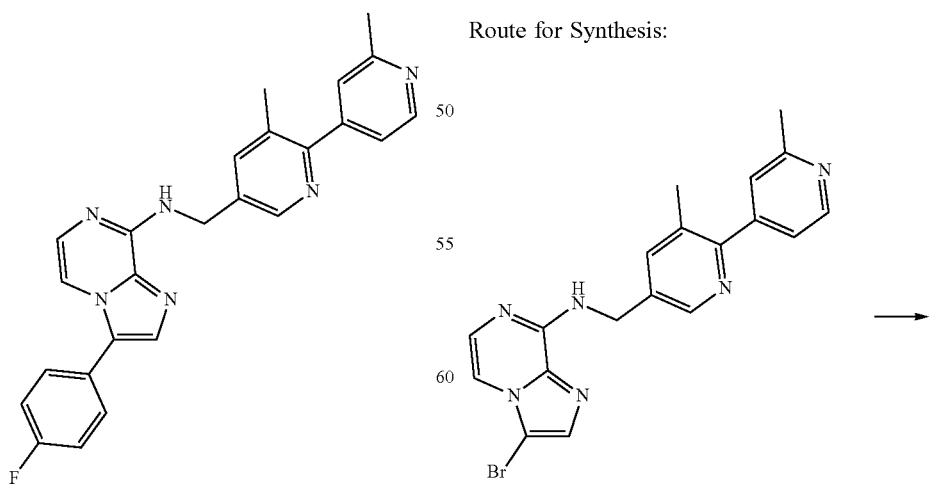

The preparation method was the same as that of Example 2, except of using 4-fluorophenylboronic acid (17.55 mg, 125.46 μmol) to replace 3-pyridineboronic acid (31.23 mg, 254.10 μmol). After the reaction was completed, the reaction solution was extracted with ethyl acetate (5 ml×3). The organic phase was washed with saturated brine (10 ml×2), dried with anhydrous sodium sulfate, filtered, and concentrated under reduced pressure. The residue was isolated by high-performance liquid chromatography (formic acid condition) to give the compound 3.

$^1$H NMR (400 MHz, CDCl$_3$) δ 8.63 (d, 1H, J=1.6 Hz), 8.6-8.6 (m, 1H), 7.7-7.7 (m, 1H), 7.5-7.6 (m, 4H), 7.44 (d, 1H, J=4.8 Hz), 7.35 (s, 1H), 6.4-6.7 (m, 1H), 4.90 (d, 2H, J=6.0 Hz), 2.65 (s, 3H), 2.37 (s, 3H). MS-ESI Calculated [M+H]$^+$ 424, Found 424.

Example 4

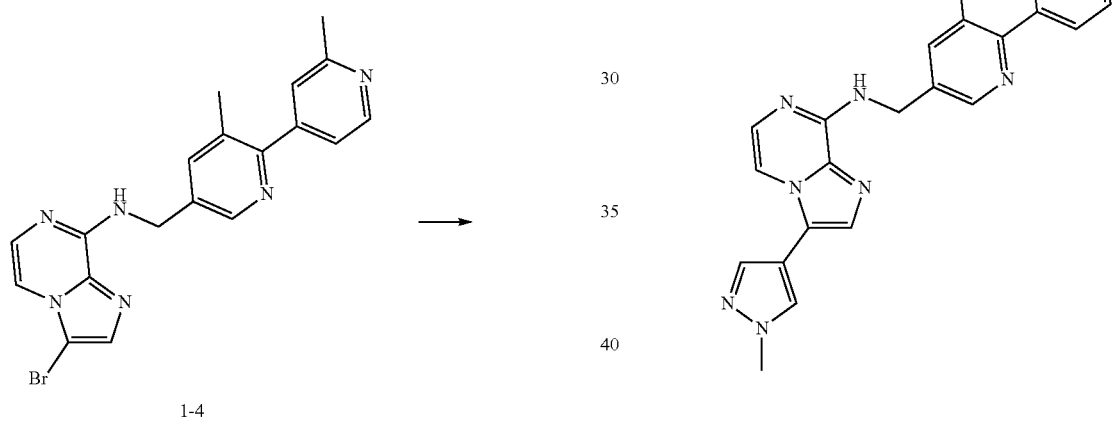

Route for Synthesis:

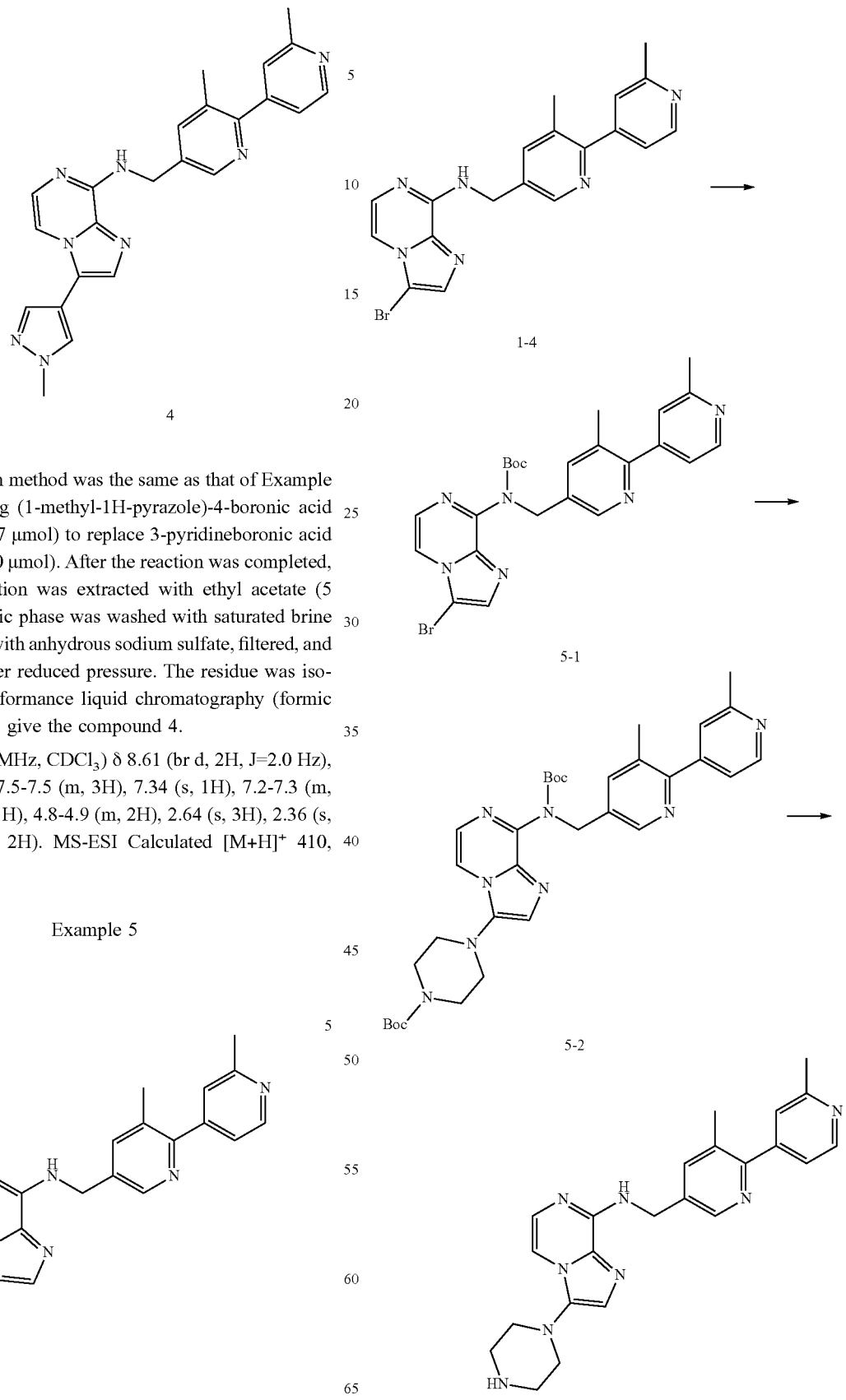

4

The preparation method was the same as that of Example 2, except of using (1-methyl-1H-pyrazole)-4-boronic acid (15.80 mg, 125.47 μmol) to replace 3-pyridineboronic acid (31.23 mg, 254.10 μmol). After the reaction was completed, the reaction solution was extracted with ethyl acetate (5 ml×3). The organic phase was washed with saturated brine (10 ml×2), dried with anhydrous sodium sulfate, filtered, and concentrated under reduced pressure. The residue was isolated by high-performance liquid chromatography (formic acid condition) to give the compound 4.

$^1$H NMR (400 MHz, CDCl$_3$) δ 8.61 (br d, 2H, J=2.0 Hz), 7.6-7.8 (m, 1H), 7.5-7.5 (m, 3H), 7.34 (s, 1H), 7.2-7.3 (m, 3H), 6.4-6.5 (m, 1H), 4.8-4.9 (m, 2H), 2.64 (s, 3H), 2.36 (s, 3H), 1.8-2.0 (m, 2H). MS-ESI Calculated [M+H]$^+$ 410, Found 410.

Example 5

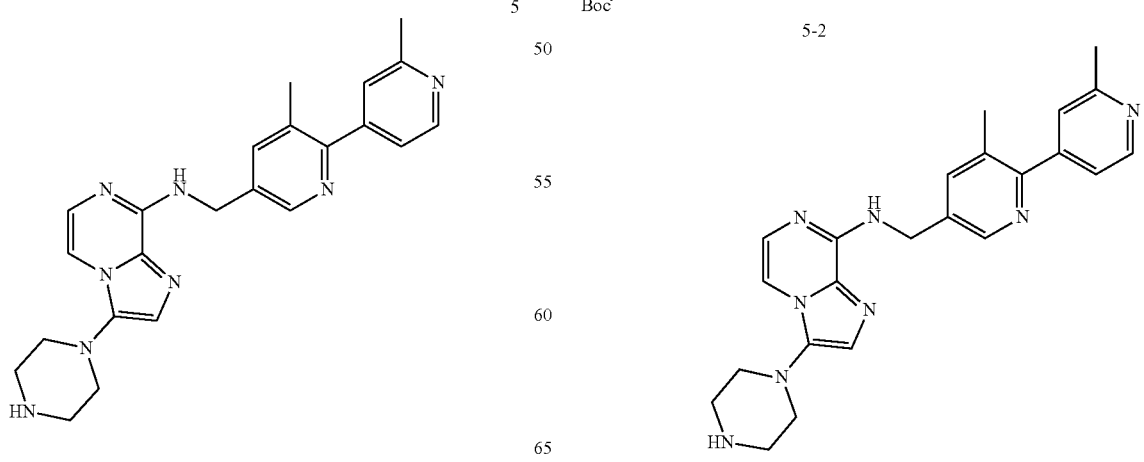

5

Example 6

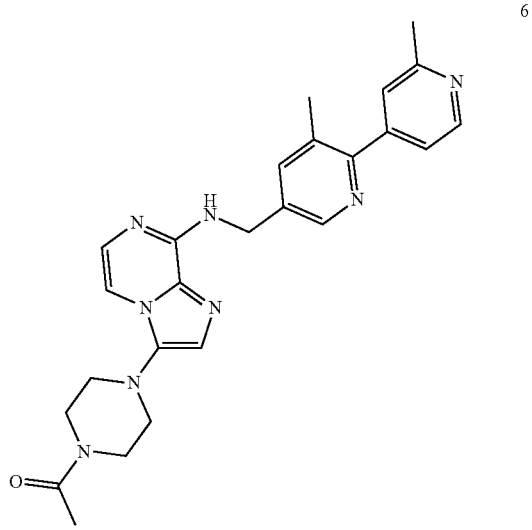 [SMILES: CC(=O)N1CCN(c2cnc3c(NCc4cnc(-c5ccnc(C)c5)c(C)c4)nccn23)CC1]

6

Route for Synthesis:

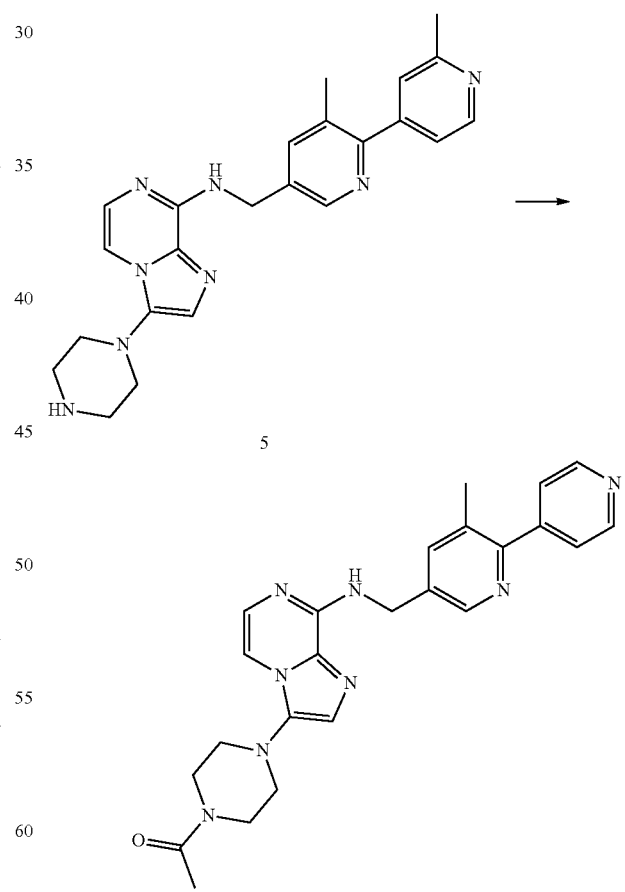

Step 1

At 0° C., compound 1-4 (1 g, 2.44 mmol) was dissolved in tetrahydrofuran (10 ml), and then a solution of lithium bis(trimethylsilyl)amide in tetrahydrofuran (1.0 M, 3.66 ml) was added. After stirring at 15° C. for 1 hour, di-tert-butyl dicarbonate (586.57 mg, 2.69 mmol, 617.44 ml) was added, and the mixture was stirred at 15° C. for another 15 hours. After the reaction was completed, the reaction solution was concentrated under reduced pressure. The residue was added into water (50 ml), and the mixture was extracted with ethyl acetate (30 ml×3). The organic phases were combined, dried with anhydrous sodium sulfate, filtered, and concentrated under reduced pressure. The residue was isolated by thin-layer chromatography to give compound 5-1.

MS-ESI Calculated $[M+H]^+$ 509, 511, Found 509, 511.

Step 2

After compound 5-1 (100 mg, 196.31 μmol) was dissolved in dioxane (2 ml), 1-Boc-piperazine (54.84 mg, 294.47 μmol), methanesulfonic acid (2-di-tert-butylphosphino-2,4,6-triisopropyl-1,1-biphenyl)(2-amino-1,1-biphenyl-2-yl)palladium(II) (15.59 mg, 19.63 μmol) and sodium tert-butoxide (56.60 mg, 588.93 μmol) were added. The reaction mixture was stirred at 110° C. in a nitrogen atmosphere for 16 hours. After the reaction was completed, the reaction solution was concentrated under reduced pressure water was added (30 ml), and the mixture was extracted with ethyl acetate (15 ml×3). The organic phases were combined, dried with anhydrous sodium sulfate, filtered, and concentrated under reduced pressure. The residue was isolated by thin-layer chromatography to give compound 5-2.

$^1$H NMR (400 MHz, CD$_3$OD) δ ppm 8.51 (br s, 2H), 7.82 (s, 1H), 7.54 (d, J=4.8 Hz, 1H), 7.42 (s, 1H), 7.35 (br d, J=5.0 Hz, 1H), 7.30 (d, J=4.8 Hz, 1H), 7.24 (s, 1H), 4.82 (s, 2H), 3.65 (br d, J=6.4 Hz, 4H), 2.90-3.11 (m, 4H), 2.60 (s, 3H), 2.32 (s, 3H), 1.49 (s, 9H). MS-ESI Calculated $[M+H]^+$ 515, Found 515.

Step 3

Compound 5-2 (80 mg, 130.14 μmol, 1 eq) was dissolved in ethyl acetate (2 ml), and then a solution of hydrogen chloride in ethyl acetate (4 M, 2 ml) was added. The mixture was reacted at 15° C. for 2 hours. After the reaction was completed, the reaction solution was concentrated under reduced pressure. The residue was isolated by high-performance liquid chromatography (alkaline condition) to give compound 5.

MS-ESI Calculated $[M+H]^+$ 415, Found 415. $^1$H NMR (400 MHz, CD$_3$OD) δ ppm 8.47-8.57 (m, 2H), 7.85 (s, 1H), 7.53 (d, J=4.8 Hz, 1H), 7.44 (s, 1H), 7.37 (d, J=5.1 Hz, 1H), 7.31 (d, J=4.8 Hz, 1H), 7.23 (s, 1H), 4.84 (br s, 2H), 3.06 (s, 8H), 2.62 (s, 3H), 2.35 (s, 3H). MS-ESI Calculated $[M+H]^+$ 415, Found 415.

Compound 5 (30 mg, 66.52 μmol) was dissolved in dichloromethane (2 ml), and then triethylamine (20.19 mg, 199.57 μmol, 27.78 ml) and acetic anhydride (7.47 mg, 73.18 μmol, 6.85 ml) were added. The reaction mixture was stirred at 10° C. for 16 hours. After the reaction was completed, the reaction solution was concentrated under reduced pressure. The residue was isolated by high-performance liquid chromatography (formic acid condition) to give compound 6.

$^1$H NMR (400 MHz, CD$_3$OD) δ ppm 8.45-8.59 (m, 2H), 7.82 (d, J=1.3 Hz, 1H), 7.57 (d, J=4.8 Hz, 1H), 7.41 (s, 1H), 7.35 (dd, J=5.3, 1.1 Hz, 1H), 7.32 (d, J=4.8 Hz, 1H), 7.25 (s, 1H), 4.59 (br s, 2H), 3.78 (dt, J=18.2, 5.1 Hz, 4H), 2.97-3.15 (m, 4H), 2.60 (s, 3H), 2.32 (s, 3H), 2.16 (s, 3H). MS-ESI Calculated [M+H]$^+$ 457, Found 457.

Example 7

-continued

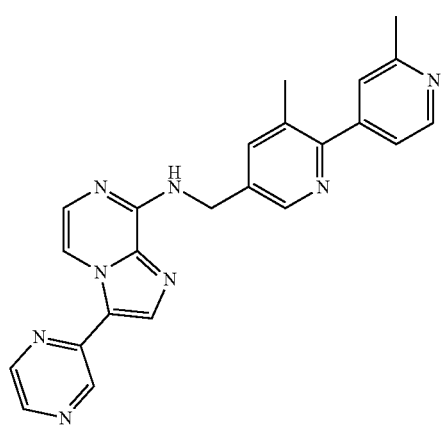

7

The preparation method was the same as that of Example 2, except of using 2-tributyltinylpyrazine (54.11 mg, 146.60 μmol) to replace 3-pyridineboronic acid (31.23 mg, 254.10 μmol). After the reaction was completed, the reaction solution was concentrated under reduced pressure. Water was added (30 ml), and the mixture was extracted with ethyl acetate (15 ml×3). The organic phases were combined, dried with anhydrous sodium sulfate (5 g), filtered, and concentrated under reduced pressure. The residue was isolated by thin-layer chromatography, and then isolated by high-performance liquid chromatography (formic acid condition) to give compound 7. MS-ESI Calculated [M+H]$^+$ 409, Found 409.

Example 8

Route for Synthesis:

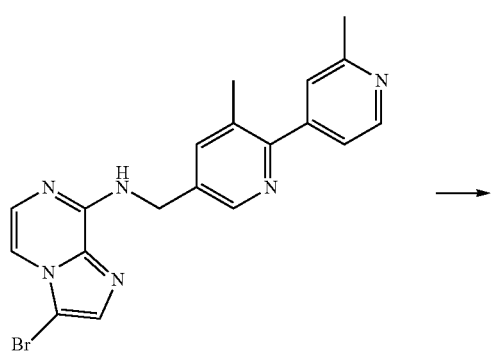

1-4

8

Example 9

Route for Synthesis:

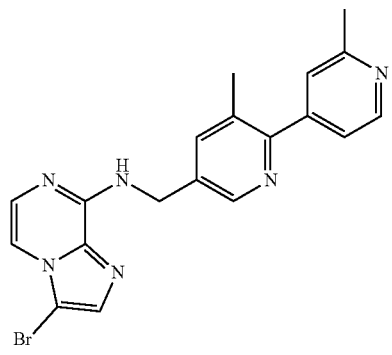

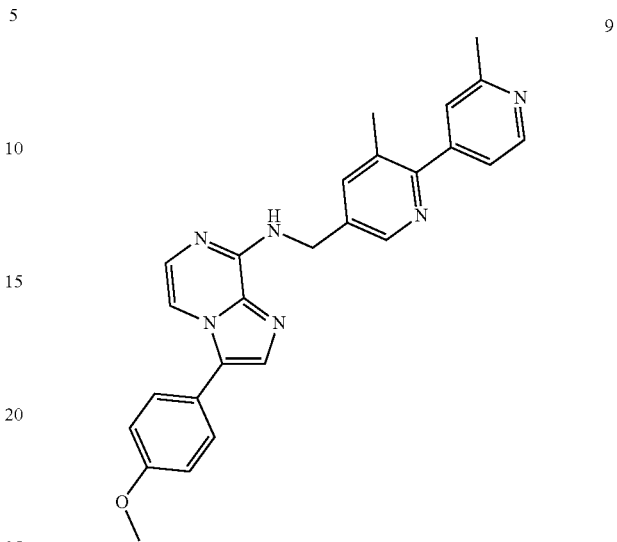

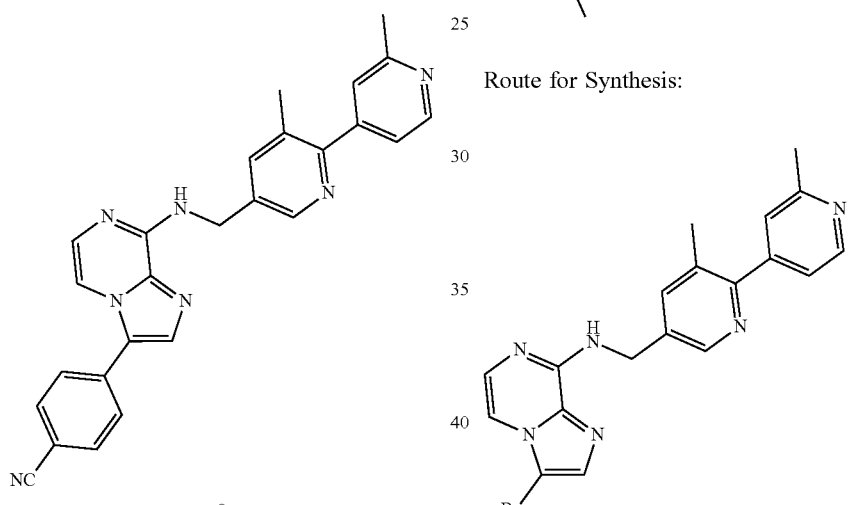

Route for Synthesis:

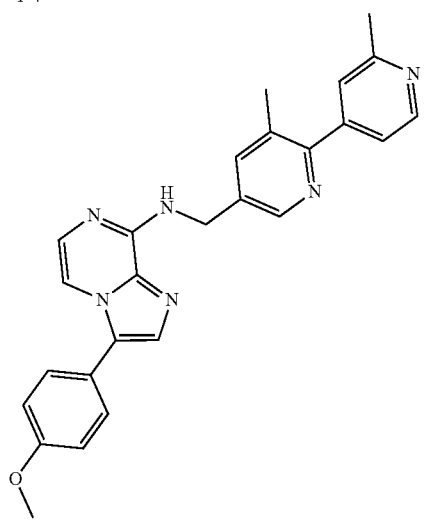

Step 1

The preparation method was the same as that of Example 2, except of using 4-cyanophenylboronic acid (43.08 mg, 293.20 μmol) to replace 3-pyridineboronic acid (31.23 mg, 254.10 μmol). After the reaction was completed, the reaction mixture was diluted with water (15 ml), and the mixture was extracted with ethyl acetate (10 ml×3). The organic phase was washed with saturated brine (10 ml×2), dried with anhydrous sodium sulfate, filtered, and concentrated under reduced pressure. The residue was purified with a silica gel plate, and then isolated by high-performance liquid chromatography (formic acid condition) to give compound 8.

$^1$H NMR (400 MHz, DMSO-$d_6$) δ 8.5-8.6 (m, 2H), 8.36 (s, 1H), 8.01 (d, 2H, J=8.3 Hz), 7.95 (s, 1H), 7.8-7.9 (m, 3H), 7.74 (d, 1H, J=1.1 Hz), 7.4-7.4 (m, 2H), 7.33 (d, 1H, J=5.1 Hz), 4.75 (d, 2H, J=6.2 Hz), 4.0-4.1 (m, 1H), 3.1-3.3 (m, 3H), 2.3-2.3 (m, 3H). MS-ESI Calculated [M+H]$^+$ 431, Found 431.

Step 1

The preparation method was the same as that of Example 2, except of using 4-methoxyphenylboronic acid (41.60 mg, 273.74 μmol) to replace 3-pyridineboronic acid (31.23 mg, 254.10 μmol). After the reaction was completed, the reaction mixture was diluted with water (10 ml), and the mixture was extracted with ethyl acetate (5 ml×3). The organic phase was washed with saturated brine (10 ml×2), dried with anhydrous sodium sulfate, filtered, and concentrated under reduced pressure. The residue was isolated by high-performance liquid chromatography (formic acid condition) to give the formate salt of compound 9. $^1$H NMR (DMSO-$d_6$, 400 MHz) δ 8.4-8.6 (m, 2H), 8.27 (s, 1H), 7.73 (s, 1H), 7.6-7.7 (m, 2H), 7.57 (d, 2H, J=8.8 Hz), 7.39 (s, 1H), 7.3-7.3 (m, 2H), 7.12 (d, 2H, J=8.8 Hz), 4.74 (br d, 2H, J=6.3 Hz), 3.83 (s, 3H), 2.52 (br s, 3H), 2.31 (s, 3H). MS-ESI Calculated [M+H]$^+$ 436, Found 436.

Example 10

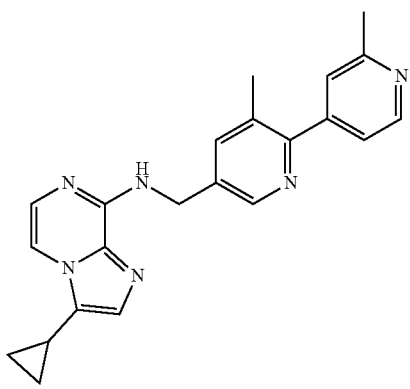

10

Route for Synthesis:

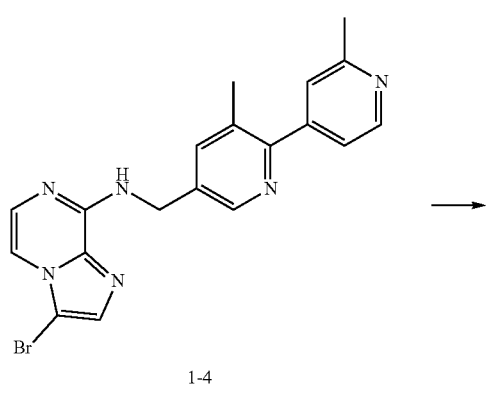

1-4

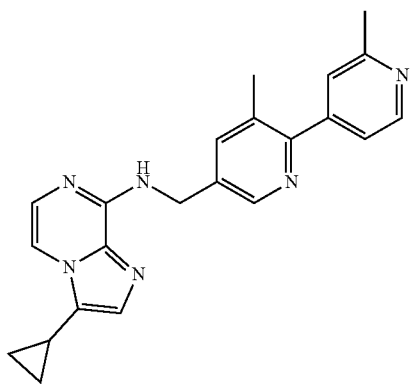

10

The preparation method was the same as that of Example 2, except of using cyclopropylboronic acid (41.97 mg, 488.66 μmol, 8.16 ml) to replace 3-pyridineboronic acid (31.23 mg, 254.10 μmol). The reaction solution was concentrated. The crude product was isolated successively by thin-layer chromatography plate and high-performance liquid chromatography (formic acid) to give compound 10. $^1$H NMR (400 MHz, CD$_3$OD) δ ppm 8.43-8.59 (m, 2H), 7.83 (s, 1H), 7.76 (d, J=4.8 Hz, 1H), 7.42 (s, 1H), 7.35 (d, J=4.8 Hz, 2H), 7.25 (s, 1H), 4.82 (br s, 2H), 2.60 (s, 3H), 2.33 (s, 3H), 1.88-2.01 (m, 1H), 1.01-1.13 (m, 2H), 0.68-0.79 (m, 2H). MS-ESI Calculated [M+H]$^+$ 371, Found 371.

Example 11

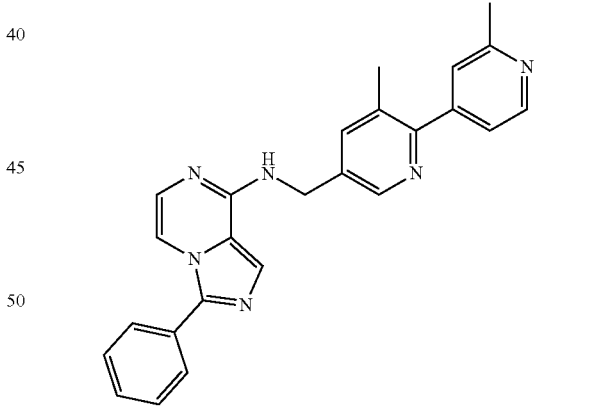

11

Route for Synthesis:

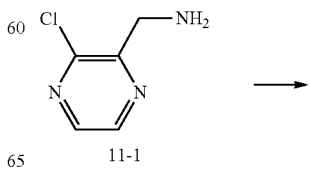

11-1

-continued

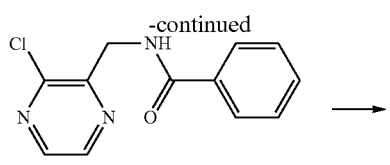

11-2

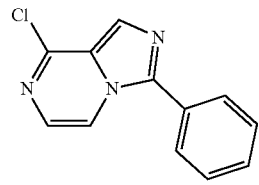

11-3

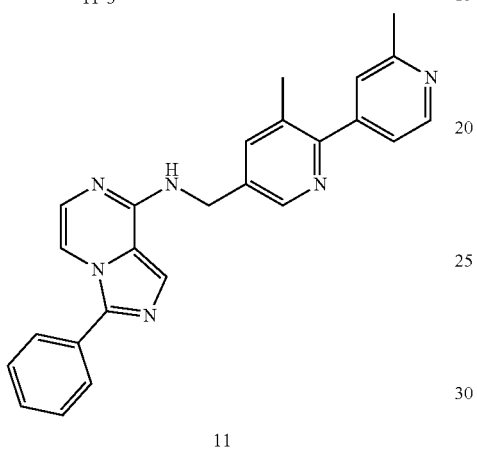

11

Step 1

Compound 11-1 (300 mg, 1.67 mmol), 4-dimethylaminopyridine (20.40 mg, 167.00 μmol), and diisopropylethylamine (1.08 g, 8.35 mmol, 1.45 ml) were added to dichloromethane (10 ml), and stirred at 15° C. for 15 minutes. Benzoyl chloride (258.22 mg, 1.84 mmol, 213.41 μl) was added and stirred for 16 hours. The residue was added into water (30 ml), and the mixture was extracted with dichloromethane (20 ml). The organic phase was dried with anhydrous sodium sulfate, filtered, and concentrated to give compound 11-2. The crude product was directly used in the next reaction.

Step 2

Compound 11-2 (480 mg, 1.94 mmol, 1 eq) was dissolved in acetonitrile (20 ml), and phosphorus oxychloride (1.49 g, 9.69 mmol, 900.47 ml, 5 eq) and N,N-dimethylformamide (7.08 mg, 96.90 μmol, 7.46 μl, 0.05 eq) were added at 10° C. The mixture was stirred at 75° C. under nitrogen protection for 16 hours. The reaction solution was quenched with water (50 ml), and the mixture was extracted with ethyl acetate (50 ml). The organic phase was dried with anhydrous sodium sulfate, filtered, and concentrated to give compound 11-3.

Step 3

Compound 11-3 (100 mg, 435.42 μmol) was dissolved in N-methylpyrrolidone (1 ml), and (2',3-dimethyl-[2,4'-bipyridyl]-5-yl)methylamine (140.49 mg, 435.42 μmol, 3 HCl) and potassium carbonate (300.89 mg, 2.18 mmol) were added. The mixture was stirred at 100° C. for 16 hours. The mixture was added into water (50 ml), and the mixture was extracted with ethyl acetate (50 ml). The organic phase was washed once with water (50 ml) and once with saturated brine (50 ml), dried with anhydrous sodium sulfate, filtered and concentrated. The crude product was isolated by high-performance liquid chromatography (alkaline) to give compound 11.

$^1$H NMR (400 MHz, CD$_3$OD) δ ppm 8.46-8.56 (m, 2H), 7.92 (d, J=0.6 Hz, 1H), 7.83 (d, J=1.3 Hz, 1H), 7.74-7.80 (m, 2H), 7.67 (d, J=5.1 Hz, 1H), 7.56-7.62 (m, 2H), 7.48-7.55 (m, 1H), 7.42 (s, 1H), 7.35 (d, J=5.1 Hz, 1H), 7.10 (d, J=5.3 Hz, 1H), 4.82 (s, 2H), 2.60 (s, 3H), 2.34 (s, 3H). MS-ESI Calculated [M+H]$^+$ 407, Found 407.

Example 12

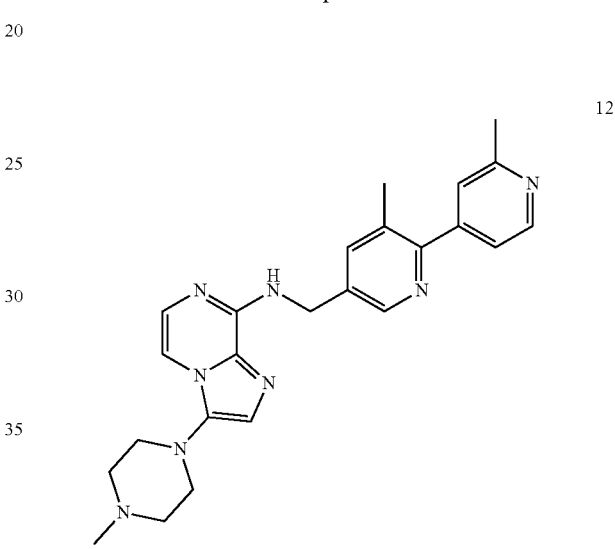

12

Route for Synthesis:

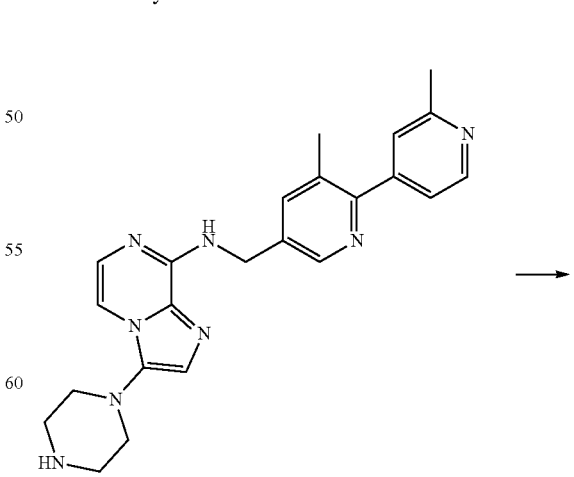

5

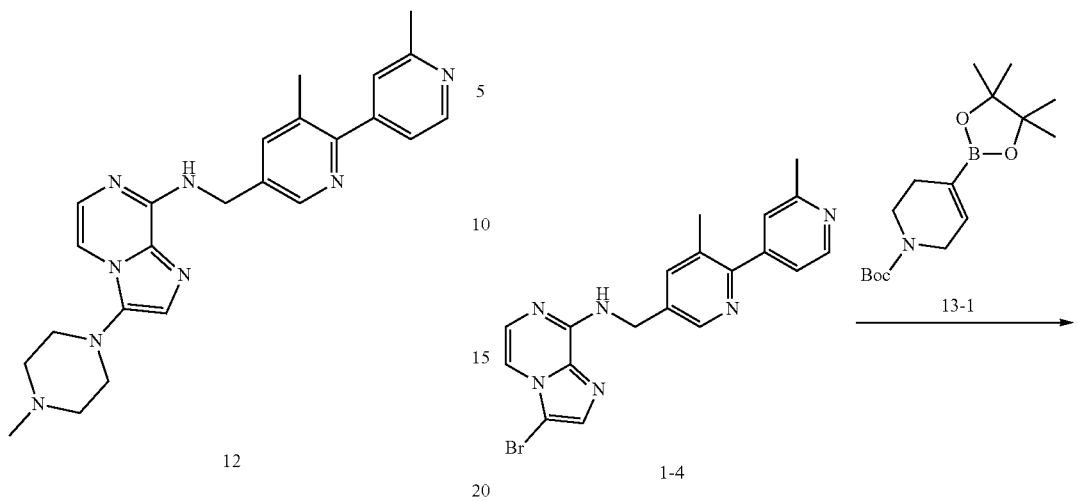

Compound 5 (30 mg, 66.52 μmol, 1 eq) was dissolved in methanol (2 ml), and then formaldehyde (300.56 mg, 10.01 mmol, 275.74 ml), sodium cyanoborohydride (6.27 mg, 99.79 μmol), and N,N-diisopropylethylamine (8.60 mg, 66.52 μmol, 11.59 ml) were added in sequence. The reaction mixture was stirred at 10° C. for 16 hours. After the reaction was completed, the reaction solution was concentrated under reduced pressure. The residue was isolated by high-performance liquid chromatography (formic acid condition) to give the formate salt of compound 12.

$^1$H NMR (400 MHz, CD$_3$OD) δ ppm 8.50 (d, J=2.8 Hz, 2H), 8.36 (br s, 1H), 7.82 (d, J=1.2 Hz, 1H), 7.54 (d, J=4.8 Hz, 1H), 7.42 (s, 1H), 7.35 (d, J=5.1 Hz, 1H), 7.27-7.33 (m, 2H), 4.82 (s, 2H), 3.27 (br d, J=4.5 Hz, 4H), 3.22 (br d, J=3.3 Hz, 4H), 2.77 (s, 3H), 2.60 (s, 3H), 2.33 (s, 3H). MS-ESI Calculated [M+H]$^+$ 429, Found 429.

Example 13

Route for Synthesis:

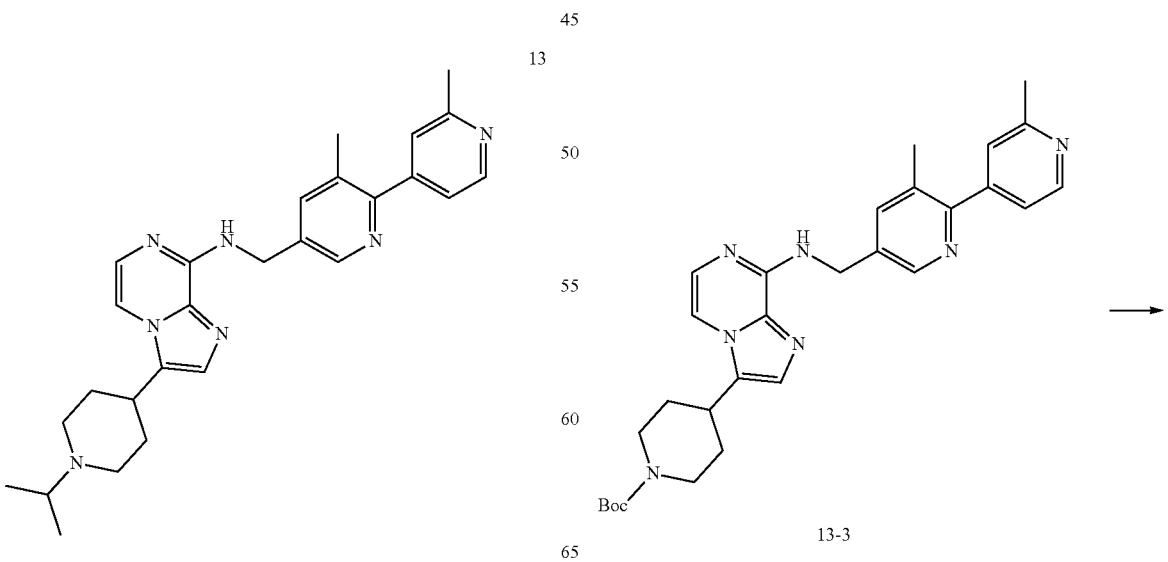

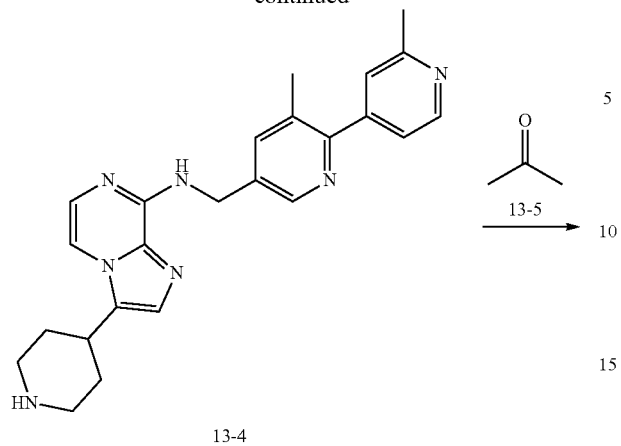

13-4

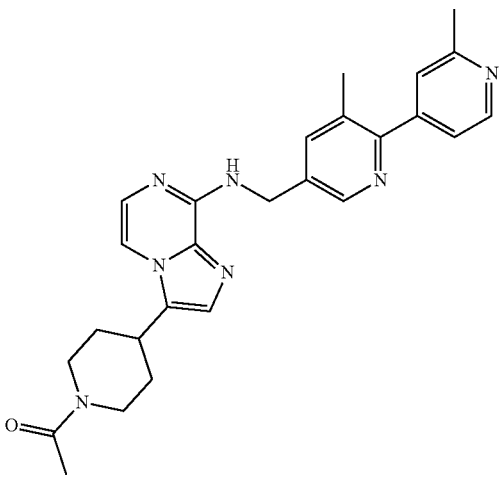

13

Step 1

Compound 1-4 (400 mg, 977.32 μmol) and compound 13-1 (362.63 mg, 1.17 mmol) were dissolved in dioxane (4 ml), and then 1,1'-bis(diphenylphosphino)ferrocene palladium dichloride (71.51 mg, 97.73 μmol) and potassium carbonate (405.22 mg, 2.93 mmol) were added. The air in the solution was replaced 3 times with nitrogen, and the reaction solution was stirred at 80° C. under nitrogen protection for 16 hours. After the reaction was completed, the reaction solution was diluted with 40 ml of water, and extracted with 90 ml of ethyl acetate (30 ml×3). The organic phase was washed with 60 ml of saturated brine (30 ml×2), dried with anhydrous sodium sulfate, filtered and concentrated. The crude product was isolated by high-performance liquid chromatography (formic acid condition) to give compound 13-2. MS-ESI Calculated [M+H]$^+$ 512, Found 512.

Step 2

Compound 13-2 (100 mg, 195.46 μmol) was dissolved in methanol (2 ml), and palladium on carbon (40 mg, 39.09 μmol, 60% purity) was added under nitrogen protection. The mixture was stirred at 25° C. for 16 hours. After the reaction was completed, the reaction mixture was filtered and concentrated to give intermediate 13-3.

MS-ESI Calculated [M+H]$^+$ 514, Found 514.

Step 3

Intermediate 13-3 (100 mg, 194.69 μmol) was dissolved in methanol (2 ml), and a solution of hydrochloric acid in methanol (0.25 ml, 4 mol/L) was added. The mixture was stirred at 25° C. for 1 hour. After the reaction was completed, the reaction solution was concentrated to give intermediate 13-4.

MS-ESI Calculated [M+H]$^+$ 414, Found 414.

Step 4

Intermediate 13-4 (30 mg, 72.55 μmol) and intermediate 13-5 (42.14 mg, 725.48 μmol, 53.34 μl) were dissolved in methanol (1 ml), and then ethyl acetate (639.19 μg, 7.25 μmol, 0.71 μl) was added. The mixture was stirred at 25° C. for 0.5 hours. Sodium cyanoborohydride (4.56 mg, 72.55 μmol) was then added and the mixture was stirred at 25° C. for 2.5 hours. After the reaction was completed, the reaction solution was concentrated. The crude product was isolated by high-performance liquid chromatography (formic acid condition) to give the formate salt of compound 13.

$^1$H NMR (400 MHz, CDCl$_3$) δ=8.45-8.58 (m, 2H), 8.40 (s, 1H), 7.58 (d, J=1.5 Hz, 1H), 7.31-7.35 (m, 1H), 7.28-7.31 (m, 1H), 7.26 (s, 1H), 7.24 (s, 1H), 7.16 (dd, J=1.1, 5.1 Hz, 1H), 6.66 (s, 1H), 4.77 (d, J=5.9 Hz, 2H), 3.31-3.22 (m, 2H), 2.92 (br t, J=11.3 Hz, 1H), 2.62-2.74 (m, 2H), 2.55 (s, 3H), 2.26 (s, 5H), 2.12 (br d, J=14.4 Hz, 2H), 1.23 (d, J=6.6 Hz, 6H), 1.17 (s, 1H). MS-ESI Calculated [M+H]$^+$ 456, Found 456.

Example 14

14

Route for Synthesis:

Example 15

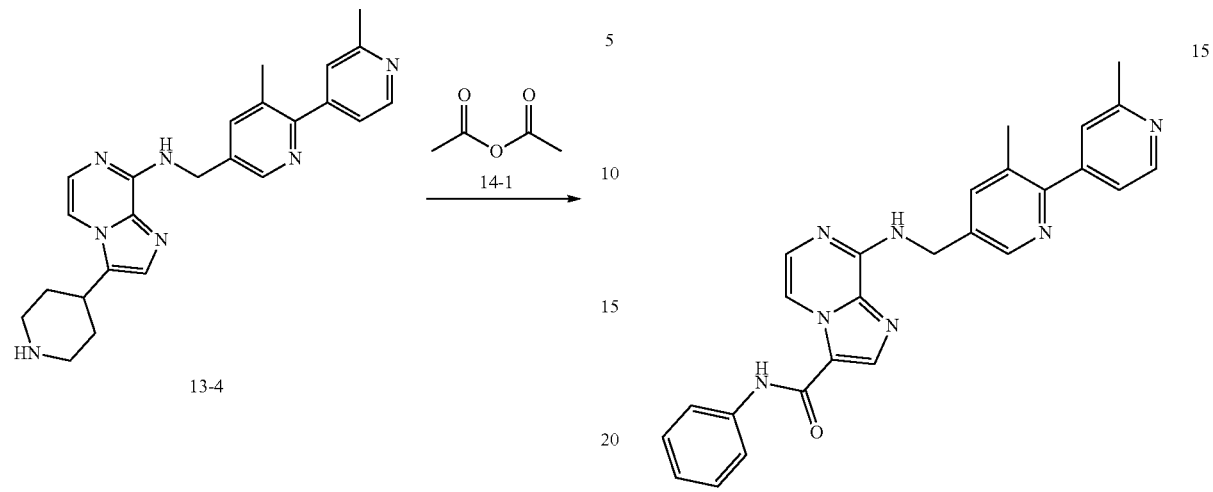

13-4

14

Route for Synthesis:

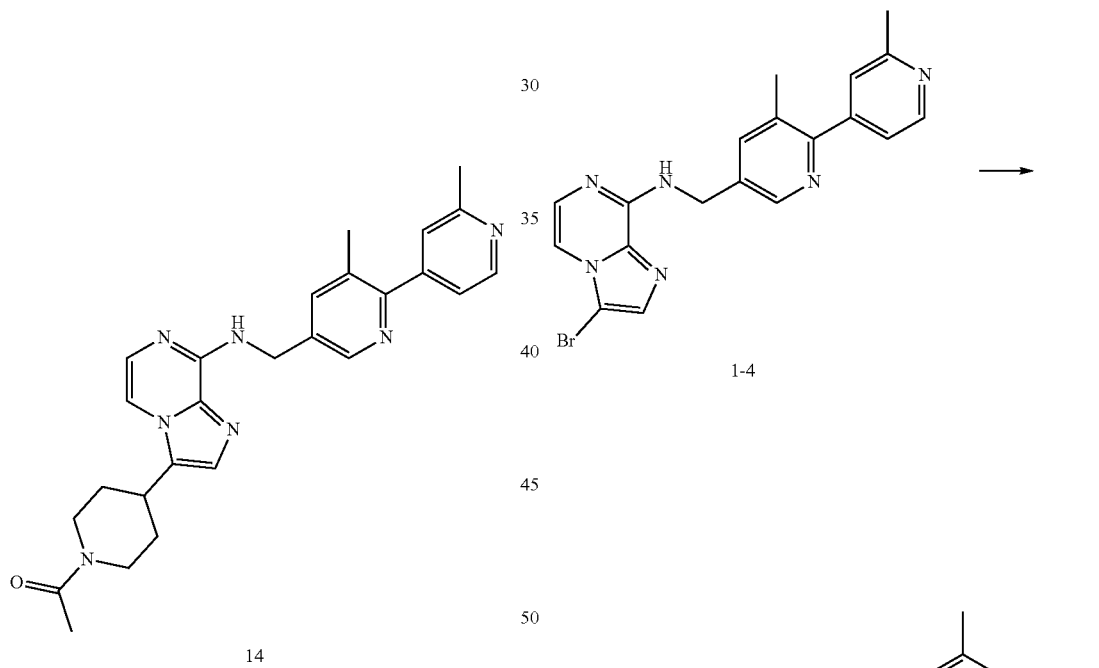

1-4

15-1

Compound 13-4 (30 mg, 72.55 μmol) was dissolved in dichloromethane (1 ml), and then compound 14-1 (8.72 mg, 87.06 μmol, 8.94 μl) was added. The mixture was stirred at 25° C. for 3 hours. After the reaction was completed, the reaction solution was concentrated. The crude product was isolated by high-performance liquid chromatography (formic acid condition) to give compound 14. $^1$H NMR (400 MHz, CD$_3$OD) δ ppm 8.42-8.68 (m, 2H), 7.85 (s, 1H), 7.74 (d, J=4.9 Hz, 1H), 7.44 (s, 1H), 7.30-7.41 (m, 3H), 4.68 (br d, J=13.4 Hz, 2H), 4.08 (br d, J=13.8 Hz, 1H), 3.33-3.44 (m, 2H), 3.22-3.32 (m, 2H), 2.78-2.97 (m, 1H), 2.62 (s, 3H), 2.35 (s, 3H), 2.17 (s, 5H), 1.54-1.86 (m, 2H). MS-ESI Calculated [M+H]$^+$ 456, Found 456.

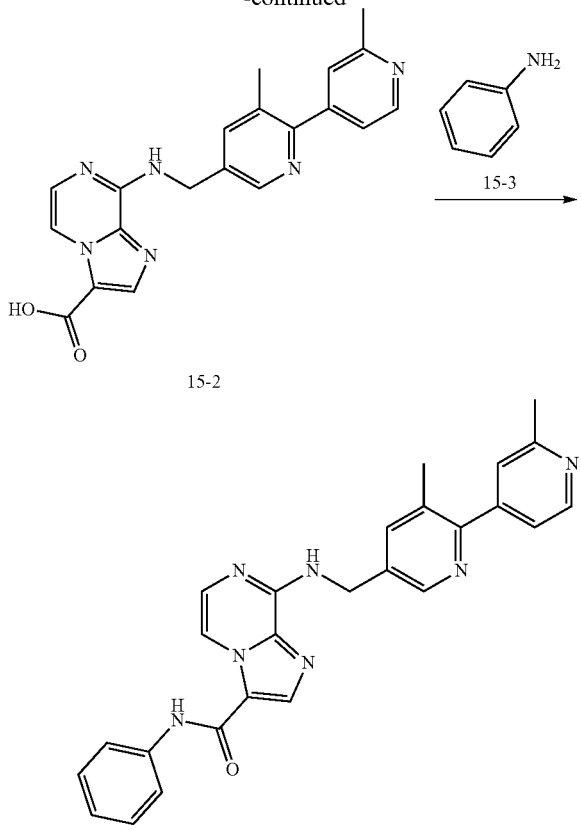

N,N-dimethylformamide (5 ml), and O-(7-azabenzotriazol-1-yl)-N,N,N,N-tetramethylurea hexafluorophosphate (60.94 mg, 160.26 μmol) and N,N-diisopropylethylamine (34.52 mg, 267.10 μmol, 46.52 μl) were added. The mixture was stirred at 25° C. for 2 hours. After the reaction was completed, water (10 ml) was added to the reaction solution, and the mixture was extracted with ethyl acetate (10 ml×3). The organic phase was washed with brine (10 ml×2), dried with anhydrous sodium sulfate, filtered and concentrated. The crude product was isolated by high-performance liquid chromatography (formic acid condition) to give the formate salt of compound 15. $^1$H NMR (400 MHz, CD$_3$OD) δ=8.68 (d, J=4.8 Hz, 1H), 8.46-8.59 (m, 2H), 8.38 (s, 1H), 7.88 (d, J=1.4 Hz, 1H), 7.65-7.78 (m, 2H), 7.50 (d, J=4.8 Hz, 1H), 7.46 (s, 1H), 7.40-7.43 (m, 1H), 7.37-7.40 (m, 2H), 7.31 (s, 1H), 7.15-7.22 (m, 1H), 4.88 (br s, 2H), 2.63 (s, 3H), 2.36 (s, 3H). MS-ESI Calculated [M+H]$^+$ 450, Found 450.

Example 16

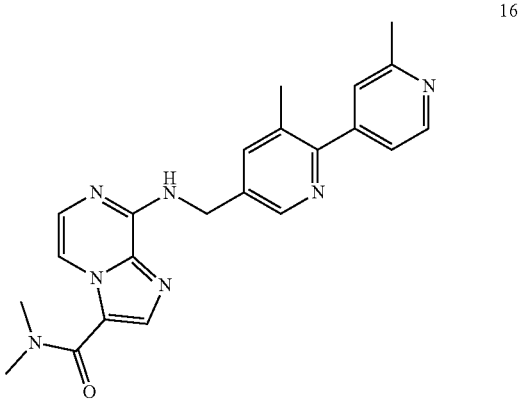 [SMILES: Cc1cc(-c2ncc(CNc3nccn4c(C(=O)N(C)C)cnc34)cc2C)ccn1]

Route for Synthesis:

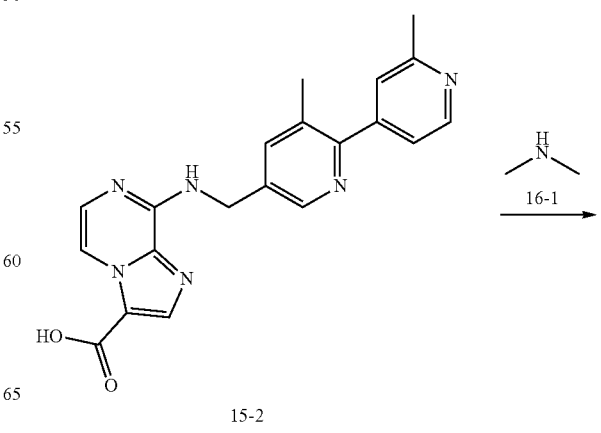

Step 1

Compound 1-4 (300 mg, 732.99 μmol) was dissolved in a mixed solution of methanol (30 ml) and N,N-dimethylformamide (2 ml), and then 1,1'-bis(diphenylphosphino)ferrocene palladium dichloride (53.63 mg, 73.30 μmol) and triethylamine (222.51 mg, 2.20 mmol, 306.07 μl) were added. The air in the reaction solution was replaced with nitrogen, and then the nitrogen in the reaction device was replaced several times with carbon monoxide. The reaction solution was stirred at 80° C. in a CO atmosphere for 16 hours. After the reaction was completed, the reaction mixture was filtered and concentrated. The crude product was purified by silica gel thin-layer chromatography to give intermediate 15-1. MS-ESI Calculated [M+H]$^+$ 388, Found 388.

Step 2

Intermediate 15-1 (250 mg, 643.63 μmol) was dissolved in methanol (3 ml) and water (1 ml), and lithium hydroxide monohydrate (40.51 mg, 965.45 μmol) was added. The mixture was stirred at 25° C. for 3 hours. After the reaction was completed, the reaction solution was adjusted to pH 7 with HCl (1M aqueous solution), and then concentrated to give crude product 15-2. MS-ESI Calculated [M+H]$^+$ 374, Found 374.

Step 3

Intermediate 15-2 (50 mg, 133.55 μmol) and compound 15-3 (12.44 mg, 133.55 μmol, 12.19 μl) were dissolved in

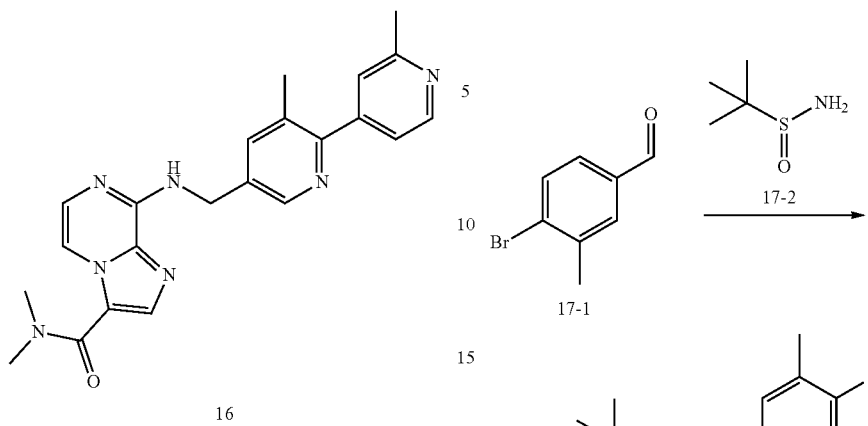

Intermediate 15-2 (50 mg, 133.55 μmol) and compound 16-1 (21.78 mg, 267.10 μmol) were dissolved in N,N-dimethylformamide (5 ml), and O-(7-azabenzotriazol-1-yl)-N,N,N,N-tetramethylurea hexafluorophosphate (60.94 mg, 160.26 μmol, 1.2 equivalent) and N,N-diisopropylethylamine (34.52 mg, 267.10 μmol, 46.52 μl) were added. The mixture was stirred at 25° C. for 2 hours. After the reaction was completed, water (10 ml) was added to the reaction solution, and the mixture was extracted with 30 ml of ethyl acetate (10 ml×3). The organic phase was washed with 20 ml of brine (10 ml×2), dried with anhydrous sodium sulfate, filtered and concentrated. The crude product was isolated by high-performance liquid chromatography (formic acid condition) to give compound 16. $^1$H NMR (400 MHz, CD$_3$OD) δ ppm 8.41-8.70 (m, 2H), 8.15 (d, J=4.8 Hz, 1H), 7.97 (s, 1H), 7.86 (d, J=1.4 Hz, 1H), 7.41-7.50 (m, 2H), 7.37 (dd, J=1.1, 5.3 Hz, 1H), 4.86 (s, 2H), 2.97-3.32 (m, 6H), 2.62 (s, 3H), 2.35 (s, 3H); MS-ESI Calculated [M+H]$^+$ 402, Found 402.

Example 17

Route for Synthesis:

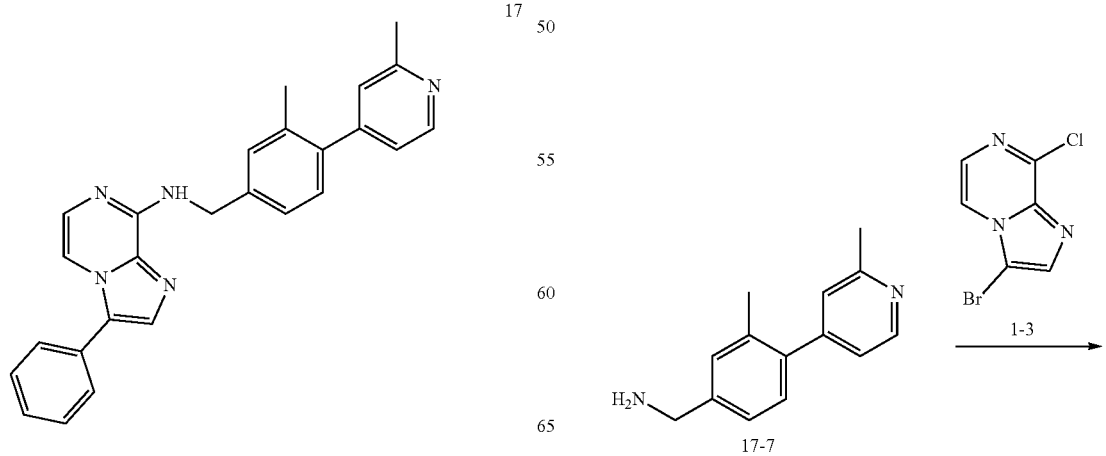

-continued

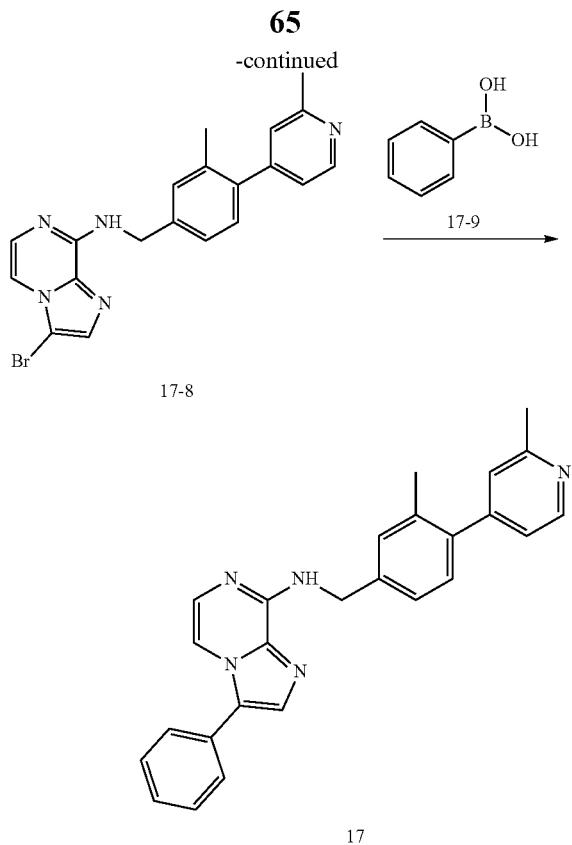

Step 1

Compound 17-1 (1.00 g, 5.02 mmol, 1 equivalent) and compound 17-2 (913 mg, 7.53 mmol) were dissolved in tetrahydrofuran (20 ml). Anhydrous copper sulfate (1.76 g, 11.0 mmol, 1.69 ml) was added to the reaction solution, and the mixture was stirred at 70° C. for 12 hours. After the reaction was completed, the reaction mixture was filtered and the filtrate was concentrated under reduced pressure to give compound 17-3.

MS-ESI Calculated [M+H]$^+$ 302, Found 302.

Step 2

Compound 17-3 (1.50 g, 4.53 mmol) was dissolved in methanol (20 ml). Sodium borohydride (291 mg, 7.70 mmol) was slowly added to the reaction solution at 0° C., and the mixture was stirred at 25° C. under nitrogen protection for 5 hours. After the reaction was completed, the reaction mixture was diluted with water (50 ml) and then extracted with ethyl acetate (30 ml×3). The combined organic phase was washed with saturated brine (40 ml×2), dried with anhydrous sodium sulfate, filtered, and concentrated under reduced pressure. The residue was isolated by column chromatography to give compound 17-4. $^1$HNMR (400 MHz, CDCl$_3$) δ ppm 7.49 (, d, J=8.07 Hz, 1H), 7.21 (d, J=1.71 Hz, 1H), 7.03 (dd, J=8.13, 1.90 Hz, 1H), 4.12-4.34 (m, 2H), 3.41-3.53 (m, 1H), 2.39 (s, 3H), 1.24 (s, 9H); MS-ESI Calculated [M+H]$^+$ 304, 306, Found 304, 306.

Step 3

Compound 17-4 (1.00 g, 3.05 mmol) and 17-5 (459 mg, 3.35 mmol) were dissolved in 1,4-dioxane (20 ml) and water (2 ml). Cesium carbonate (2.98 g, 9.15 mmol) and 1,1'-bis (diphenylphosphino)ferrocene palladium dichloride (223 mg, 305 μmol) were added to the reaction solution under nitrogen protection, and stirred at 100° C. for 12 hours. After the reaction was completed, the reaction mixture was filtered, and the filtrate was concentrated under reduced pressure. The residue was isolated by column chromatography to give compound 17-6. $^1$H NMR (400 MHz, CDCl$_3$) δ ppm 8.53 (d, J=5.14 Hz, 1H), 7.26 (s, 1H), 7.25 (s, 1H), 7.15-7.20 (m, 1H), 7.11 (s, 1H), 7.06 (d, J=5.01 Hz, 1H), 4.36-4.43 (m, 1H), 4.25-4.33 (m, 1H), 3.47-3.57 (m, 1H), 2.61 (s, 3H), 2.28 (s, 3H), 1.27 (s, 9H). MS-ESI Calculated [M+H]$^+$ 317, Found 317.

Step 4

Compound 17-6 (0.890 g, 2.76 mmol) was dissolved in ethyl acetate (10 ml). Hydrochloric acid/ethyl acetate (4 mol, 5 ml) was added to the reaction solution, and the mixture was stirred at 25° C. for 2 hours. After the reaction was completed, the reaction mixture was concentrated under reduced pressure to give a residue, i.e., compound 17-7.

MS-ESI Calculated [M+H]$^+$ 213, Found 213.

Step 5

Compound 17-7 (0.600 g, 2.11 mmol, HCl) and compound 1-3 (416 mg, 1.79 mmol) were dissolved in N-methylpyrrolidone (10 ml). N,N-diisopropylethylamine (1.09 g, 8.43 mmol, 1.47 ml) was added to the reaction solution, and the mixture was stirred at 130° C. for 4 hours. After the reaction was completed, the reaction mixture was diluted with water (100 ml) and then extracted with ethyl acetate (30 ml×3). The combined organic phase was washed with saturated brine (40 ml×3), dried with anhydrous sodium sulfate, filtered, and concentrated under reduced pressure. The residue was purified by thin-layer chromatography to give compound 17-8.

$^1$HNMR (400 MHz, CDCl$_3$) δ ppm 8.52 (s, 1H, br), 7.49 (d, J=5.26 Hz, 2H, br), 7.45 (s, 1H, br), 7.31 (s, 1H, br), 7.17 (d, J=7.46 Hz, 1H, br), 7.10 (s, 1H), 7.05 (s, 1H, br), 6.35 (s, 1H, br), 4.82 (d, J=5.14 Hz, 2H, br), 2.61 (s, 3H), 2.26 (s, 3H). MS-ESI Calculated [M+H]$^+$ 410, Found 410.

Step 6

Compound 17-8 (50.0 mg, 121 μmol), compound 17-9 (16.2 mg, 133 μmol), 1,1'-bis(diphenylphosphino)ferrocene palladium dichloride (8.86 mg, 12.1 μmol), and cesium carbonate (118 mg, 363 μmol) were dissolved in dioxane (3 ml) and water (0.2 ml), and reacted at 90° C. under nitrogen protection for 12 hours. After the reaction was completed, the reaction mixture was diluted with water (30 ml) and then extracted with ethyl acetate (20 ml×3). The combined organic phase was washed with saturated brine (20 ml×4), dried with anhydrous sodium sulfate, filtered, and concentrated under reduced pressure to give a residue, which was purified by thin-layer chromatography (petroleum ether: ethyl acetate=1:1), and then isolated by high-performance liquid chromatography (formic acid condition) to give compound 17.

$^1$HNMR (400 MHz, CDCl$_3$) δ ppm 8.45 (d, J=5.14 Hz, 1H), 7.56 (d, J=4.77 Hz, 1H), 7.49-7.51 (m, 1H), 7.48 (d, J=1.96 Hz, 2H), 7.43-7.46 (m, 1H), 7.36-7.41 (m, 1H), 7.34 (d, J=4.77 Hz, 1H), 7.22-7.29 (m, 2H), 7.10 (d, J=7.82 Hz, 1H), 7.04 (s, 1H), 6.99 (dd, J=5.14, 1.22 Hz, 1H), 6.36 (s, 1H, br), 4.77 (d, J=5.87 Hz, 2H), 2.54 (s, 3H), 2.20 (s, 3H). MS-ESI Calculated [M+H]⁺ 406, Found 406.

Example 18

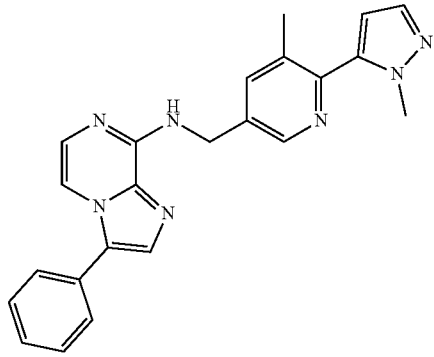

Route for Synthesis:

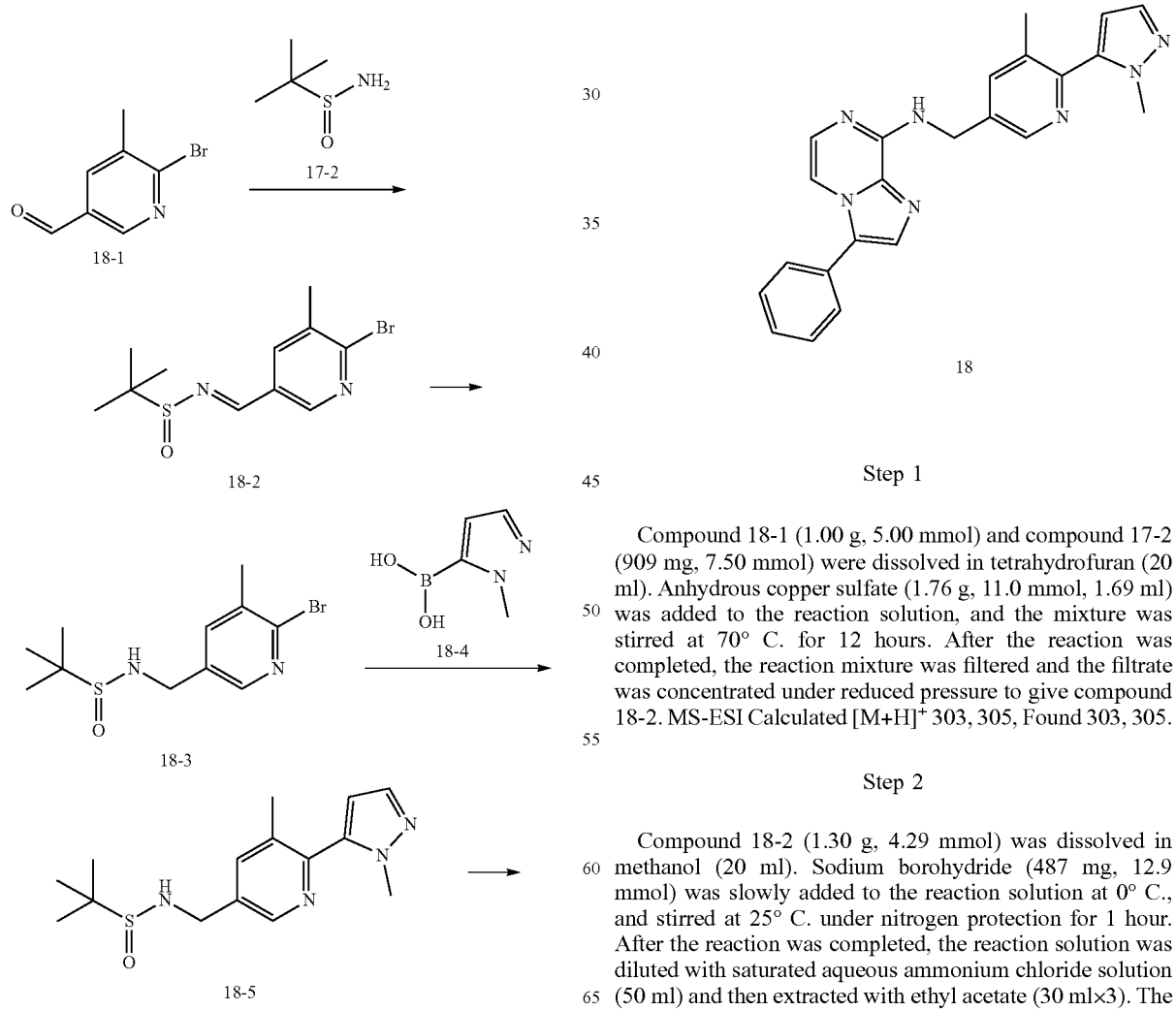

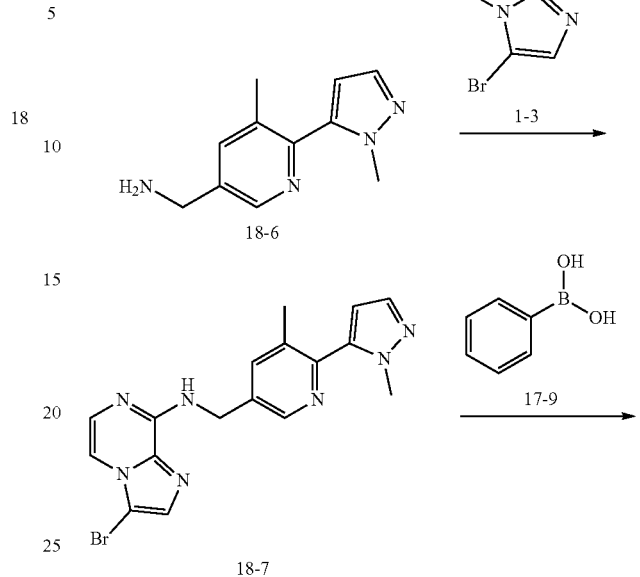

Step 1

Compound 18-1 (1.00 g, 5.00 mmol) and compound 17-2 (909 mg, 7.50 mmol) were dissolved in tetrahydrofuran (20 ml). Anhydrous copper sulfate (1.76 g, 11.0 mmol, 1.69 ml) was added to the reaction solution, and the mixture was stirred at 70° C. for 12 hours. After the reaction was completed, the reaction mixture was filtered and the filtrate was concentrated under reduced pressure to give compound 18-2. MS-ESI Calculated [M+H]⁺ 303, 305, Found 303, 305.

Step 2

Compound 18-2 (1.30 g, 4.29 mmol) was dissolved in methanol (20 ml). Sodium borohydride (487 mg, 12.9 mmol) was slowly added to the reaction solution at 0° C., and stirred at 25° C. under nitrogen protection for 1 hour. After the reaction was completed, the reaction solution was diluted with saturated aqueous ammonium chloride solution (50 ml) and then extracted with ethyl acetate (30 ml×3). The combined organic phase was washed with saturated brine (40 ml×2), dried with anhydrous sodium sulfate, filtered, and concentrated under reduced pressure. The residue was compound 18-3. MS-ESI Calculated [M+H]⁺ 305, 307, Found 305, 307.

Step 3

Compound 18-3 (500 mg, 1.64 mmol) and compound 18-4 (310 mg, 2.46 mmol) were dissolved in N,N-dimethylformamide (20 ml). Potassium carbonate (679 mg, 4.91 mmol) and 1,1'-bis(diphenylphosphino)ferrocene palladium dichloride dichloromethane (134 mg, 164 μmol) were added to the reaction solution under nitrogen protection, and stirred at 60° C. for 12 hours. After the reaction was completed, the reaction mixture was filtered. The filtrate was diluted with water (50 ml) and then extracted with ethyl acetate (30 ml×3). The combined organic phase was washed with saturated brine (40 ml×1), dried with anhydrous sodium sulfate, filtered, and concentrated under reduced pressure. The residue was purified by thin-layer chromatography to give compound 18-5. MS-ESI Calculated [M+H]⁺ 307, Found 307.

Step 4

Compound 18-5 (0.250 g, 816 μmol) was dissolved in ethyl acetate (2 ml). Hydrochloric acid/ethyl acetate (4 mol, 2.08 ml) was added to the reaction solution, and the mixture was stirred at 25° C. for 2 hours. After the reaction was completed, the reaction mixture was concentrated under reduced pressure to give a residue, i.e., compound 18-6.
MS-ESI Calculated [M+H]⁺ 203, Found 203.

Step 5

Compound 18-6 (0.110 g, 470 μmol) and compound 1-3 (92.9 mg, 399 μmol) were dissolved in N-methylpyrrolidone (6 ml). N,N-diisopropylethylamine (243 mg, 1.88 mmol, 327 μl) was added to the reaction solution, and the mixture was stirred at 130° C. for 3 hours. After the reaction was completed, the reaction mixture was diluted with water (50 ml) and then extracted with ethyl acetate (15 ml×3). The combined organic phase was washed with saturated brine (20 ml×3), dried with anhydrous sodium sulfate, filtered, and concentrated under reduced pressure. The residue was purified by thin-layer chromatography to give compound 18-7.
MS-ESI Calculated [M+H]⁺ 400, Found 400.

Step 6

Compound 18-7 (0.110 g, 238 μmol), compound 17-9 (37.6 mg, 309 μmol), 1,1'-bis(diphenylphosphino)ferrocene palladium dichloride (17.4 mg, 23.8 μmol), and potassium carbonate (98.5 mg, 713 μmol) were dissolved in dioxane (4 ml) and water (0.2 ml), and reacted at 100° C. under nitrogen protection for 12 hours. After the reaction was completed, the reaction mixture was diluted with water (30 ml) and then extracted with ethyl acetate (20 ml×3). The combined organic phase was washed with saturated brine (20 ml×4), dried with anhydrous sodium sulfate, filtered, and concentrated under reduced pressure. The residue was purified by thin-layer chromatography and then high-performance liquid chromatography (formic acid condition) to give compound 18.
¹HNMR (400 MHz, CDCl₃) δ ppm 8.62 (d, J=1.71 Hz, 1H), 7.69 (d, J=1.47 Hz, 1H), 7.65 (d, J=4.89 Hz, 1H), 7.59 (s, 1H), 7.53-7.56 (m, 4H), 7.46-7.49 (m, 1H), 7.41 (d, J=4.77 Hz, 1H), 6.57 (br t, J=5.81 Hz, 1H), 6.37 (d, J=1.83 Hz, 1H), 4.89 (d, J=5.99 Hz, 2H), 3.88 (s, 3H), 2.31 (s, 3H).
MS-ESI Calculated [M+H]⁺ 396, Found 396.

Example 19

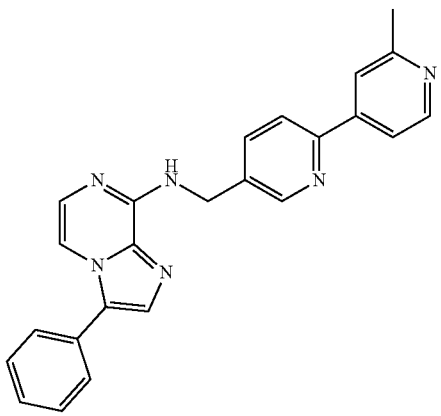

Route for Synthesis:

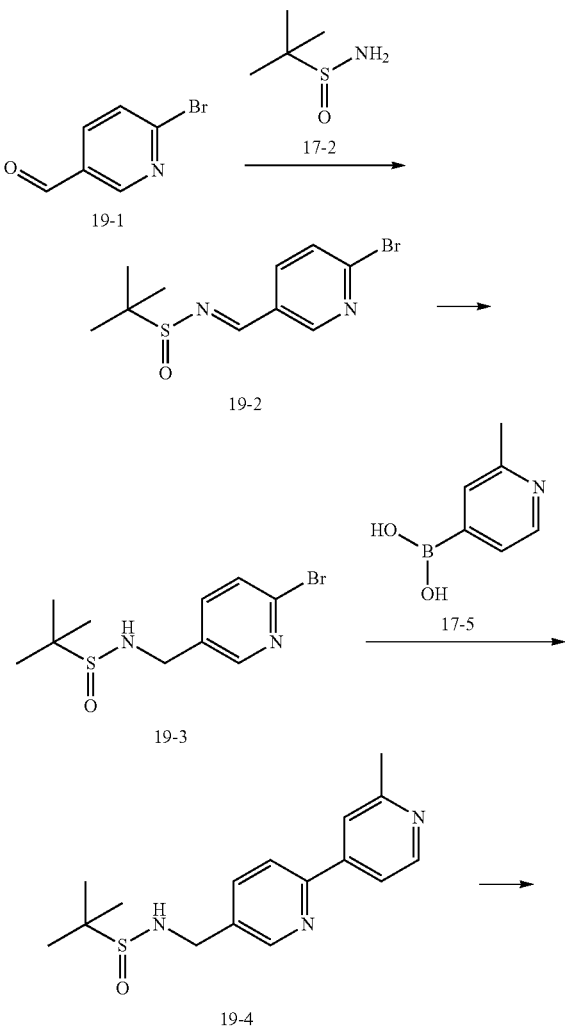

-continued

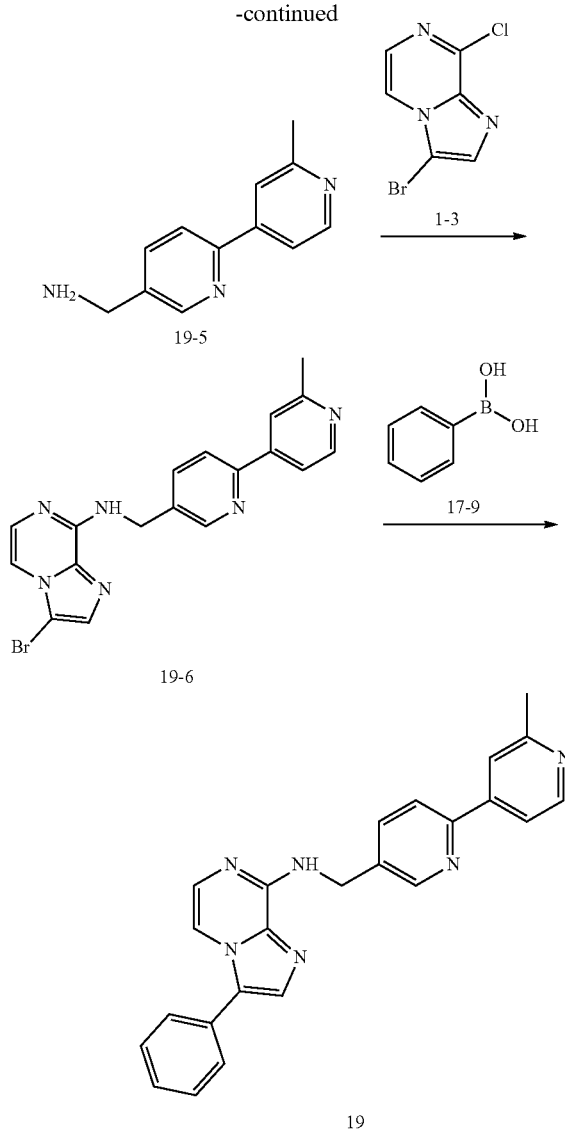

Step 1

Compound 19-1 (6.00 g, 32.3 mmol) and compound 17-2 (4.69 g, 38.7 mmol) were dissolved in tetrahydrofuran (25 ml). Anhydrous copper sulfate (11.3 g, 70.9 mmol, 10.9 ml) was added to the reaction solution, and the mixture was stirred at 70° C. for 12 hours. After the reaction was completed, the reaction mixture was filtered and the filtrate was concentrated under reduced pressure to give compound 19-2.

Step 2

Compound 19-2 (7.00 g, 24.2 mmol) was dissolved in methanol (60 ml). Sodium borohydride (1.56 g, 41.2 mmol) was slowly added to the reaction solution at 0° C., and stirred under nitrogen protection at 25° C. for 1.5 hours. After the reaction was completed, the reaction mixture was diluted with water (30 ml) and then extracted with ethyl acetate (20 ml×3). The combined organic phase was washed with saturated brine (20 ml×3), dried with anhydrous sodium sulfate, filtered, and concentrated under reduced pressure. The obtained residue was compound 19-3. $^1$HNMR (400 MHz, CDCl$_3$) δ ppm 8.35 (d, J=2.20 Hz, 1H), 7.58 (dd, J=8.19, 2.45 Hz, 1H), 7.48 (d, J=8.19 Hz, 1H), 4.30 (qd, J=14.35, 6.11 Hz, 2H), 1.24 (s, 9H). MS-ESI Calculated [M+H]$^+$ 293, Found 293.

Step 3

Compound 19-3 (3.50 g, 12.0 mmol) and compound 17-5 (1.81 g, 13.2 mmol) were dissolved in 1,4-dioxane (50 ml) and water (5 ml). Potassium carbonate (4.98 g, 36.1 mmol) and 1,1'-bis(diphenylphosphino)ferrocene palladium dichloride (879 mg, 1.20 mmol) were added to the reaction solution under nitrogen protection, and stirred at 90° C. for 12 hours. After the reaction was completed, the reaction mixture was filtered. The filtrate was diluted with water (100 ml) and then extracted with ethyl acetate (70 ml×3). The combined organic phase was washed with saturated brine (100 ml×2), dried with anhydrous sodium sulfate, filtered, and concentrated under reduced pressure. The obtained residue was isolated by silica gel column chromatography to give compound 19-4. $^1$H NMR (400 MHz, CDCl$_3$) δ ppm 8.72 (s, 1H), 8.62 (br d, J=4.89 Hz, 1H), 7.82-7.87 (m, 1H), 7.80 (br s, 2H), 7.67 (br d, J=4.89 Hz, 1H), 7.29 (s, 1H), 4.34-4.52 (m, 2H), 3.65 (br s, 1H), 2.67 (s, 3H), 1.28 (s, 9H). MS-ESI Calculated [M+H]$^+$ 304, Found 304.

Step 4

Compound 19-4 (1.60 g, 5.07 mmol) was dissolved in ethyl acetate (15 ml). Hydrochloric acid/ethyl acetate (4 mol, 9.61 ml) was added to the reaction solution, and the mixture was stirred at 25° C. for 2 hours. After the reaction was completed, the reaction solution was concentrated under reduced pressure, and the obtained residue was compound 19-5.

MS-ESI Calculated [M+H]$^+$ 200, Found 200.

Step 5

Compound 19-5 (1.00 g, 5.02 mmol) and compound 1-3 (992 mg, 4.27 mmol) were dissolved in N-methylpyrrolidone (15 ml). N,N-diisopropylethylamine (2.59 g, 20.1 mmol, 3.50 ml) was added to the reaction solution, and the mixture was stirred at 130° C. for 3 hours. After the reaction was completed, the reaction mixture was diluted with water (50 ml) and then extracted with ethyl acetate (15 ml×3). The combined organic phase was washed with saturated brine (20 ml×3), dried with anhydrous sodium sulfate, filtered, and concentrated under reduced pressure. The obtained residue was purified by silica gel thin-layer chromatography to give compound 19-6.

MS-ESI Calculated [M+H]$^+$ 397, Found 397.

Step 6

Compound 19-6 (0.150 g, 333 μmol), compound 17-9 (52.7 mg, 432 μmol), 1,1'-bis(diphenylphosphino)ferrocene palladium dichloride (24.3 mg, 33.3 μmol), and potassium carbonate (138 mg, 998 μmol) were dissolved in dioxane (3 ml) and water (0.2 ml), and reacted at 90° C. under nitrogen protection for 12 hours. After the reaction was completed, the reaction mixture was diluted with water (30 ml) and then extracted with ethyl acetate (20 ml×3). The combined organic phase was washed with saturated brine (20 ml×4), dried with anhydrous sodium sulfate, filtered, and concentrated under reduced pressure. The obtained residue was purified by silica gel thin-layer chromatography, and then isolated by high-performance liquid chromatography (formic acid condition) to give compound 19.

¹HNMR (400 MHz, CD₃OD) δ ppm 8.79 (d, J=1.47 Hz, 1H), 8.52 (d, J=5.50 Hz, 1H), 7.97-8.08 (m, 2H), 7.93 (s, 1H), 7.84 (dd, J=5.38, 1.34 Hz, 1H), 7.78 (d, J=4.89 Hz, 1H), 7.68 (s, 1H), 7.63-7.66 (m, 2H), 7.55-7.61 (m, 2H), 7.47-7.53 (m, 1H), 7.36 (d, J=4.77 Hz, 1H), 4.91 (s, 2H), 2.64 (s, 3H). MS-ESI Calculated [M+H]⁺ 393, Found 393.

Example 20

Route for Synthesis:

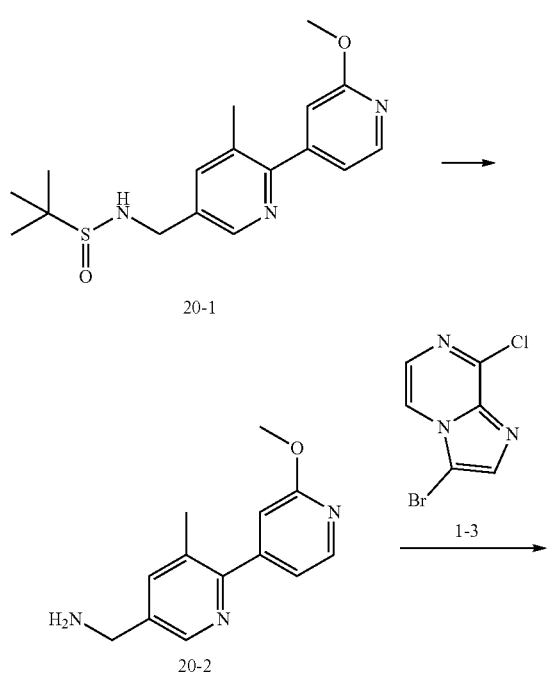

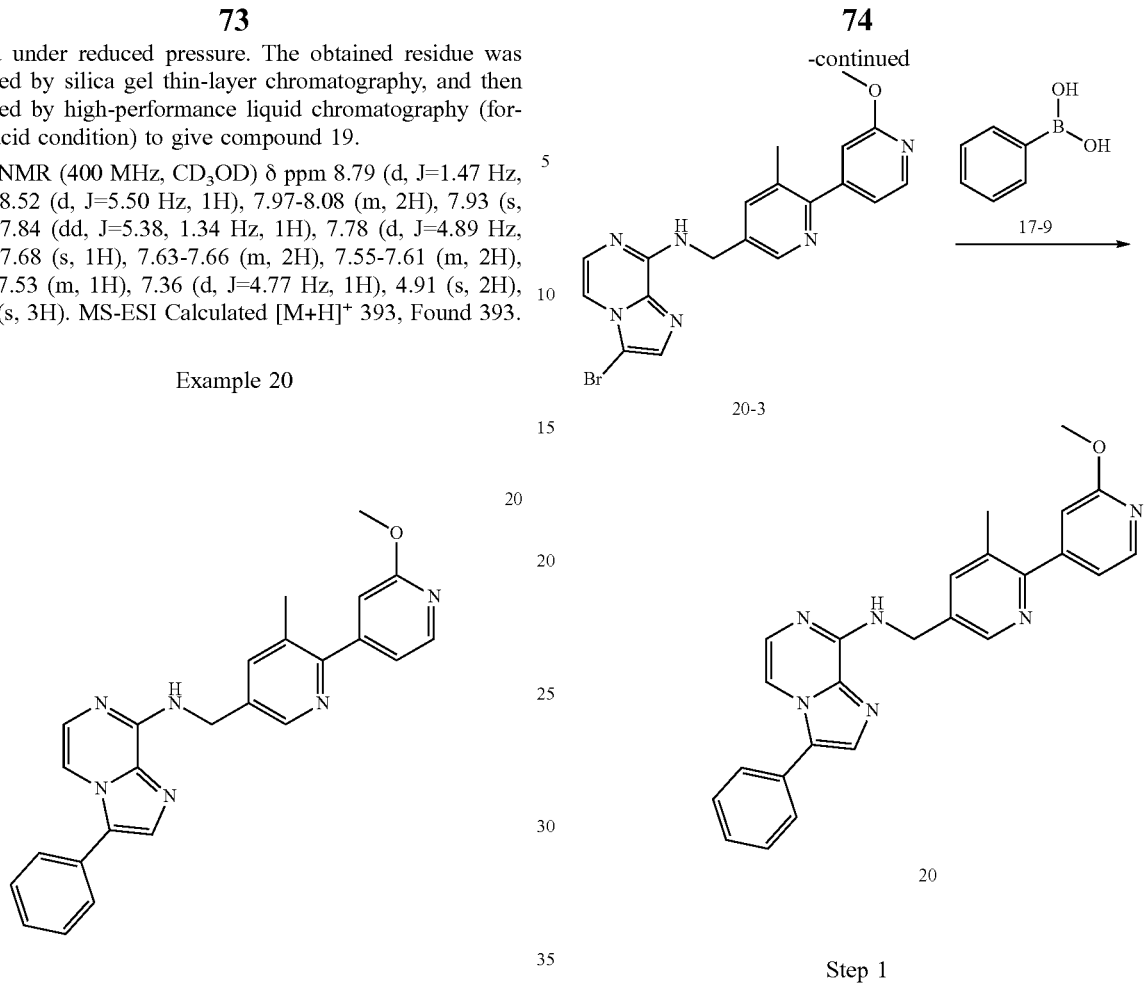

Step 1

Compound 20-1 (0.120 g, 360 μmol) was dissolved in ethyl acetate (3 ml). Hydrochloric acid/ethyl acetate (4 mol, 1 ml) was added to the reaction solution, and the mixture was stirred at 25° C. for 2 hours. After the reaction was completed, the reaction solution was concentrated under reduced pressure to give compound 20-2.

Step 2

Compound 20-2 (80.0 mg, 349 μmol) and compound 1-3 (69.0 mg, 297 μmol) were dissolved in N-methylpyrrolidone (4 ml). N,N-diisopropylethylamine (180 mg, 1.40 mmol, 243 μl) was added to the reaction solution, and the mixture was stirred at 130° C. for 3 hours. After the reaction was completed, the reaction mixture was diluted with water (20 ml) and then extracted with ethyl acetate (15 ml×3). The combined organic phase was washed with saturated brine (20 ml×3), dried with anhydrous sodium sulfate, filtered, and concentrated under reduced pressure. The obtained residue was purified by thin-layer chromatography to give compound 20-3.

MS-ESI Calculated [M+H]⁺ 426, Found 426.

Step 3

Compound 20-3 (30.0 mg, 70.5 μmol), compound 17-9 (11.2 mg, 91.7 μmol), 1,1'-bis(diphenylphosphino)ferrocene palladium dichloride (5.16 mg, 7.05 μmol), and potassium carbonate (29.3 mg, 212 μmol) were dissolved in dioxane (3 ml) and water (0.2 ml), and reacted at 90° C. under nitrogen protection for 12 hours. After the reaction was completed, the reaction mixture was diluted with water (30 ml) and then extracted with ethyl acetate (20 ml×3). The combined organic phase was washed with saturated brine (20 ml×4), dried with anhydrous sodium sulfate, filtered, and concentrated under reduced pressure. The residue was purified by thin-layer chromatography, and then isolated by high-performance liquid chromatography (formic acid condition) to give compound 20.

$^{1}$HNMR (400 MHz, CDCl$_3$) δ ppm 8.63 (s, 1H), 8.25 (d, J=5.26 Hz, 1H), 7.72 (s, 1H), 7.62-7.66 (m, 2H), 7.56 (m, 4H), 7.47-7.52 (m, 1H), 7.44 (br s, 1H), 7.03 (dd, J=5.26, 1.34 Hz, 1H), 6.87 (s, 1H), 4.94 (br s, 2H), 3.99 (s, 3H), 2.35 (s, 3H). MS-ESI Calculated [M+H]$^+$ 423, Found 423.

Example 21

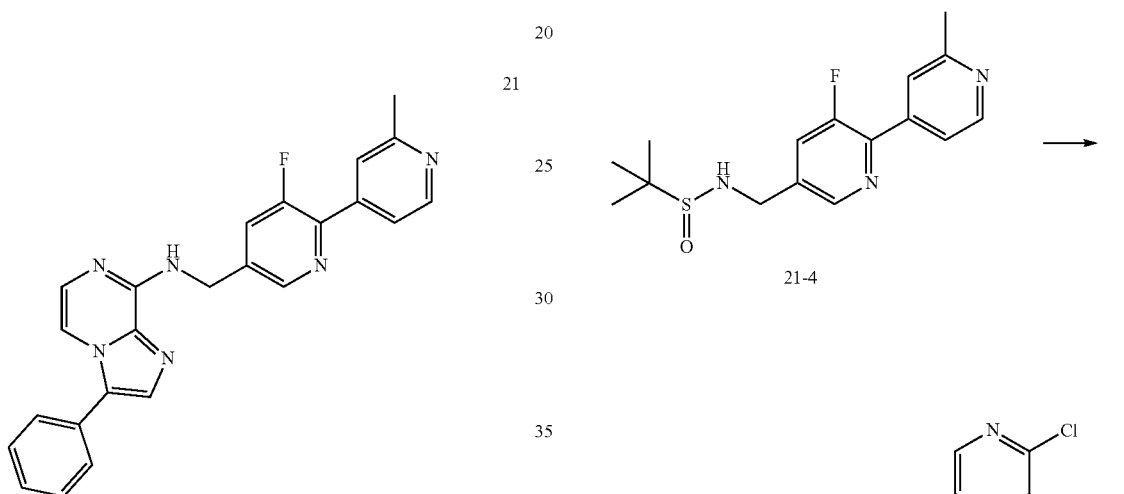

Route for Synthesis:

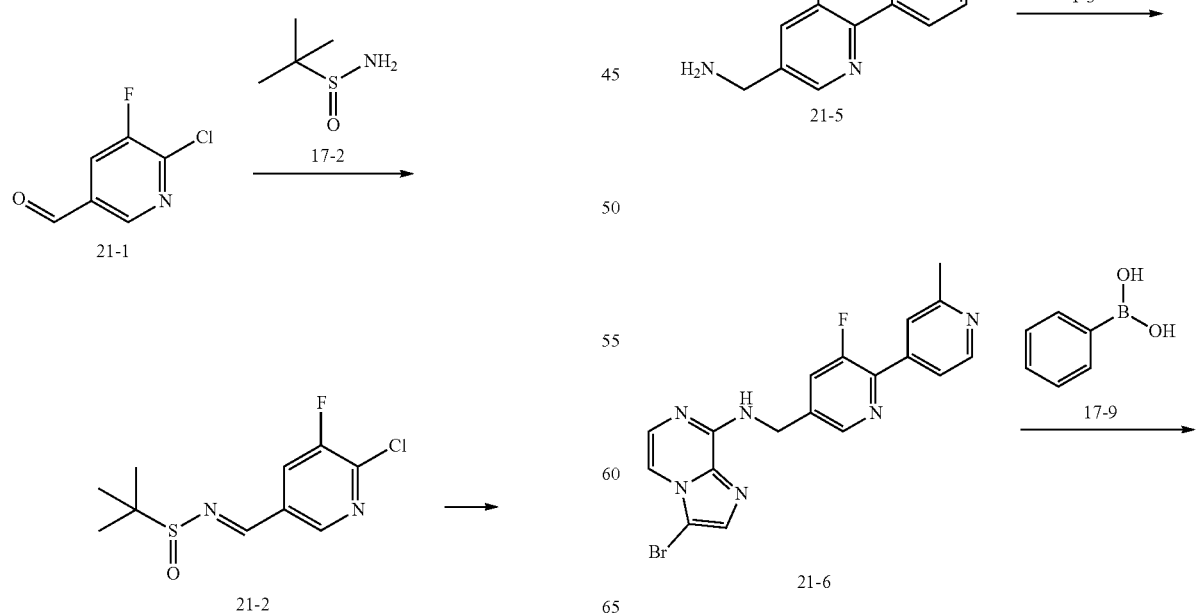

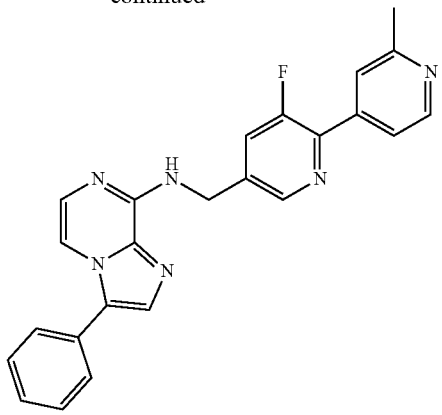

21

Step 1

Compound 21-1 (400 mg, 2.51 mmol) and compound 17-2 (455.80 mg, 3.76 mmol) were dissolved in tetrahydrofuran (10 ml). Anhydrous copper sulfate (880.36 mg, 5.52 mmol) was added to the reaction solution, and the reaction mixture was stirred at 80° C. for 16 hours. After the reaction was completed, the reaction mixture was diluted with water (20 ml), and the mixture was extracted with ethyl acetate (20 ml×2). The organic phase was dried with anhydrous sodium sulfate and rotary evaporated to dryness to give crude product of compound 21-2. MS-ESI Calculated [M+H]$^+$ 263, Found 263.

Step 2

Compound 21-2 (800 mg, 3.04 mmol) was dissolved in tetrahydrofuran (15 ml) and methanol (3 ml), and sodium borohydride (69.12 mg, 1.83 mmol) was added to the reaction solution at 0° C. The reaction mixture was stirred at 25° C. for 1 hour. After the reaction was completed, the reaction mixture was diluted with water (20 ml), and the mixture was extracted with ethyl acetate (20 ml×2). The combined organic phase was washed with saturated sodium chloride solution (20 ml×2), dried with anhydrous sodium sulfate, filtered, and concentrated under reduced pressure to give crude product of compound 21-3. MS-ESI Calculated [M+H]$^+$ 265, Found 265.

Step 3

Compound 21-3 (400 mg, 1.51 mmol), compound 17-5 (310.36 mg, 2.27 mmol), and potassium carbonate (626.44 mg, 4.53 mmol) were dissolved in dioxane (10 ml) and water (1 ml), and 1,1'-bis(diphenylphosphino)ferrocene palladium dichloride (165.83 mg, 226.63 µmol) was added to the reaction solution. The gas in the reaction mixture was replaced, and the reaction mixture was stirred at 80° C. under nitrogen protection for 16 hours. After the reaction was completed, the reaction mixture was diluted with water (20 ml), and the mixture was extracted with ethyl acetate (20 ml×2). The combined organic phase was washed with saturated sodium chloride solution (20 ml×2), dried with anhydrous sodium sulfate, filtered, and concentrated under reduced pressure. The residue was purified by thin-layer chromatography to give compound 21-4.

MS-ESI Calculated [M+H]$^+$ 322, Found 322.

Step 4

Compound 21-4 (436 mg, 1.36 mmol) was dissolved in ethyl acetate (8 ml) and methanol (2 ml). Hydrochloric acid/ethyl acetate (4 M, 8.82 ml) was added to the reaction solution, and the reaction mixture was stirred at 25° C. for 12 hours. After the reaction was completed, ethyl acetate (20 ml) was added, and the mixture was filtered. The filter cake was stirred in ethyl acetate (20 ml) at 25° C. for half an hour to give compound 21-5.

MS-ESI Calculated [M+H]$^+$ 218, Found 218.

Step 5

Compound 21-5 (269 mg, 1.24 mmol) was dissolved in N-methylpyrrolidone (5 ml). Compound 1-3 (316.64 mg, 1.36 mmol) and N,N-diisopropylethylamine (640.14 mg, 4.95 mmol) were added to the reaction solution, and the reaction mixture was stirred at 130° C. for 4 hours. After the reaction was completed, the reaction mixture was diluted with water (20 ml), and the mixture was extracted with ethyl acetate (30 ml×3). The combined organic phase was washed with saturated sodium chloride solution (20 ml×2), dried with anhydrous sodium sulfate, filtered, and concentrated under reduced pressure. The residue was purified by silica gel column chromatography to give compound 21-6.

MS-ESI Calculated [M+H]$^+$ 414, Found 414.

Step 6

Compound 21-6 (1 g, 2.42 mmol) and compound 17-9 (442.58 mg, 3.63 mmol) were dissolved in dioxane (10 ml) and water (1 ml). 1,1'-bis(diphenylphosphino)ferrocene palladium dichloride (265.59 mg, 362.98 µmol) and potassium carbonate (1.00 g, 7.26 mmol) were added to the reaction solution. The gas in the reaction mixture was replaced and the reaction mixture was stirred at 80° C. under nitrogen protection for 15 hours. After the reaction was completed, the reaction solution was diluted with water (20 ml), and extracted with ethyl acetate (20 ml×3). The organic phase was washed with saturated sodium chloride solution (20 ml×2), and purified by thin-layer chromatography and high-performance liquid chromatography (formic acid condition) to give compound 21.

$^1$H NMR (400 MHz, CD$_3$OD) δ ppm 8.65 (s, 1H), 8.53 (d, J=5.4 Hz, 1H), 7.86 (s, 1H), 7.75-7.784 (m, 3H), 7.68 (s, 1H), 7.61-7.66 (m, 2H), 7.54-7.60 (m, 2H), 7.46-7.53 (m, 1H), 7.36 (d, J=4.9 Hz, 1H), 4.92 (s, 2H), 2.63 (s, 3H). MS-ESI Calculated [M+H]$^+$ 411, Found 411.

Example 22

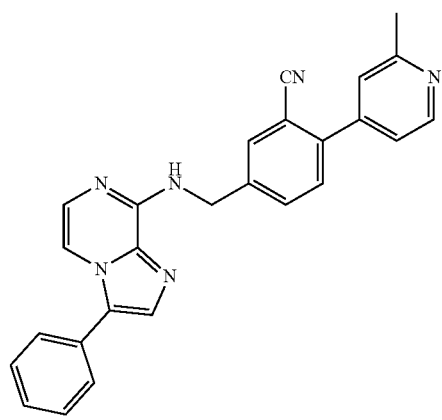

Route for Synthesis:

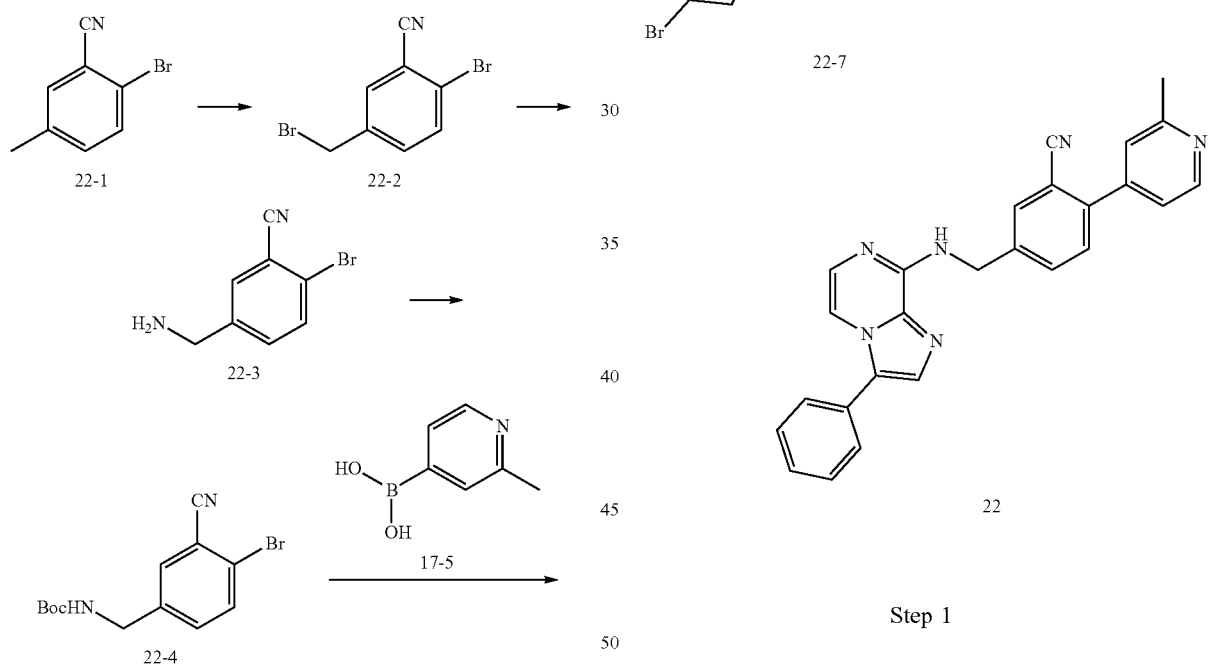

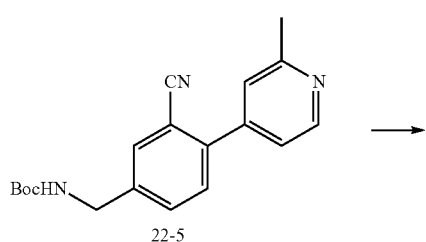

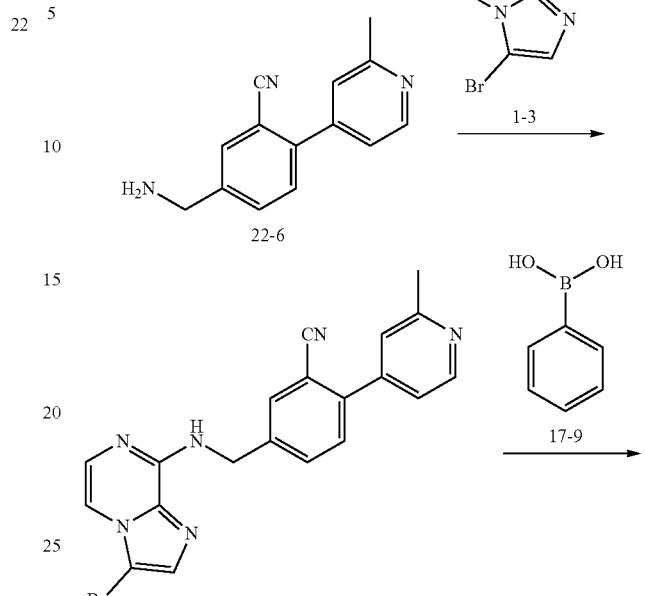

Step 1

Compound 22-1 (5 g, 25.50 mmol) and azobisisobutyronitrile (418.80 mg, 2.55 mmol) were dissolved in carbon tetrachloride (50 ml). NBS (4.09 g, 22.95 mmol) was added to the reaction solution. The gas in the reaction mixture was replaced, and the reaction mixture was stirred at 60° C. under nitrogen protection for 15 hours. After the reaction was completed, the reaction mixture was diluted with water (200 ml), and the mixture was extracted with dichloromethane (200 ml). The organic phase was dried with anhydrous sodium sulfate, and rotary evaporated to dryness. The residue was purified by silica gel column chromatography to give compound 22-2.

$^1$H NMR (400 MHz, DMSO-$d_6$) δ ppm 8.06 (d, J=2.13 Hz, 1H), 7.90 (d, J=8.38 Hz, 1H), 7.73 (dd, J=8.38, 2.25 Hz, 1H), 4.72 (s, 2H). MS-ESI Calculated [M+H]$^+$ 274, Found 274.

Step 2

Compound 22-2 (2 g, 7.27 mmol) was dissolved in ammonia/ethanol (15 ml), and the reaction mixture was stirred at 15° C. for 2 hours. After the reaction was completed, the reaction solution was concentrated under reduced pressure. The residue was stirred in dichloromethane (50 ml) at 25° C. for half an hour to give compound 22-3.

MS-ESI Calculated [M+H]$^+$ 212, Found 212.

Step 3

Compound 22-3 (1.1 g, 5.21 mmol), Boc-anhydride (1.36 g, 6.25 mmol, 1.44 ml), and triethylamine (1.32 g, 13.03 mmol, 1.81 ml) were dissolved in anhydrous dichloromethane (20 ml). The gas in the reaction mixture was replaced, and the reaction mixture was stirred at 25° C. under nitrogen protection for 2 hours. After the reaction was completed, the reaction solution was concentrated under reduced pressure to give crude product of compound 22-4.

MS-ESI Calculated [M+H]$^+$ 312, Found 312.

Step 4

Compound 22-4 (1.3 g, 4.18 mmol) was dissolved in dioxane (3 ml). Compound 17-5 (629.33 mg, 4.60 mmol), potassium carbonate (1.73 g, 12.53 mmol), and 1,1'-bis(diphenylphosphino)ferrocene palladium dichloride (305.69 mg, 417.77 μmol) were added to the reaction solution, and the reaction mixture was stirred at 80° C. for 15 hours. After the reaction was completed, the reaction mixture was diluted with water (50 ml), and the mixture was extracted with ethyl acetate (50 ml). The organic phase was dried with anhydrous sodium sulfate, and rotary evaporated to dryness. The residue was purified by silica gel column chromatography to give compound 22-5.

MS-ESI Calculated [M+H]$^+$ 324, Found 324.

Step 5

Compound 22-5 (610 mg, 1.89 mmol) and trifluoroacetic acid (1.34 g, 11.77 mmol) were dissolved in anhydrous dichloromethane (2 ml), and the reaction mixture was stirred at 25° C. for 2 hours. After the reaction was completed, the reaction solution was concentrated under reduced pressure. The residue was purified by high-performance liquid chromatography (formic acid condition) to give compound 22-6.
MS-ESI Calculated [M+H]$^+$ 224, Found 224.

Step 6

Compound 22-6 (150 mg, 557.00 μmol) was dissolved in N-methylpyrrolidone (5 ml). Compound 1-3 (181.28 mg, 779.81 μmol) and DIEA (359.94 mg, 2.79 mmol) were added to the reaction solution, and the reaction mixture was stirred at 200° C. for 1 hour. After the reaction was completed, water (30 ml) was added, and the mixture was filtered. Water (20 ml) was added to the filter cake, and the mixture was stirred at 25° C. for 30 minutes to give compound 22-7. MS-ESI Calculated [M+H]$^+$ 420, Found 420.

Step 7

Compound 22-7 (100 mg, 238.51 μmol) and compound 17-9 (31.99 mg, 262.36 μmol) were dissolved in dioxane (3 ml). 1,1'-bis(diphenylphosphino)ferrocene palladium dichloride (17.45 mg, 23.85 μmol) and potassium carbonate (98.89 mg, 715.52 μmol) were added to the reaction solution. The gas in the reaction mixture was replaced, and the reaction mixture was stirred at 80° C. under nitrogen protection for 15 hours. After the reaction was completed, the reaction solution was diluted with water (20 ml), and extracted with ethyl acetate (20 ml). The organic phase was washed with water (10 ml×2), and purified by high-performance liquid chromatography (formic acid condition) to give the formate salt of compound 22.

$^1$H NMR (400 MHz, CD$_3$OD) δ ppm 8.52 (d, J=5.15 Hz, 1H), 8.34-8.40 (m, 1H), 7.91-7.95 (m, 1H), 7.81-7.87 (m, 1H), 7.74-7.79 (m, 1H), 7.64-7.69 (m, 1H), 7.59-7.65 (m, 3H), 7.53-7.59 (m, 2H), 7.42-7.52 (m, 3H), 7.31-7.35 (m, 1H), 2.56-2.67 (m, 3H). MS-ESI Calculated [M+H]$^+$ 417, Found 417.

Example 23

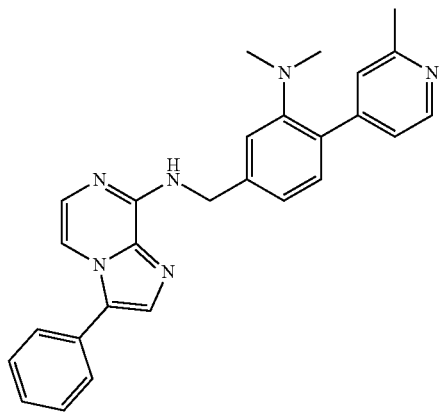

23

Route for Synthesis:

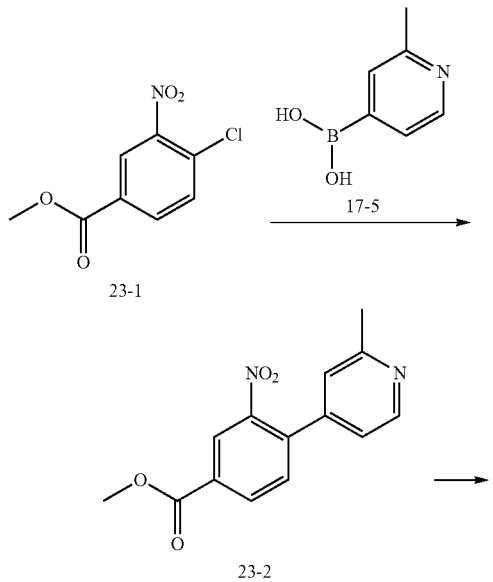

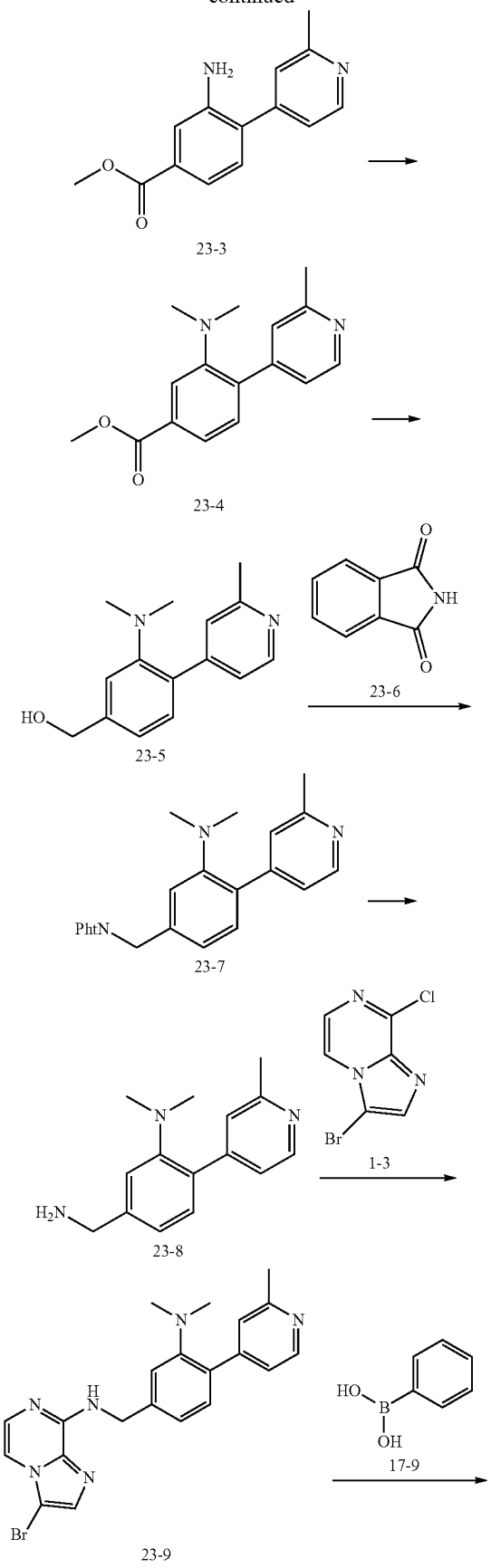

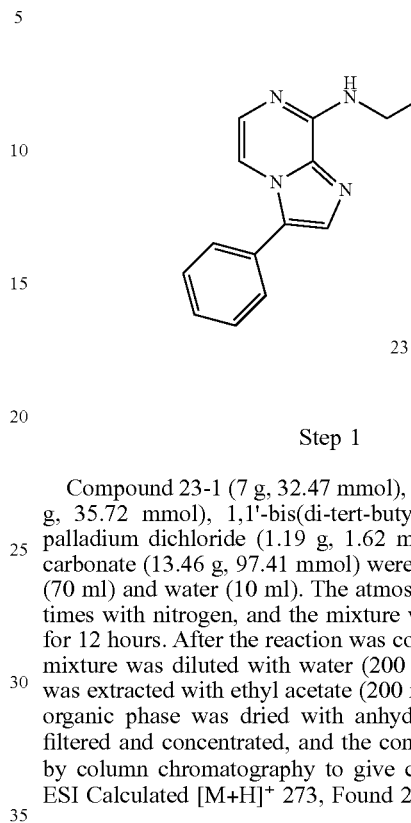

Step 1

Compound 23-1 (7 g, 32.47 mmol), compound 17-5 (4.89 g, 35.72 mmol), 1,1'-bis(di-tert-butylphosphino)ferrocene palladium dichloride (1.19 g, 1.62 mmol), and potassium carbonate (13.46 g, 97.41 mmol) were dissolved in dioxane (70 ml) and water (10 ml). The atmosphere was replaced 3 times with nitrogen, and the mixture was reacted at 90° C. for 12 hours. After the reaction was completed, the reaction mixture was diluted with water (200 ml), and the mixture was extracted with ethyl acetate (200 ml×3). The combined organic phase was dried with anhydrous sodium sulfate, filtered and concentrated, and the concentrate was purified by column chromatography to give compound 23-2. MS-ESI Calculated [M+H]$^+$ 273, Found 273.

Step 2

Compound 23-2 (3 g, 11.02 mmol) was dissolved in ethanol (60 ml) and water (20 ml). Reduced iron powder (1.85 g, 33.06 mmol) and ammonium chloride (5.89 g, 110.19 mmol) were added, and the mixture was reacted at 60° C. for 1 hour. After the reaction was completed, the reaction mixture was diluted with water (50 ml), and the mixture was extracted with ethyl acetate (50 ml×3). The combined organic phase was dried with anhydrous sodium sulfate, filtered, and concentrated to give compound 23-3. MS-ESI Calculated [M+H]$^+$ 243, Found 243.

Step 3

Compound 23-3 (2.3 g, 9.49 mmol) and aqueous formaldehyde solution (69.00 ml) were dissolved in methanol (200 ml). Acetic acid (10.50 g, 174.85 mmol) and sodium cyanoborohydride (2.39 g, 37.97 mmol) were added, and the mixture was reacted at 20° C. for 12 hours. After the reaction was completed, the reaction mixture was diluted with water (200 ml), and the mixture was extracted with ethyl acetate (50 ml×3). The combined organic phase was dried with anhydrous sodium sulfate, filtered and concentrated, and the concentrate was purified by column chromatography to give compound 23-4. MS-ESI Calculated [M+H]$^+$ 271, Found 271.

Step 4

Compound 23-4 (3 g, 11.10 mmol) was dissolved in tetrahydrofuran (100 ml). Lithium aluminum hydride (842.41 mg, 22.20 mmol) was added at 0° C., and the mixture was reacted at 0° C. for 1 hour. After the reaction was completed, the reaction mixture was diluted with water (1 ml). 15% aqueous sodium hydroxide solution (1 ml) was added, and then water was added (3 ml). The mixture was filtered, and the filtrate was concentrated to give compound 23-5. MS-ESI Calculated [M+H]$^+$ 243, Found 243.

Step 5

Compound 23-5 (2.2 g, 9.08 mmol), compound 23-6 (2.00 g, 13.62 mmol), and triphenylphosphine (2.86 g, 10.89 mmol) were dissolved in tetrahydrofuran (20 ml). Diisopropyl azodicarboxylate (2.20 g, 10.89 mmol) was added and reacted at 20° C. for 12 hours. After the reaction was completed, the reaction mixture was diluted with water (50 ml), and the mixture was extracted with ethyl acetate (50 ml×3). The combined organic phase was dried with anhydrous sodium sulfate, filtered and concentrated, and the concentrate was purified by high-performance liquid chromatography (alkaline condition) to give compound 23-7.
MS-ESI Calculated [M+H]$^+$ 372, Found 372.

Step 6

Compound 23-7 (750 mg, 2.02 mmol) was dissolved in ethanol (20 ml), and hydrazine hydrate (1.01 g, 20.19 mmol) was added. The atmosphere was replaced 3 times with nitrogen, and the mixture was reacted at 60° C. for 5 hours. After the reaction was completed, the reaction mixture was diluted with water (50 ml), and the mixture was extracted with ethyl acetate (50 ml×3). The combined organic phase was dried with anhydrous sodium sulfate, filtered and concentrated, and the concentrate was purified by high-performance liquid chromatography (alkaline condition) to give compound 23-8. MS-ESI Calculated [M+H]$^+$ 242, Found 242.

Step 7

Compound 23-8 (250 mg, 1.04 mmol), compound 1-3 (288.98 mg, 1.24 mmol), and N,N-diisopropylethylamine (401.66 mg, 3.11 mmol) were dissolved in dimethylformamide (5 ml). The atmosphere was replaced 3 times with nitrogen, and the mixture was reacted at 60° C. for 5 hours. After the reaction was completed, the reaction mixture was diluted with water (20 ml), and the mixture was extracted with ethyl acetate (20 ml×3). The combined organic phase was dried with anhydrous sodium sulfate, filtered and concentrated, and the concentrate was purified by high-performance liquid chromatography (alkaline condition) to give compound 23-9.
MS-ESI Calculated [M+H]$^+$ 438, Found 438.

Step 8

Compound 23-9 (50 mg, 114.33 μmol), compound 17-9 (27.88 mg, 228.66 μmol), 1,1'-bis(diphenylphosphino)ferrocene palladium dichloride (8.37 mg, 11.43 μmol), and potassium carbonate (47.40 mg, 342.99 μmol) were dissolved in dioxane (2 ml) and water (0.5 ml). The atmosphere was replaced 3 times with nitrogen, and the mixture was reacted at 80° C. for 12 hours. After the reaction was completed, the reaction mixture was diluted with water (20 ml), and the mixture was extracted with ethyl acetate (20 ml×3). The combined organic phase was dried with anhydrous sodium sulfate, filtered and concentrated, and the concentrate was purified by a preparative plate (dichloromethane:methanol=10:1) to give a crude product. The crude product was purified by high-performance liquid chromatography (hydrochloric acid condition) to give compound 23.

$^1$H NMR (400 MHz, CD$_3$OD) δ ppm 8.74 (d, J=6.1 Hz, 1H), 8.10-8.20 (m, 2H), 7.93-8.02 (m, 2H), 7.81 (br s, 1H), 7.68-7.73 (m, 2H), 7.59-7.68 (m, 3H), 7.47-7.57 (m, 2H), 7.32 (d, J=5.7 Hz, 1H), 5.07 (br s, 2H), 3.01 (br s, 6H), 2.88 (s, 3H). MS-ESI Calculated [M+H]$^+$ 435, Found 435.

Example 24

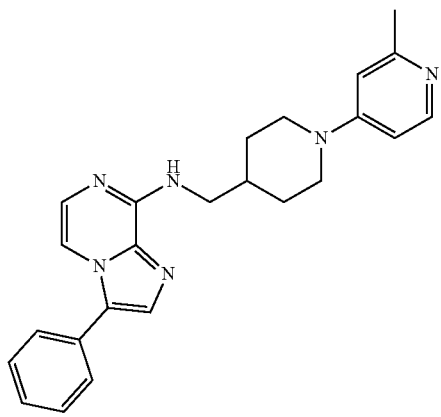

Route for Synthesis:

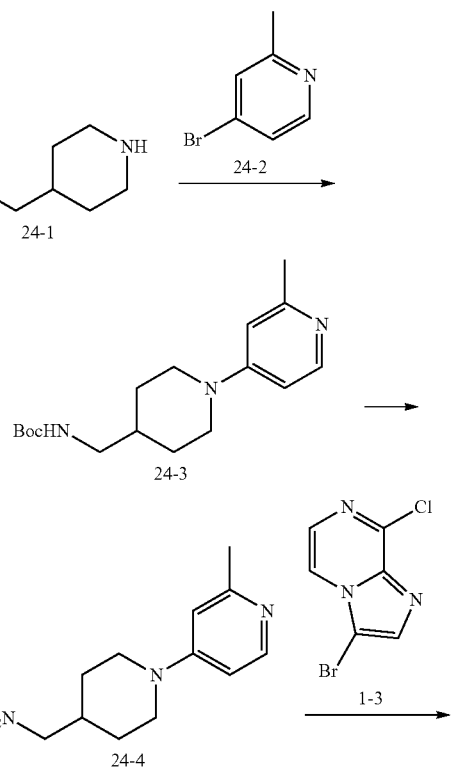

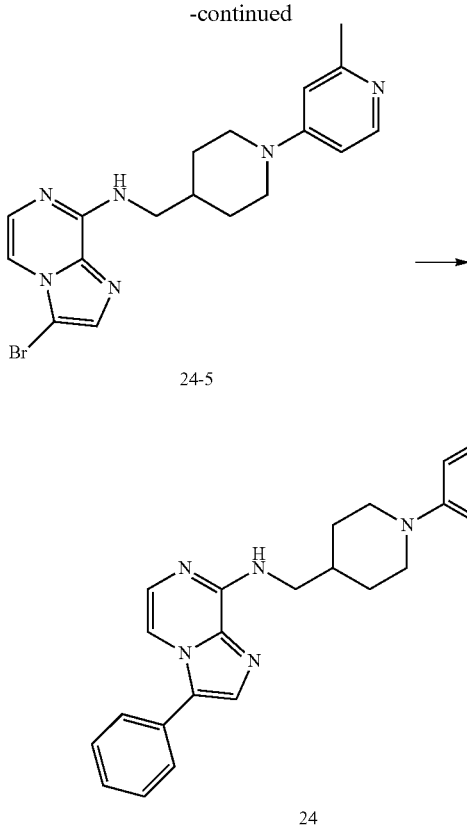

Step 1

Compound 24-2 (1 g, 5.81 mmol), compound 24-1 (1.49 g, 6.98 mmol), tris(dibenzylideneacetone)dipalladium (532.32 mg, 581.32 μmol), 4,5-bis(diphenylphosphino)-9,9-dimethylxanthene (672.72 mg, 1.16 mmol), and cesium carbonate (3.79 g, 11.63 mmol) were dissolved in dioxane (20 ml). The atmosphere was replaced 3 times with nitrogen, and the mixture was reacted at 80° C. for 12 hours. After the reaction was completed, the reaction mixture was diluted with water (50 ml), and the mixture was extracted with ethyl acetate (50 ml×3). The combined organic phase was dried with anhydrous sodium sulfate, filtered and concentrated. The concentrate was subjected to column chromatography to give compound 24-3. MS-ESI Calculated [M+H]$^+$ 306, Found 306.

Step 2

Compound 24-3 (1.5 g, 4.91 mmol) was dissolved in ethyl acetate (20 ml). A solution of hydrogen chloride in ethyl acetate (4 mol/L, 20 ml) was added and the mixture was reacted at 20° C. for 1 hour. After the reaction was completed, the reaction solution was rotary evaporated to dryness to give compound 24-4.
MS-ESI Calculated [M+H]$^+$ 206, Found 206.

Step 3

Compound 24-4 (831.99 mg, 3.44 mmol) and compound 1-3 (800 mg, 3.44 mmol) were dissolved in dimethylformamide (10 ml). N,N-diisopropylethylamine (2.22 g, 17.21 mmol) was added and the mixture was reacted at 130° C. for 4 hours. After the reaction was completed, the reaction mixture was diluted with water (50 ml), and the mixture was extracted with ethyl acetate (50 ml×3). The combined organic phase was dried with anhydrous sodium sulfate, filtered and concentrated. The concentrate was purified by high-performance liquid chromatography (hydrochloric acid condition) to give compound 24-5. MS-ESI Calculated [M+H]$^+$ 402, Found 402.

Step 4

Compound 24-5 (200 mg, 498.38 μmol), phenylboronic acid (91.15 mg, 747.56 μmol), 1,1'-bis(diphenylphosphino)ferrocene palladium dichloride (36.47 mg, 49.84 μmol), and potassium carbonate (206.64 mg, 1.50 mmol) were dissolved in dioxane (2 ml) and water (0.5 ml). The atmosphere was replaced 3 times with nitrogen, and the mixture was reacted at 90° C. for 12 hours. After the reaction was completed, the reaction mixture was diluted with water (20 ml), and the mixture was extracted with ethyl acetate (20 ml×3). The combined organic phase was dried with anhydrous sodium sulfate, filtered and concentrated. The concentrate was purified by silica gel thin-layer chromatography to give a crude product, and the crude product was purified by high-performance liquid chromatography (hydrochloric acid condition) to give compound 24.

$^1$H NMR (400 MHz, CD$_3$OD) δ ppm 7.97-8.04 (m, 1H), 7.89-7.95 (m, 2H), 7.56-7.72 (m, 5H), 7.26 (d, J=5.9 Hz, 1H), 7.04-7.11 (m, 2H), 4.36 (br d, J=13.9 Hz, 2H), 3.59 (br d, J=7.0 Hz, 2H), 3.22-3.28 (m, 2H), 2.54 (s, 3H), 2.31 (dt, J=3.7, 7.4 Hz, 1H), 2.04-2.16 (m, 2H), 1.37-1.58 (m, 2H). MS-ESI Calculated [M+H]$^+$ 399, Found 399.

Example 25

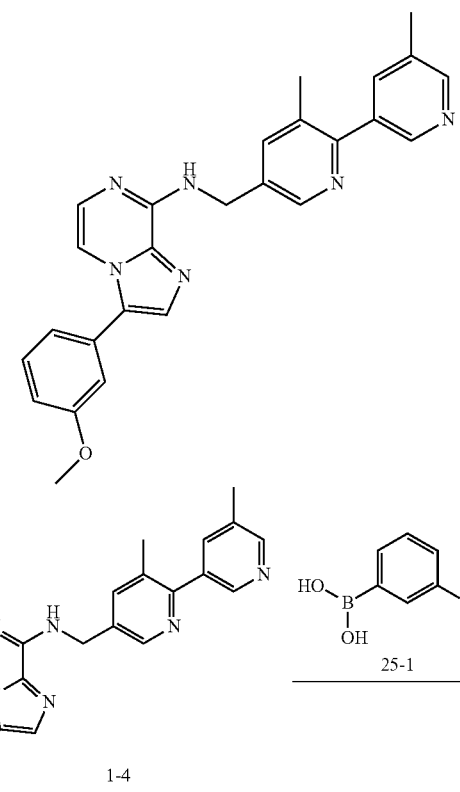

-continued

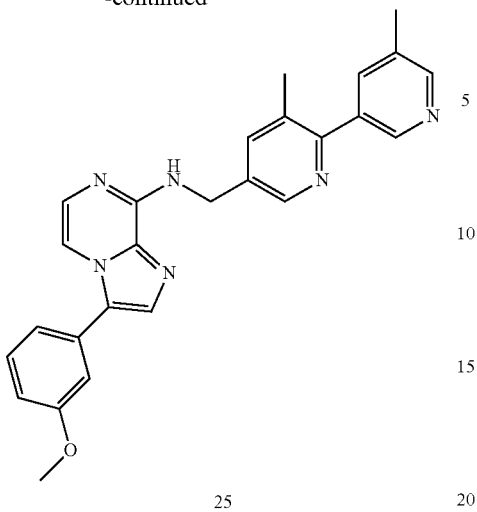

25

-continued

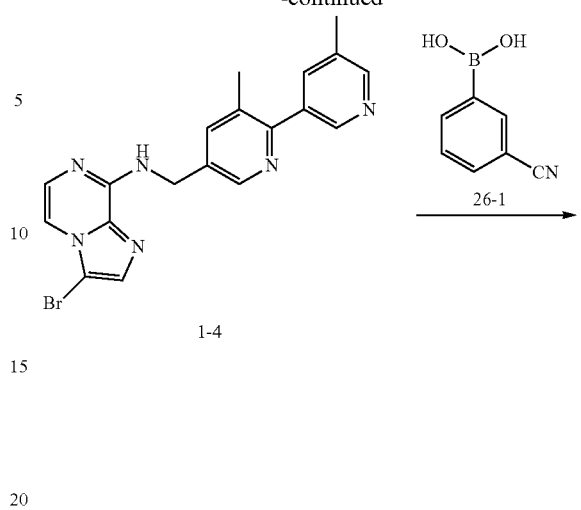

Compound 1-4 (100 mg, 244.33 μmol) was dissolved in dioxane (5 ml) and water (0.25 ml), and then compound 25-1 (26.82 mg, 256.55 μmol), potassium carbonate (67.54 mg, 488.66 μmol), and 1,1'-bis(diphenylphosphino)ferrocene palladium dichloride (26.82 mg, 36.65 μmol) were added in sequence. The reaction mixture was stirred at 80° C. under nitrogen protection for 16 hours. After the reaction was completed, the reaction solution was concentrated under reduced pressure. Water was added (30 ml), and the mixture was extracted with ethyl acetate (30 ml×3). The organic phases were combined, dried with anhydrous sodium sulfate, filtered, and concentrated under reduced pressure. The residue was isolated by thin-layer chromatography, and then isolated by high-performance liquid chromatography (formic acid condition) to give the formate salt of compound 25.

$^1$H NMR (400 MHz, CD$_3$OD) δ ppm 8.59-8.66 (m, 2H), 7.92 (s, 1H), 7.82 (d, J=4.9 Hz, 1H), 7.62-7.76 (m, 3H), 7.50 (t, J=8.0 Hz, 1H), 7.36 (d, J=4.9 Hz, 1H), 7.15-7.23 (m, 2H), 7.08 (dd, J=1.8, 8.5 Hz, 1H), 4.91 (s, 2H), 3.89 (s, 3H), 2.72 (d, J=4.9 Hz, 3H), 2.42 (s, 3H). MS-ESI Calculated [M+H]$^+$ 437, Found 437.

Example 26

Compound 1-4 (260 mg, 635.26 μmol) was dissolved in dioxane (5 ml) and water (0.5 ml), and then compound 26-1 (140.02 mg, 952.89 μmol), potassium carbonate (263.39 mg, 1.91 mmol), and 1,1'-bis(diphenylphosphino)ferrocene palladium dichloride (69.72 mg, 95.29 μmol) were added in sequence. The reaction mixture was stirred at 90° C. under nitrogen protection for 12 hours. After the reaction was completed, the reaction solution was concentrated under reduced pressure. Water was added (30 ml), and the mixture was extracted with ethyl acetate (30 ml×3). The organic phases were combined, dried with anhydrous sodium sulfate, filtered, and concentrated under reduced pressure. The residue was isolated by thin-layer chromatography and then isolated by high-performance liquid chromatography (formic acid condition) to give compound 26.

$^1$H NMR (400 MHz, CD$_3$OD) δ ppm 8.50-8.58 (m, 2H), 8.05 (s, 1H), 7.98 (d, J=7.8 Hz, 1H), 7.82-7.89 (m, 2H), 7.73-7.82 (m, 3H), 7.45 (s, 1H), 7.41 (d, J=4.8 Hz, 1H), 7.38 (d, J=5.1 Hz, 1H), 4.88-4.88 (m, 2H), 2.62 (s, 3H), 2.36 (s, 3H). MS-ESI Calculated [M+H]$^+$ 432, Found 432.

Example 27

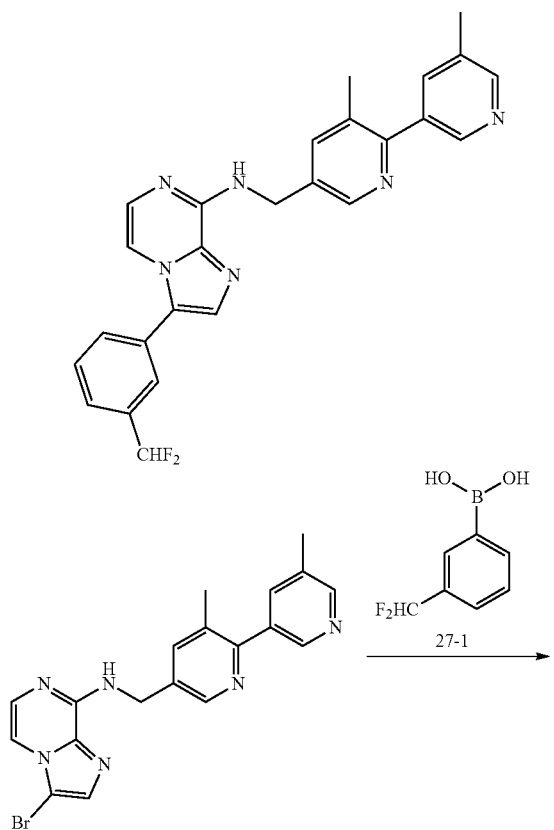

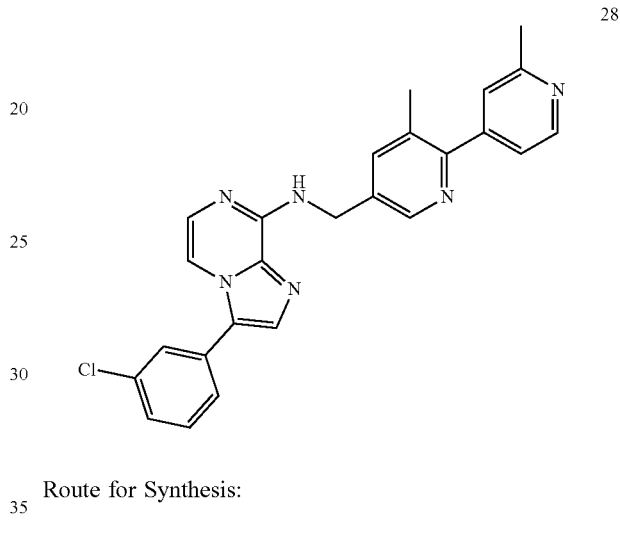

Compound 1-4 (184 mg, 449.57 μmol) was dissolved in dioxane (5 ml) and water (0.25 ml), and then compound 27-1 (115.95 mg, 674.35 μmol), potassium carbonate (186.40 mg, 1.35 mmol), and 1,1'-bis(diphenylphosphino)ferrocene palladium dichloride (49.34 mg, 67.44 μmol) were added in sequence. The reaction mixture was stirred at 90° C. under nitrogen protection for 16 hours. After the reaction was completed, the reaction solution was concentrated under reduced pressure. Water was added (30 ml), and the mixture was extracted with ethyl acetate (15 ml×3). The organic phases were combined, dried with anhydrous sodium sulfate, filtered, and concentrated under reduced pressure. The residue was isolated by thin-layer chromatography and then isolated by high-performance liquid chromatography (formic acid condition) to give compound 27.

$^1$H NMR (400 MHz, CD$_3$OD) δ ppm 8.51-8.60 (m, 2H), 7.89 (d, J=1.3 Hz, 1H), 7.66-7.83 (m, 6H), 7.49 (s, 1H), 7.36-7.45 (m, 2H), 6.74-7.06 (m, 1H), 4.88-4.89 (m, 2H), 2.64 (s, 3H), 2.37 (s, 3H). MS-ESI Calculated [M+H]$^+$ 457, Found 457.

Example 28

Route for Synthesis:

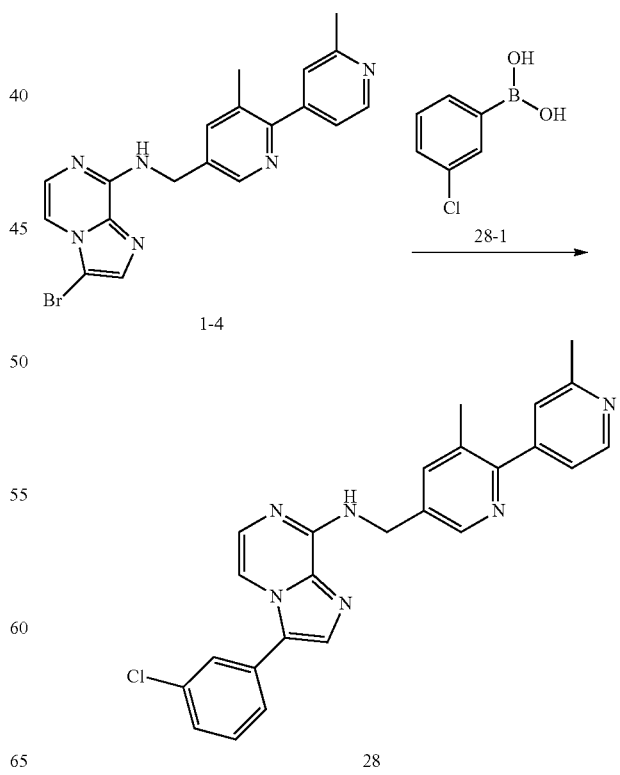

Compound 1-4 (200 mg, 488.46 mmol), compound 28-1 (114.62 mg, 732.99 μmol), 1,1'-bis(diphenylphosphino)ferrocene palladium dichloride (35.76 mg, 48.87 μmol) and potassium carbonate (202.61 mg, 1.47 mmol) were dissolved in dioxane (2 ml) and water (0.5 ml), and reacted at 90° C. for 12 hours. After the reaction was completed, the reaction mixture was diluted with water (20 ml), and the mixture was extracted with ethyl acetate (20 ml×3). The combined organic phase was dried with anhydrous sodium sulfate, filtered and concentrated. The concentrate was prepared by a preparative plate (dichloromethane:methanol=10:1) to give a crude product. The crude product was purified by high-performance liquid chromatography (hydrochloric acid condition) to give the hydrochloride salt of compound 28.

$^1$H NMR (400 MHz, CD$_3$OD) δ ppm 8.82 (d, J=6.1 Hz, 1H), 8.76 (d, J=1.2 Hz, 1H), 8.19 (s, 1H), 8.13 (dd, J=1.3, 6.2 Hz, 1H), 8.04 (s, 1H), 7.95-8.01 (m, 2H), 7.76 (d, J=1.3 Hz, 1H), 7.57-7.67 (m, 3H), 7.33 (d, J=5.6 Hz, 1H), 5.07 (br s, 2H), 2.90 (s, 3H), 2.53 (s, 3H). MS-ESI Calculated [M+H]$^+$ 441, Found 441.

Example 29

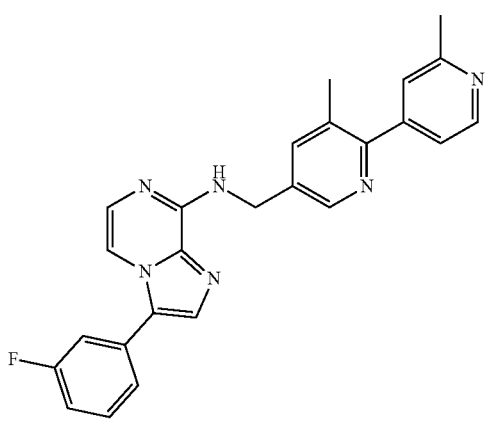

29

Route for Synthesis:

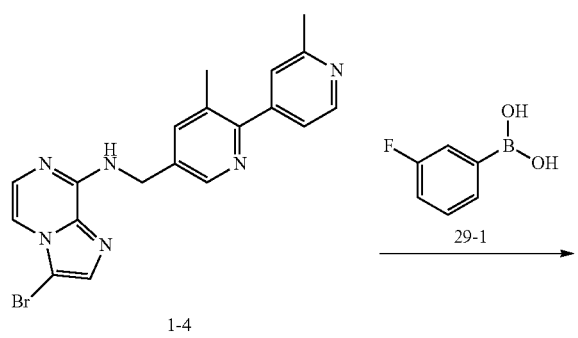

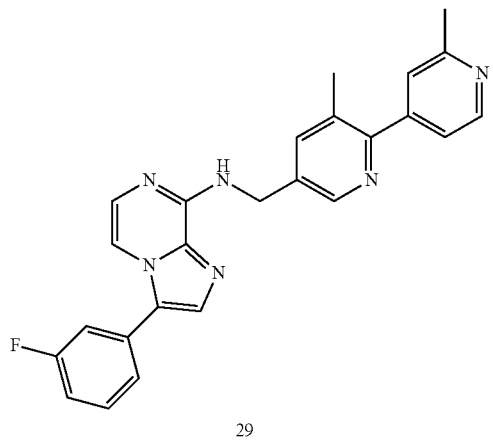

29

Compound 1-4 (150 mg, 366.50 μmol), compound 29-1 (76.92 mg, 549.74 μmol), 1,1'-bis(diphenylphosphino)ferrocene palladium dichloride (6.82 mg, 36.65 μmol) and potassium carbonate (151.96 mg, 1.10 mmol) were dissolved in dioxane (2 ml) and water (0.5 ml), and reacted at 90° C. for 12 hours. After the reaction was completed, the reaction mixture was diluted with water (20 ml), and the mixture was extracted with ethyl acetate (20 ml×3). The combined organic phase was dried with anhydrous sodium sulfate, filtered and concentrated. The concentrate was prepared by a preparative plate (dichloromethane:methanol=15:1) to give a crude product. The crude product was purified by high-performance liquid chromatography (hydrochloric acid condition) to give the hydrochloride salt of compound 29.

$^1$H NMR (400 MHz, CD$_3$OD) δ ppm 8.93-9.01 (m, 2H), 8.55 (br s, 1H), 8.32 (s, 1H), 8.26 (br d, J=6.0 Hz, 1H), 8.01-8.11 (m, 2H), 7.68 (dt, J=6.0, 7.9 Hz, 1H), 7.49-7.60 (m, 2H), 7.31-7.43 (m, 2H), 5.26 (br s, 2H), 2.96 (s, 3H), 2.57 (s, 3H). MS-ESI Calculated [M+H]$^+$ 425, Found 425.

Example 30

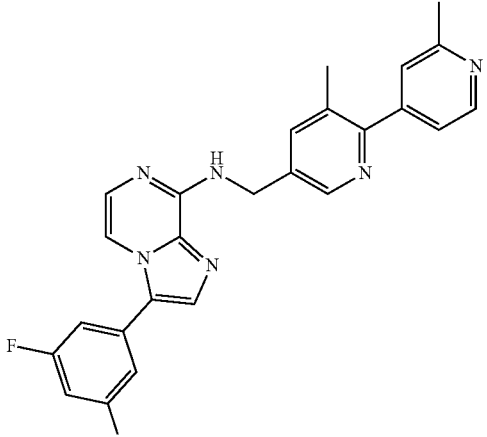

30

Route for Synthesis:

Example 31

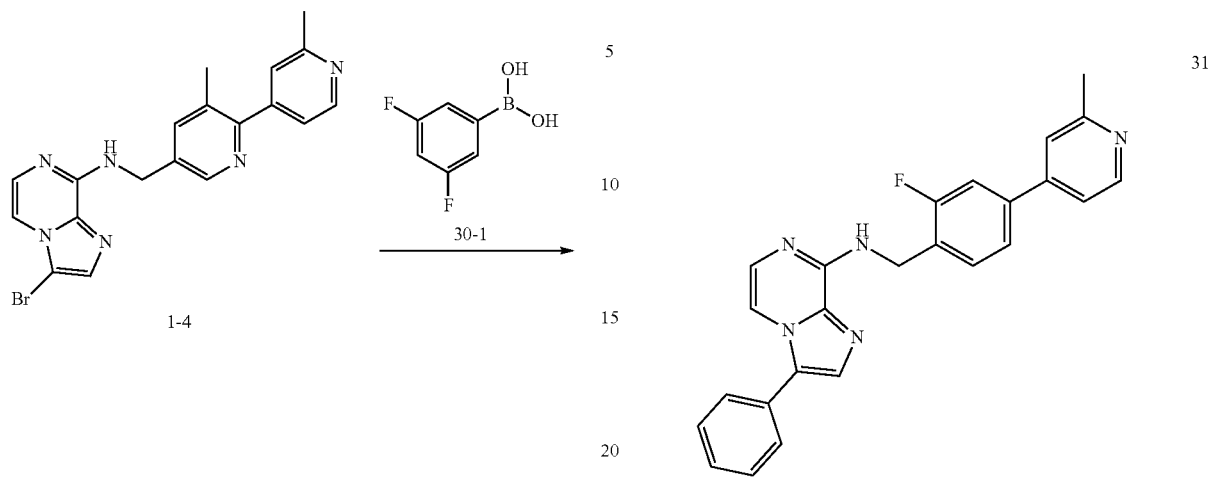

Route for Synthesis:

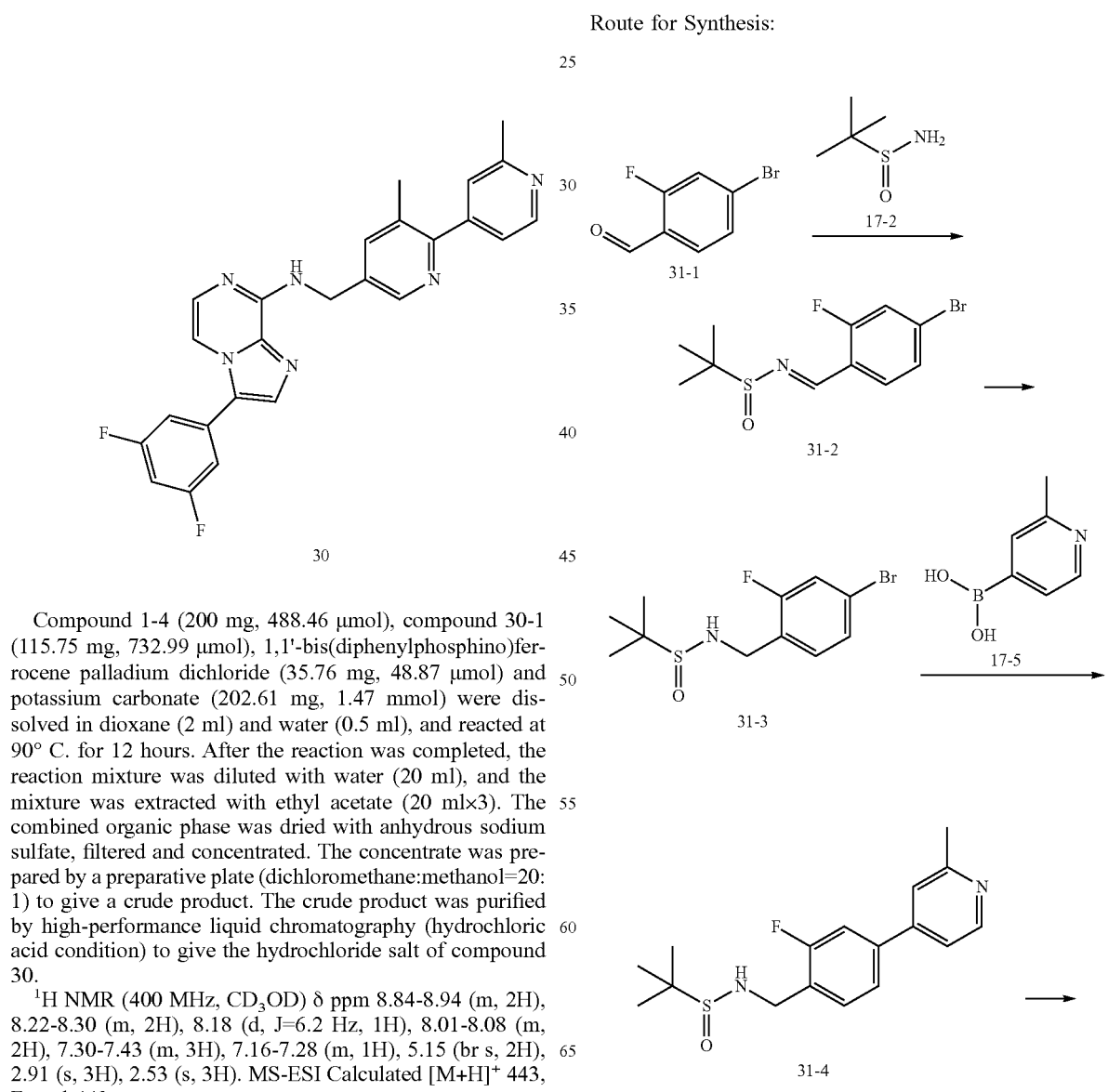

Compound 1-4 (200 mg, 488.46 μmol), compound 30-1 (115.75 mg, 732.99 μmol), 1,1'-bis(diphenylphosphino)ferrocene palladium dichloride (35.76 mg, 48.87 μmol) and potassium carbonate (202.61 mg, 1.47 mmol) were dissolved in dioxane (2 ml) and water (0.5 ml), and reacted at 90° C. for 12 hours. After the reaction was completed, the reaction mixture was diluted with water (20 ml), and the mixture was extracted with ethyl acetate (20 ml×3). The combined organic phase was dried with anhydrous sodium sulfate, filtered and concentrated. The concentrate was prepared by a preparative plate (dichloromethane:methanol=20:1) to give a crude product. The crude product was purified by high-performance liquid chromatography (hydrochloric acid condition) to give the hydrochloride salt of compound 30.

$^1$H NMR (400 MHz, CD$_3$OD) δ ppm 8.84-8.94 (m, 2H), 8.22-8.30 (m, 2H), 8.18 (d, J=6.2 Hz, 1H), 8.01-8.08 (m, 2H), 7.30-7.43 (m, 3H), 7.16-7.28 (m, 1H), 5.15 (br s, 2H), 2.91 (s, 3H), 2.53 (s, 3H). MS-ESI Calculated [M+H]$^+$ 443, Found 443.

-continued

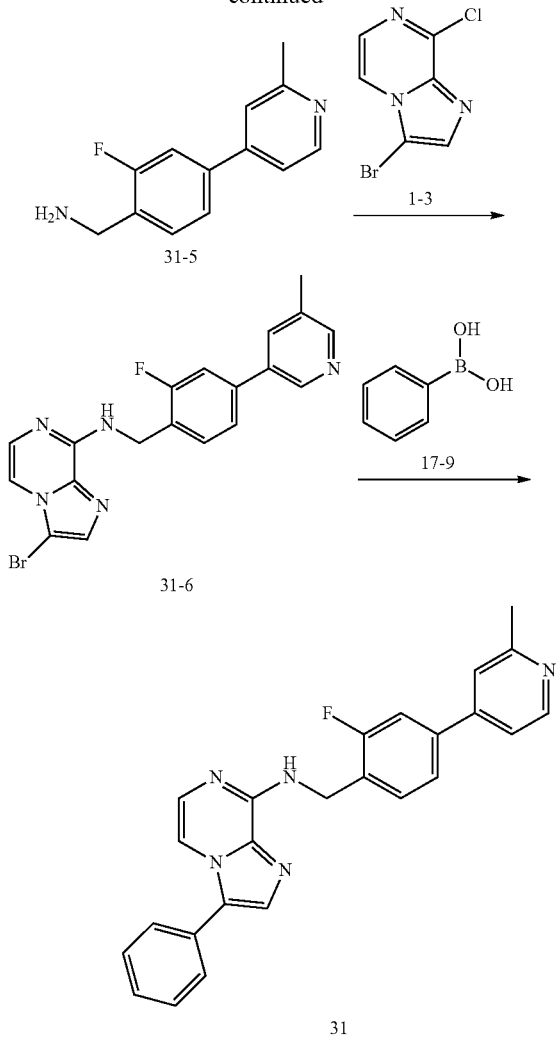

Step 1

Compound 31-1 (1 g, 4.93 mmol) and compound 17-2 (895.54 mg, 7.39 mmol) were dissolved in tetrahydrofuran (15 ml). Anhydrous copper sulfate (1.73 g, 10.84 mmol) was added to the reaction solution, and the reaction mixture was stirred at 80° C. for 16 hours. After the reaction was completed, the reaction mixture was diluted with water (20 ml), and the mixture was extracted with ethyl acetate (20 ml×2). The organic phase was washed with saturated sodium chloride solution (20 ml×2), dried with anhydrous sodium sulfate, and rotary evaporated to dryness to give crude product of compound 31-2. MS-ESI Calculated [M+H]$^+$ 307, Found 307.

Step 2

Compound 31-2 (1.27 g, 4.15 mmol) was dissolved in tetrahydrofuran (8 ml) and methanol (2 ml). Sodium borohydride (156.91 mg, 4.15 mmol) was added to the reaction solution at 0° C. and the reaction mixture was stirred at 25° C. for 1 hour. After the reaction was completed, the reaction mixture was diluted with water (20 ml), and the mixture was extracted with ethyl acetate (20 ml×2). The combined organic phase was washed with saturated sodium chloride solution (20 ml×2), dried with anhydrous sodium sulfate, filtered, and concentrated under reduced pressure to give crude product of compound 31-3. MS-ESI Calculated [M+H]$^+$ 309, Found 309.

Step 3

Compound 31-3 (1.3 g, 4.22 mmol), compound 17-5 (866.43 mg, 6.33 mmol), and potassium carbonate (1.75 g, 12.65 mmol) were dissolved in dioxane (20 ml) and water (2 ml). 1,1'-bis(diphenylphosphino)ferrocene palladium dichloride (462.94 mg, 632.69 μmol) was added to the reaction solution. The gas in the reaction mixture was replaced, and the reaction mixture was stirred at 80° C. under nitrogen protection for 16 hours. After the reaction was completed, the reaction mixture was diluted with water (20 ml), and the mixture was extracted with ethyl acetate (20 ml×2). The combined organic phase was washed with saturated sodium chloride solution (20 ml×2), dried with anhydrous sodium sulfate, filtered, and concentrated under reduced pressure. The residue was purified by silica gel column chromatography to give compound 31-4. MS-ESI Calculated [M+H]$^+$ 321, Found 321.

Step 4

Compound 31-4 (0.825 g, 2.57 mmol) was dissolved in ethyl acetate (10 ml) and methanol (2.5 ml). Hydrochloric acid/ethyl acetate (4 M, 16.74 ml) was added to the reaction solution, and the reaction mixture was stirred at 25° C. for 12 hours. After the reaction was completed, ethyl acetate (20 ml) was added, and the mixture was filtered. The filter cake was stirred in ethyl acetate (20 ml) at room temperature for 30 minutes to give compound 31-5.
MS-ESI Calculated [M+H]$^+$ 217, Found 217.

Step 5

Compound 31-5 (500 mg, 2.31 mmol) was dissolved in N-methylpyrrolidone (10 ml). Compound 1-3 (644.98 mg, 2.77 mmol) and N,N-diisopropylethylamine (1.79 g, 13.87 mmol) were added to the reaction solution and the reaction mixture was stirred at 130° C. for 4 hours. After the reaction was completed, the reaction mixture was diluted with water (20 ml), and the mixture was extracted with ethyl acetate (20 ml×2). The combined organic phase was washed with saturated sodium chloride solution (20 ml×2), dried with anhydrous sodium sulfate, filtered, and concentrated under reduced pressure. The residue was purified by silica gel column chromatography to give compound 31-6.
MS-ESI Calculated [M+H]$^+$ 413, Found 413.

Step 6

Compound 31-6 (200 mg, 485.13 μmol) and compound 17-9 (118.30 mg, 970.27 μmol) were dissolved in dioxane (10 ml) and water (1 ml). 1,1'-bis(diphenylphosphino)ferrocene palladium dichloride (53.25 mg, 72.77 μmol) and potassium carbonate (201.14 mg, 1.46 mmol) were added to the reaction solution. The gas in the reaction mixture was replaced, and the reaction mixture was stirred at 80° C. under nitrogen protection for 15 hours. After the reaction was completed, the reaction solution was diluted with water (20 ml), and extracted with ethyl acetate (20 ml×2). The organic phase was washed with saturated sodium chloride solution (20 ml×2), and purified by thin-layer chromatography and high-performance liquid chromatography (trifluoroacetic acid condition) to give compound 31.
¹H NMR (400 MHz, CD₃OD) δ ppm 8.46 (d, J=5.4 Hz, 1H), 7.78 (d, J=4.8 Hz, 1H), 7.45-7.70 (m, 11H), 7.36 (d, J=4.8 Hz, 1H), 4.92 (s, 2H), 2.61 (s, 3H). MS-ESI Calculated [M+H]⁺ 410, Found 410.
Example 32
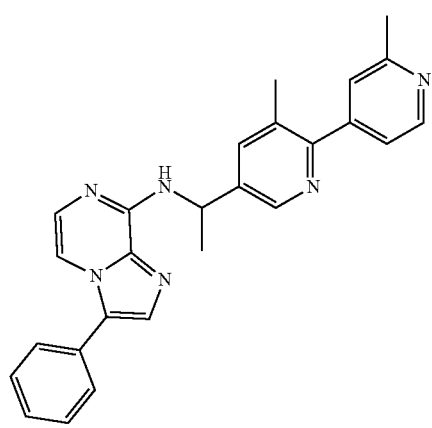
Route for Synthesis:
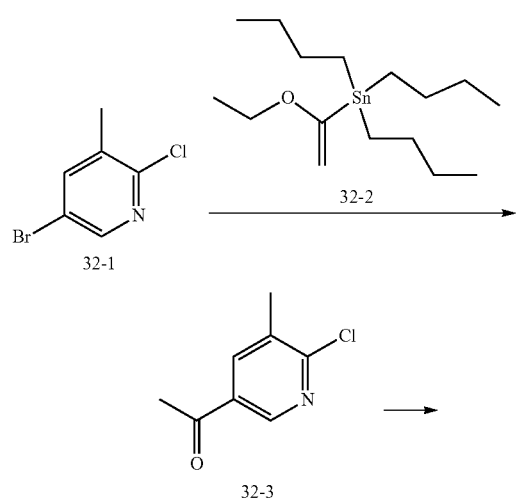
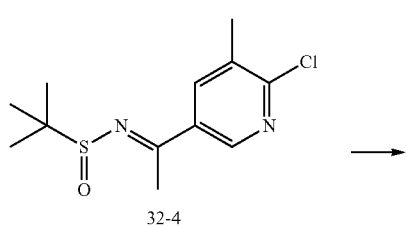
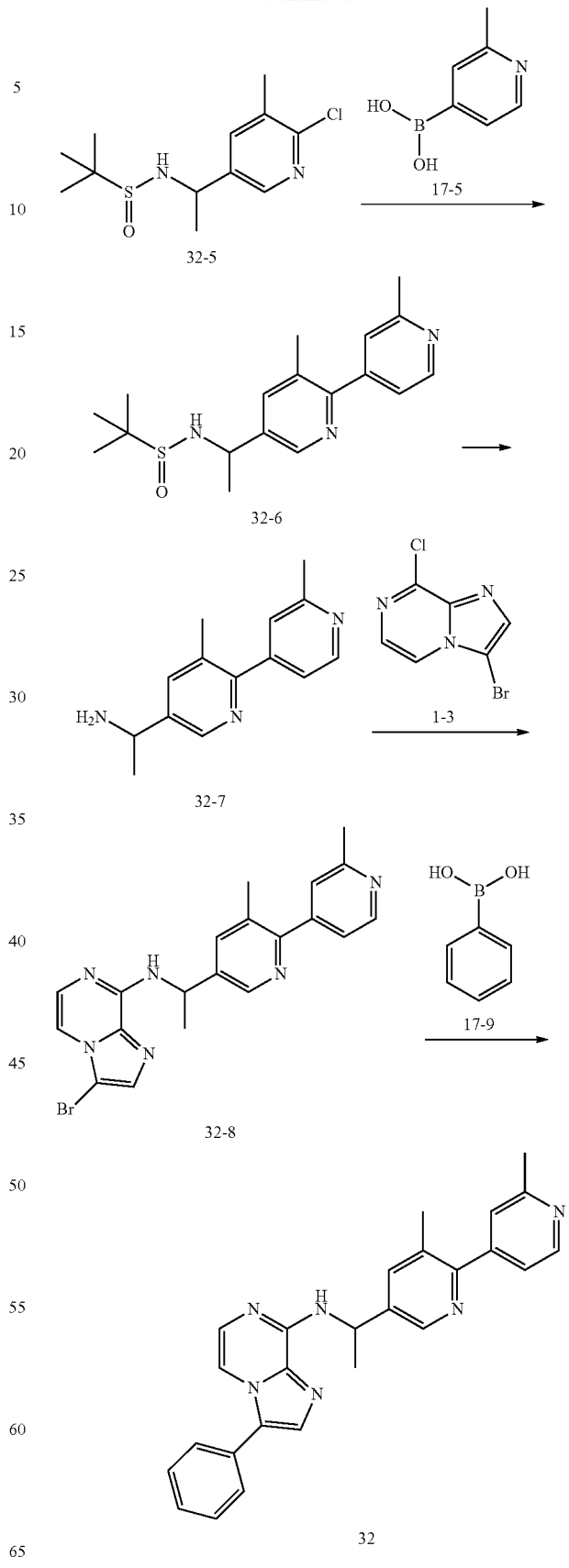

Step 1

Compound 32-1 (5 g, 24.22 mmol) and compound 32-2 (6.12 g, 16.95 mmol) were dissolved in dioxane (100 ml). Tetrakis(triphenylphosphine)palladium (1.40 g, 1.21 mmol) and triethylamine (3.68 g, 36.33 mmol) were added and the mixture was reacted at 80° C. for 12 hours. After the reaction was completed, aqueous potassium fluoride solution (100 ml) was added, and the mixture was extracted with ethyl acetate (100 ml×3). The combined organic phase was dried with anhydrous sodium sulfate, filtered and concentrated. The concentrate was dissolved in dioxane (100 ml). Hydrochloric acid (1 mol/L, 100 ml) was added, and the mixture was reacted at 20° C. for 12 hours. After the reaction was completed, the reaction solution was extracted with ethyl acetate (100 ml×3). The combined organic phase was dried with anhydrous sodium sulfate, filtered and concentrated. The concentrate was purified by column chromatography to give compound 32-3. MS-ESI Calculated $[M+H]^+$ 170, Found 170.

Step 2

Compound 32-3 (2.2 g, 12.97 mmol), 2-methyl-2-propanesulfonimide (2.36 g, 19.46 mmol), and tetraethyl titanate (8.88 g, 38.91 mmol) were dissolved in tetrahydrofuran (100 ml). The atmosphere was replaced 3 times with nitrogen, and the mixture was reacted at 80° C. for 12 hours. After the reaction was completed, the reaction mixture was diluted with water (100 ml), and the mixture was extracted with ethyl acetate (100 ml×3). The combined organic phase was dried with anhydrous sodium sulfate, filtered, and concentrated to give compound 32-4. MS-ESI Calculated $[M+H]^+$ 273, Found 273.

Step 3

Compound 32-4 (4.2 g, 15.40 mmol) was dissolved in methanol (100 ml). Sodium borohydride (1.16 g, 30.79 mmol) was added at 0° C., and the mixture was reacted at 0° C. for 5 hours. After the reaction was completed, the reaction mixture was diluted with water (50 ml), and the mixture was extracted with ethyl acetate (50 ml×3). The combined organic phase was dried with anhydrous sodium sulfate, filtered and concentrated. The concentrate was purified by column chromatography to give compound 32-5.
MS-ESI Calculated $[M+H]^+$ 275, Found 275.

Step 4

Compound 32-5 (1.5 g, 5.46 mmol), compound 17-5 (1.12 g, 8.19 mmol), potassium carbonate (2.26 g, 16.37 mmol), and 1,1'-bis(di-tert-butylphosphino)ferrocene palladium dichloride (355.74 mg, 545.83 μmol) were dissolved in dioxane (30 ml) and water (6 ml). The atmosphere was replaced 3 times with nitrogen, and the mixture was reacted at 80° C. for 12 hours. After the reaction was completed, the reaction mixture was diluted with water (50 ml), and the mixture was extracted with ethyl acetate (50 ml×3). The combined organic phase was dried with anhydrous sodium sulfate, filtered and concentrated. The concentrate was purified by column chromatography to give compound 32-6. MS-ESI Calculated $[M+H]^+$ 332, Found 332.

Step 5

Compound 32-6 (1.7 g, 5.13 mmol) was added to a solution of hydrogen chloride in ethyl acetate (4 mol/L, 42.50 ml), and reacted at 20° C. for 1 hour. After the reaction was completed, the reaction solution was rotary evaporated to dryness to give compound 32-7. MS-ESI Calculated $[M+H]^+$ 228, Found 228.

Step 6

Compound 32-7 (500 mg, 1.90 mmol), compound 1-3 (352.53 mg, 1.52 mmol), and N,N-diisopropylethylamine (979.99 mg, 7.58 mmol) were dissolved in N-methylpyrrolidone (5 ml). The atmosphere was replaced 3 times with nitrogen, and the mixture was reacted at 120° C. for 5 hours. After the reaction was completed, the reaction mixture was diluted with water (20 ml), and the mixture was extracted with ethyl acetate (20 ml×3). The combined organic phase was dried with anhydrous sodium sulfate, filtered and concentrated. The concentrate was purified by column chromatography to give compound 32-8. MS-ESI Calculated $[M+H]^+$ 424, Found 424.

Step 7

Compound 32-8 (300 mg, 708.70 μmol), compound 17-9 (129.62 mg, 1.06 mmol), 1,1'-bis(diphenylphosphino)ferrocene palladium dichloride (51.86 mg, 70.87 μmol), and potassium carbonate (293.84 mg, 2.13 mmol) were dissolved in dioxane (5 ml) and water (1 ml). The atmosphere was replaced 3 times with nitrogen, and the mixture was reacted at 90° C. for 12 hours. After the reaction was completed, the reaction mixture was diluted with water (20 ml), and the mixture was extracted with ethyl acetate (20 ml×3). The combined organic phase was dried with anhydrous sodium sulfate, filtered and concentrated. The concentrate was purified by thin-layer chromatography to give a crude product, and the crude product was purified by high-performance liquid chromatography (hydrochloric acid condition) to give the hydrochloride salt of compound 32.
$^1$H NMR (400 MHz, CD$_3$OD) δ ppm 9.03 (d, J=1.1 Hz, 1H), 8.95 (d, J=6.1 Hz, 1H), 8.61 (s, 1H), 8.29 (s, 1H), 8.23 (d, J=6.1 Hz, 1H), 8.08 (s, 1H), 7.98 (d, J=5.5 Hz, 1H), 7.67-7.73 (m, 2H), 7.56-7.65 (m, 3H), 7.43 (d, J=5.4 Hz, 1H), 5.42-5.96 (m, 1H), 2.94 (s, 3H), 2.55 (s, 3H), 1.93 (d, J=6.8 Hz, 3H). MS-ESI Calculated $[M+H]^+$ 421, Found 421.

Example 33

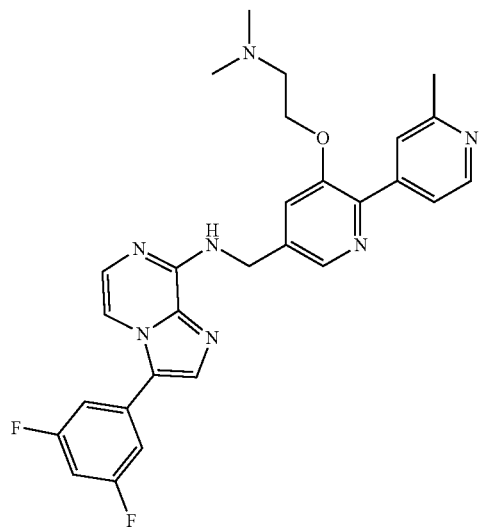

33

Route for Synthesis:
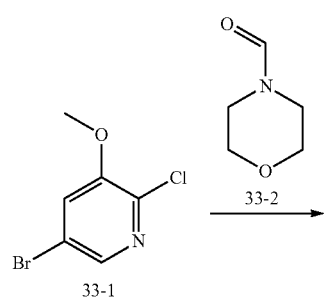
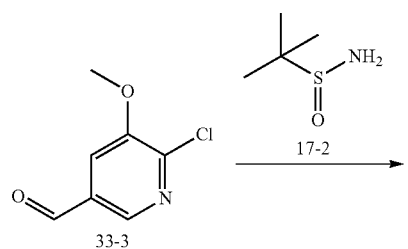
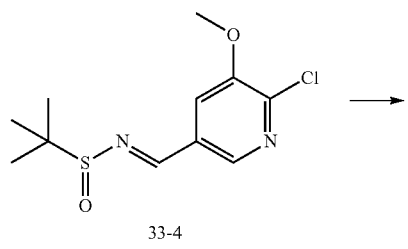
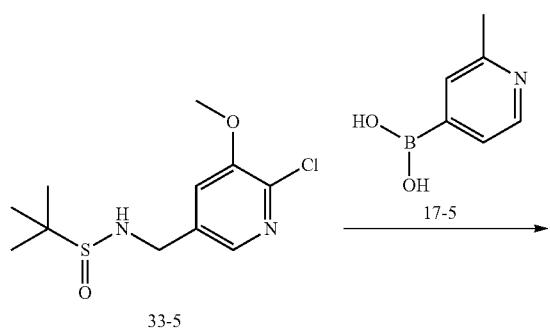
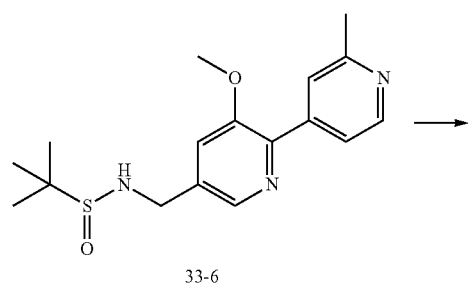
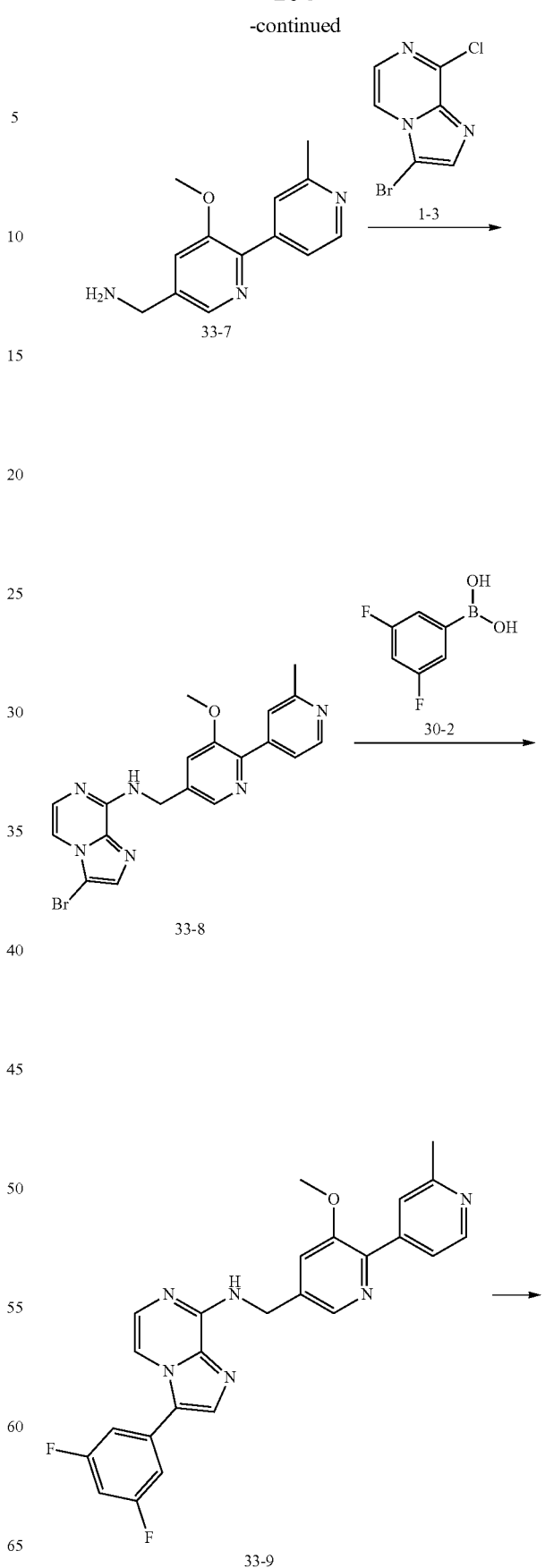

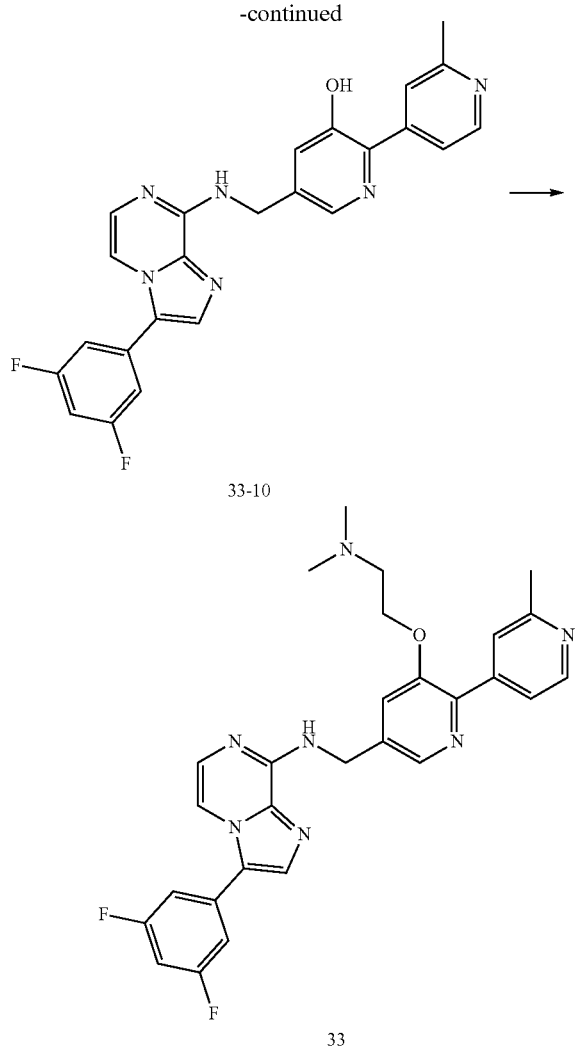

completed, the reaction solution was filtered and concentrated to give crude product of compound 33-4. MS-ESI Calculated [M+H]⁺ 275, Found 275.

Step 3

Compound 33-4 (15.6 g, 56.78 mmol) was dissolved in tetrahydrofuran (60 ml) and methanol (15 ml). Sodium borohydride (2.15 g, 56.78 mmol) was added to the reaction solution at 0° C. and the reaction mixture was stirred at 25° C. for 2 hours. After the reaction was completed, the reaction mixture was diluted with water (20 ml), and the mixture was extracted with ethyl acetate (30 ml×3). The combined organic phase was washed with saturated sodium chloride solution (20 ml×2), dried with anhydrous sodium sulfate, filtered, and concentrated under reduced pressure. The residue was purified by silica gel column chromatography to give product 33-5. MS-ESI Calculated [M+H]⁺ 277, Found 277.

Step 4

Compound 33-5 (3.7 g, 13.37 mmol), compound 17-5 (2.75 g, 20.05 mmol), and potassium carbonate (5.54 g, 40.10 mmol) were dissolved in dioxane (40 ml) and water (4 ml), and 1,1'-bis(diphenylphosphino)ferrocene palladium dichloride (1.47 g, 2.01 mmol) was added to the reaction solution. The gas in the reaction mixture was replaced, and the reaction mixture was stirred at 80° C. under nitrogen protection for 12 hours. After the reaction was completed, the reaction mixture was diluted with water (20 ml), and the mixture was extracted with ethyl acetate (20 ml×2). The combined organic phase was washed with saturated sodium chloride solution (20 ml×2), dried with anhydrous sodium sulfate, filtered, and concentrated under reduced pressure. The residue was purified by silica gel column chromatography to give compound 33-6.
MS-ESI Calculated [M+H]⁺ 334, Found 334.

Step 1

Compound 33-1 (9 g, 40.46 mmol) was dissolved in tetrahydrofuran (30 ml), and isopropylmagnesium chloride lithium chloride complex (1.3 mol/L, 34.23 ml) was added to the reaction solution at 0° C. After reacting for 1 hour, compound 33-2 (4.66 g, 40.46 mmol) was added and the mixture was reacted at 25° C. for 1 hour. After the reaction was completed, the reaction solution was concentrated. Water was added (20 ml), and the mixture was extracted with ethyl acetate (30 ml×3). The organic phase was washed with saturated sodium chloride solution (20 ml×2), dried with anhydrous sodium sulfate, and rotary evaporated to dryness to give crude product of compound 33-3.
MS-ESI Calculated [M+H]⁺ 172, Found 172.

Step 5

Compound 33-6 (4.36 g, 13.08 mmol) was dissolved in tetrahydrofuran (40 ml) and methanol (10 ml). Hydrochloric acid/ethyl acetate (4 M, 84.99 ml) was added to the reaction solution, and the reaction mixture was stirred at 25° C. for 12 hours. After the reaction was completed, ethyl acetate (20 ml) was added, and the mixture was filtered. The filter cake was stirred in ethyl acetate (20 ml) at 25° C. for half an hour to give compound 33-7.
MS-ESI Calculated [M+H]⁺ 230, Found 230.

Step 2

Compound 33-3 (7.56 g, 44.06 mmol) and compound 17-2 (8.01 g, 66.09 mmol) were dissolved in tetrahydrofuran (80 ml). Anhydrous copper sulfate (15.47 g, 96.93 mmol) was added to the reaction solution, and the mixture was reacted at 80° C. for 12 hours. After the reaction was Step 6

Compound 33-7 (1 g, 4.36 mmol) was dissolved in N-methylpyrrolidone (20 ml). Compound 1-3 (1.01 g, 4.36 mmol) and DIEA (2.25 g, 17.45 mmol) were added to the reaction solution, and the reaction mixture was stirred at 130° C. for 12 hours. After the reaction was completed, the reaction mixture was diluted with water (20 ml), and the mixture was extracted with ethyl acetate (30 ml×3). The combined organic phase was washed with saturated sodium chloride solution (20 ml×2), dried with anhydrous sodium sulfate, filtered, and concentrated under reduced pressure. The residue was purified by silica gel column chromatography to give compound 33-8.

MS-ESI Calculated [M+H]$^+$ 426, Found 426.

Step 7

Compound 33-8 (0.85 g, 2.00 mmol) and compound 30-2 (473.42 mg, 3.00 mmol) were dissolved in dioxane (15 ml) and water (1.5 ml), and 1,1'-bis(diphenylphosphino)ferrocene palladium dichloride (219.37 mg, 299.80 µmol) and potassium carbonate (828.71 mg, 6.00 mmol) were added to the reaction solution. The gas in the reaction mixture was replaced, and the reaction mixture was stirred at 80° C. under nitrogen protection for 16 hours. After the reaction was completed, the reaction solution was diluted with water (20 ml), and extracted with ethyl acetate (20 ml×3). The organic phase was washed with saturated sodium chloride solution (20 ml×2), dried with anhydrous sodium sulfate, and concentrated. The concentrate was purified by thin-layer chromatography to give compound 33-9. MS-ESI Calculated [M+H]$^+$ 459, Found 459.

Step 8

Compound 33-9 (0.85 g, 2.00 mmol) and tetrabutylammonium bromide (473.42 mg, 3.00 mmol) were dissolved in aqueous hydrogen bromide solution (107.28 g, 636.43 mmol), and the reaction mixture was stirred at 130° C. for 24 hours. After the reaction was completed, the reaction solution was diluted with water (10 ml), and 1 M sodium hydroxide was added to adjust the pH to 7. The mixture was extracted with ethyl acetate (20 ml×3). The organic phase was washed with saturated sodium chloride solution (20 ml×2), dried with anhydrous sodium sulfate, and concentrated to give compound 33-10. MS-ESI Calculated [M+H]$^+$ 445, Found 445.

Step 9

Compound 33-10 (420 mg, 945.02 µmol) and N,N-dimethyl-2-bromo-ethanamine (330.21 mg, 1.42 mmol, HBr) were dissolved in N,N-dimethylacetamide (15 ml), and cesium carbonate (1.54 g, 4.73 mmol) was added to the reaction solution. The gas in the reaction mixture was replaced, and the mixture was stirred at 25° C. for 12 hours. After the reaction was completed, the reaction solution was filtered and purified by high-performance liquid chromatography (ammonium bicarbonate condition) to give compound 33.

$^1$H NMR (400 MHz, CDCl$_3$) δ ppm 8.57 (d, J=5.3 Hz, 1H), 8.42 (d, J=1.6 Hz, 1H), 7.81 (s, 1H), 7.74 (d, J=4.9 Hz, 1H), 7.63-7.68 (m, 2H), 7.48 (d, J=4.8 Hz, 1H), 7.45 (d, J=1.6 Hz, 1H), 7.15-7.09 (m, 2H), 6.93 (tt, J=2.3, 8.8 Hz, 1H), 6.47 (br t, J=5.9 Hz, 1H), 4.92 (d, J=6.1 Hz, 2H), 4.14 (t, J=5.8 Hz, 2H), 2.76 (t, J=5.7 Hz, 2H), 2.64 (s, 3H), 2.32 (s, 6H). MS-ESI Calculated [M+H]$^+$ 516, Found 516.

Example 34

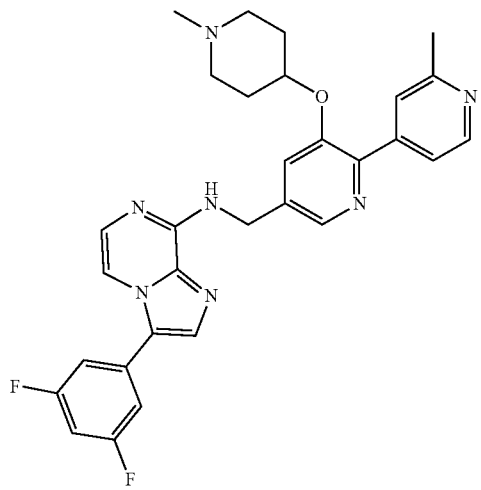

Route for Synthesis:

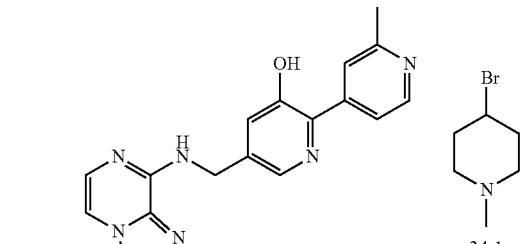

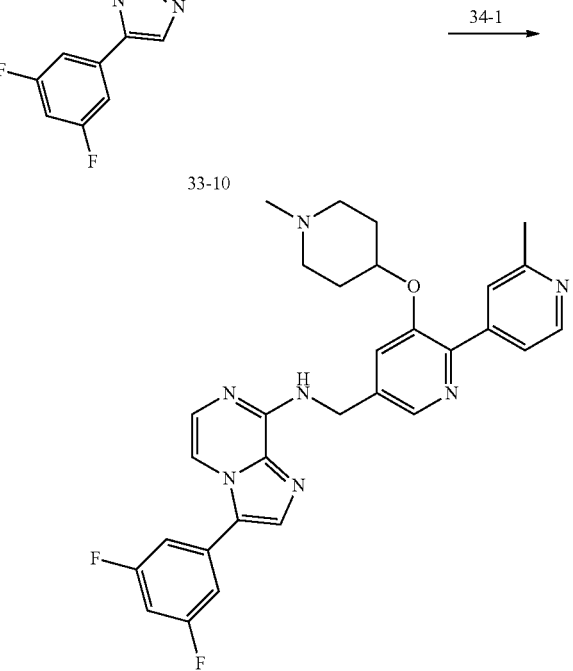

Compound 33-10 (280 mg, 630 µmol) and compound 34-1 (168 mg, 945 µmol) were dissolved in N,N-dimethylacetamide (15 ml), and cesium carbonate (1.03 g, 3.15 mmol) was added to the reaction solution. The gas in the reaction mixture was replaced, and the mixture was stirred at 25° C. for 12 hours. After the reaction was completed, the reaction solution was filtered and purified by high-performance liquid chromatography (ammonium bicarbonate condition) to give compound 34.

$^1$H NMR (400 MHz, CDCl$_3$) δ ppm 8.48 (d, J=5.3 Hz, 1H), 8.32 (d, J=1.6 Hz, 1H), 7.68 (s, 1H), 7.61 (dd, J=1.2, 5.3 Hz, 1H), 7.53-7.58 (m, 2H), 7.36-7.40 (m, 2H), 6.99-7.04 (m, 2H), 6.83 (tt, J=2.4, 8.8 Hz, 1H), 6.42 (br t, J=6.2 Hz, 1H), 4.80 (d, J=6.1 Hz, 2H), 4.36 (br d, J=3.3 Hz, 1H), 2.55 (s, 3H), 2.38-2.49 (m, 2H), 2.26 (br d, J=4.4 Hz, 2H), 2.19 (s, 3H), 1.84-1.95 (m, 2H), 1.78 (dt, J=3.7, 6.6 Hz, 2H). MS-ESI Calculated [M+H]$^+$ 542, Found 542.

Example 35

Route for Synthesis:

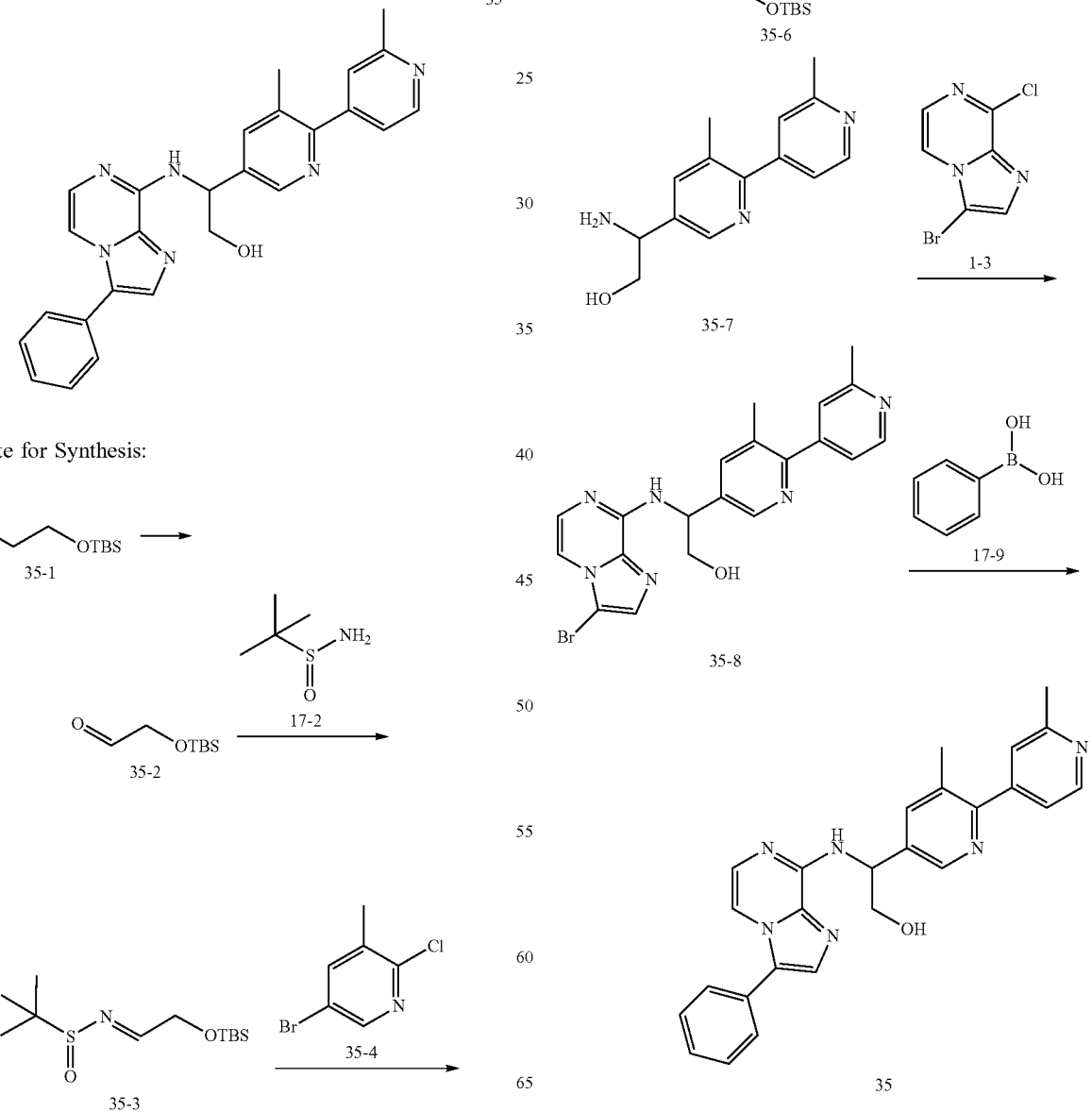

Step 1

Compound 35-1 (15.2 g, 86.20 mmol) was dissolved in dichloromethane (100 ml), and Dess-Martin (40.22 g, 94.82 mmol) was added to the reaction solution at 0° C. The gas in the reaction mixture was replaced, and the reaction mixture was stirred at 25° C. under nitrogen protection for 3 hours. After the reaction was completed, the reaction mixture was diluted with water (6 ml), adjusted to pH 7-8 with saturated aqueous sodium bicarbonate solution, and extracted with dichloromethane (30 ml×3). The organic phase was washed with saturated sodium chloride solution (40 ml×2), dried with anhydrous sodium sulfate, and rotary evaporated to dryness. The residue was purified by silica gel column chromatography to give crude product 35-2.

Step 2

Compound 35-2 (10 g, 57.37 mmol) and compound 17-2 (10.43 g, 86.05 mmol) were dissolved in dichloromethane (100 ml). Anhydrous copper sulfate (27.47 g, 172.11 mmol) was added to the reaction solution, and the reaction mixture was stirred at 25° C. for 24 hours. After the reaction was completed, the reaction mixture was diluted with water (20 ml), and the mixture was extracted with ethyl acetate (20 ml×2). The organic phase was washed with saturated sodium chloride solution (20 ml×2), dried with anhydrous sodium sulfate, and rotary evaporated to dryness. The residue was purified by silica gel column chromatography to give compound 35-3. MS-ESI Calculated $[M+H]^+$ 278, Found 278.

Step 3

Compound 35-3 (3.10 g, 15.02 mmol) was dissolved in tetrahydrofuran (20 ml), and the atmosphere was replaced with nitrogen. n-Butyl lithium (2.5 M, 6.61 ml) was added dropwise to the reaction solution at −78° C. The reaction mixture was stirred at −78° C. for 1 hour, and then compound 35-4 (5 g, 18.02 mmol) dissolved in tetrahydrofuran (20 ml) was added. After the reaction was completed, the reaction mixture was diluted with water (20 ml×2), and the mixture was extracted with ethyl acetate (30 ml×3). The combined organic phase was washed with saturated sodium chloride solution (20 ml×2), dried with anhydrous sodium sulfate, filtered, and concentrated under reduced pressure. The residue was purified by silica gel column chromatography to give crude product 35-5. MS-ESI Calculated $[M+H]^+$ 406, Found 406.

Step 4

Compound 35-5 (2.8 g, 6.91 mmol), compound 17-5 (1.42 g, 10.37 mmol), and potassium phosphate (4.40 g, 20.74 mmol) were dissolved in tetrahydrofuran (24 ml) and water (6 ml), and dibutyl(cyclopentyl)phosphine palladium dichloride (901.03 mg, 1.38 mmol) was added to the reaction solution. The gas in the reaction mixture was replaced, and the reaction mixture was stirred at 100° C. under nitrogen protection for 12 hours. After the reaction was completed, the reaction mixture was diluted with water (30 ml), and the mixture was extracted with ethyl acetate (30 ml×3). The combined organic phase was washed with saturated sodium chloride solution (20 ml×2), dried with anhydrous sodium sulfate, filtered, and concentrated under reduced pressure. The residue was purified by silica gel column chromatography to give compound 35-6. MS-ESI Calculated $[M+H]^+$ 462, Found 462.

Step 5

Compound 35-6 (2 g, 4.33 mmol) was dissolved in ethyl acetate (20 ml) and methanol (5 ml). Hydrochloric acid/ethyl acetate (4 M, 28.15 ml) was added to the reaction solution, and the reaction mixture was stirred at 25° C. for 12 hours. After the reaction was completed, ethyl acetate (20 ml) was added, and the mixture was filtered. The filter cake was stirred in ethyl acetate (20 ml) at room temperature for 30 minutes to give compound 35-7.

MS-ESI Calculated $[M+H]^+$ 244, Found 244.

Step 6

Compound 35-7 (1.4 g, 5.75 mmol) was dissolved in N-methylpyrrolidone (40 ml).

Compound 1-3 (1.47 g, 6.33 mmol) and N,N-diisopropylethylamine (2.97 g, 23.02 mmol) were added to the reaction solution, and the reaction mixture was stirred at 130° C. for 4 hours. After the reaction was completed, the reaction mixture was diluted with water (10 ml), and the mixture was extracted with ethyl acetate (20 ml×3). The combined organic phase was washed with saturated sodium chloride solution (20 ml×2), dried with anhydrous sodium sulfate, filtered, and concentrated under reduced pressure. The residue was purified by silica gel column chromatography to give compound 35-8.

MS-ESI Calculated $[M+H]^+$ 440, Found 440.

Step 7

Compound 35-8 (240 mg, 546.31 μmol) and compound 17-9 (99.92 mg, 819.47 μmol) were dissolved in dioxane (10 ml) and water (1 ml), and 1,1'-bis(diphenylphosphino)ferrocene palladium dichloride (59.96 mg, 81.95 μmol) and potassium carbonate (226.51 mg, 1.64 mmol) were added to the reaction solution. The gas in the reaction mixture was replaced, and the reaction mixture was stirred at 70° C. under nitrogen protection for 12 hours. After the reaction was completed, the reaction solution was diluted with water (20 ml), and extracted with ethyl acetate (30 ml×3). The organic phase was washed with saturated sodium chloride solution (20 ml×2), and purified by thin-layer chromatography and high-performance liquid chromatography (formic acid condition) to give compound 35.

$^1$H NMR (400 MHz, CD$_3$OD) δ ppm 8.60 (d, J=1.6 Hz, 1H), 8.52 (d, J=5.3 Hz, 1H), 7.94 (d, J=1.5 Hz, 1H), 7.78 (d, J=4.8 Hz, 1H), 7.71 (s, 1H), 7.61-7.67 (m, 2H), 7.58 (br t, J=7.7 Hz, 2H), 7.47-7.53 (m, 1H), 7.45 (s, 1H), 7.38 (br d, J=4.2 Hz, 1H), 7.32 (d, J=4.9 Hz, 1H), 5.44 (t, J=5.4 Hz, 1H), 3.98-4.10 (m, 2H), 2.62 (s, 3H), 2.37 (s, 3H). MS-ESI Calculated $[M+H]^+$ 437, Found 437.

Example 36

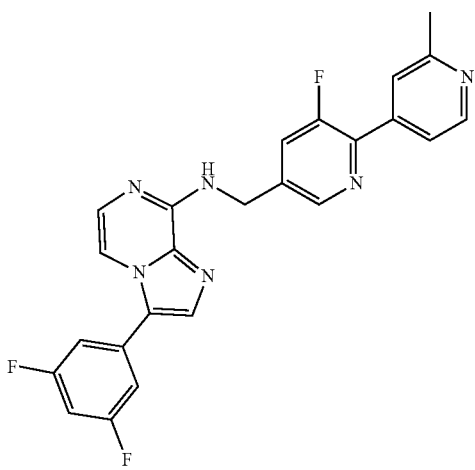

Route for Synthesis:

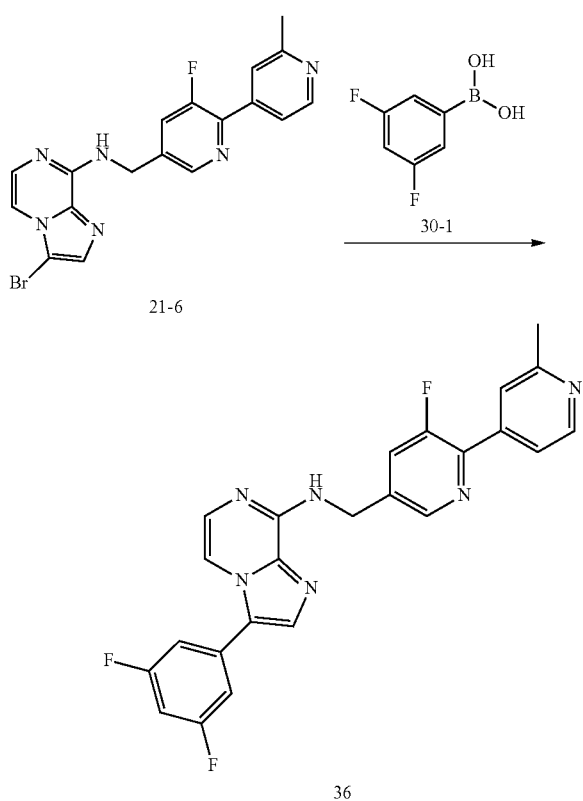

Compound 21-6 (280 mg, 677.56 μmol) and compound 30-1 (160.49 mg, 1.02 mmol) were dissolved in dioxane (10 ml) and water (1 ml), and 1,1'-bis(diphenylphosphino)ferrocene palladium dichloride (74.37 mg, 101.63 μmol) and potassium carbonate (280.94 mg, 2.03 mmol) were added to the reaction solution. The gas in the reaction mixture was replaced, and the reaction mixture was stirred at 80° C. under nitrogen protection for 16 hours. After the reaction was completed, the reaction solution was diluted with water (20 ml), and extracted with ethyl acetate (30 ml×3). The organic phase was washed with saturated sodium chloride solution (20 ml×2), and purified by thin-layer chromatography and high-performance liquid chromatography (formic acid condition) to give the formate salt of compound 36.

$^1$H NMR (400 MHz, DMSO-$d_6$) δ ppm 8.63 (t, J=1.7 Hz, 1H), 8.57 (d, J=5.1 Hz, 1H), 8.39-8.45 (m, 1H), 7.88-7.92 (m, 2H), 7.83 (dd, J=1.7, 12.3 Hz, 1H), 7.74 (s, 1H), 7.66 (d, J=5.1 Hz, 1H), 7.43-7.49 (m, 2H), 7.31-7.39 (m, 2H), 4.80 (d, J=6.4 Hz, 2H), 2.55 (s, 3H). MS-ESI Calculated [M+H]$^+$ 447, Found 447.

In Vitro Activity Assay

1. Assay of Inhibitory Activity on Super-Top-Flash (STF) Reporter Gene

HEK293 STF and L wnt3A cells were planted at a ratio of 1:1 in a white 96-well plate with 80 μL of cell suspension per well, which contained 20,000 HEK293 STF cells and 20,000 L wnt3A cells. The cell plate was placed in a carbon dioxide incubator for culture overnight.

The assay compound was serially diluted 5-fold with a discharge gun to the 8th concentration, that is, from 400 μM to 5.12 nM, in duplicate. 78 μL of medium was added to the middle plate, and then 2 μL of the serially diluted compound was transferred to each well of the middle plate according to the corresponding position. After mixing, 20 μL of the mixture was transferred to each well of the cell plate. The cell plate was placed in a carbon dioxide incubator for 24 hours.

100 μL of Promega Bright-Glo reagent was added to each well of the cell plate, and the cell plate was incubated at room temperature for 10 minutes to stabilize the luminescence signal. A multi-label analyzer was used to read results.

The original data of the multi-label analyzer was used for calculation, and the value of IC$_{50}$ can be obtained by curve fitting. Table 1 provides data of the inhibitory activity of the compounds of the present disclosure on the Wnt signaling pathway. The results show that the compounds of the present disclosure have a good inhibitory activity on the Porcupine of the Wnt signaling pathway.

TABLE 1

Assay results of inhibitory activity of example compounds of the present disclosure on STF reporter gene for WNT pathway

| Compound | IC$_{50}$(nM) | Compound | IC$_{50}$(nM) |
| --- | --- | --- | --- |
| Compound 1 | 0.12 | Compound 15 (formate) | 0.15 |
| Compound 2 | 0.12 | Compound 16 | <0.001 |
| Compound 3 | 0.96 | Compound 17 | 0.23 |
| Compound 4 | 0.14 | Compound 18 | 0.0128 |
| Compound 5 | 9.7 | Compound 19 | 0.017 |
| Compound 6 | 0.58 | Compound 20 | 0.4 |
| Compound 8 | 6.56 | Compound 25 (formate) | 3.44 |
| Compound 9 (formate) | 8.95 | Compound 26 | 13.05 |
| Compound 10 | 13.5 | Compound 27 | 4.15 |
| Compound 11 | 0.05 | Compound 28 (hydrochloride) | 0.86 |
| Compound 13 (formate) | 0.56 | Compound 29 (hydrochloride) | 0.38 |
| Compound 14 | <0.001 | Compound 30 (hydrochloride) | 0.52 |

2. Assay of Anti-Proliferative Activity on Capan-2 Cells

Capan-2 cells were planted in a white 96-well plate with 80 μL of cell suspension per well, which contained 5000 Capan-2 cells. The cell plate was placed in a carbon dioxide incubator for culture overnight.

The assay compound was serially diluted 3-fold with a discharge gun to the 9th concentration, that is, from 200 μM to 30 nM, in duplicate. 78 μL of medium was added to the middle plate, and then 2 μL of the serially diluted compound was transferred to each well of the middle plate according to the corresponding position. After mixing, 20 μL of the mixture was transferred to each well of the cell plate. The cell plate was incubated in a carbon dioxide incubator for 5 days. Another cell plate was prepared, and read on the day of drug addition. The signal value was used as the maximum value (The value of Max in the equation below) in data analysis. 25 μL of chemiluminescence detection reagent for cell viability was added to each well of this cell plate, and this cell plate was incubated at room temperature for 10 minutes to stabilize the luminescence signal. A multi-label analyzer was used to read results.

After the cell plate was cultured for 5 days, 25 μL of Promega CellTiter-Glo reagent was added to each well of the cell plate. The cell plate was incubated at room temperature for 10 minutes to stabilize the luminescence signal. A multi-label analyzer was used to read results.

The value of $IC_{50}$ can be obtained by curve fitting. Table 2 provides the inhibitory activity of the compounds of the present disclosure on Capan-2 cell proliferation. The results show that the compounds of the present disclosure have a good inhibitory activity on Capan-2 cell proliferation.

TABLE 2

Assay results of the anti-proliferative activity of the example compounds of the present disclosure on Capan-2 cells

| Compound | $IC_{50}$(nM) | Compound | $IC_{50}$(nM) |
|---|---|---|---|
| Compound 1 | 0.71 | Compound 23 | 0.74 |
| Compound 2 | 4.26 | Compound 25 (formate) | 8.98 |
| Compound 4 | 964 | Compound 26 | 3.82 |
| Compound 8 | 109.3 | Compound 28 (hydrochloride) | 1.43 |
| Compound 9 (formate) | 103.2 | Compound 29 (hydrochloride) | 0.35 |
| Compound 10 | >1000 | Compound 30 (hydrochloride) | 0.71 |
| Compound 17 | 1.45 | Compound 31 | 4.7 |
| Compound 18 | 19.12 | Compound 32 (hydrochloride) | 3.04 |
| Compound 19 | 4.61 | Compound 33 | 2.3 |
| Compound 20 | 18.5 | Compound 34 | 1.9 |
| Compound 21 | 0.43 | Compound 35 | 10.09 |
| Compound 22 (formate) | 1.24 | Compound 36 (formate) | 0.21 |

3. Assay of In Vivo Drug Efficacy on Capan-2 Transplanted Tumor in Nude Mice

Capan-2 cells were cultured in McCoy's 5A medium, containing 10% fetal bovine serum FBS, in a 37° C. incubator with 5% $CO_2$. Tumor cells were collected after passaging and growing to a suitable concentration and during the logarithmic growth phase. The cells resuspended in McCoy's 5A medium were counted and the cell suspension was adjusted to a concentration of $2 \times 10^7$/mL for inoculation.

Establishment of human pancreatic cancer Capan-2 xenograft tumor. Cells were collected and the concentration was adjusted to $2 \times 10^7$ (resuspend with McCoy's 5A medium to a cell suspension containing 50% Martigel). Under aseptic conditions, 0.1 mL of tumor cells was injected subcutaneously into the right back of the mouse, and the number of cells inoculated per mouse was $2 \times 10^6$. After the tumor was grown to a certain size, digital vernier calipers was used to measure the length (a) and width (b) of the tumor, and the tumor volume was calculated. The calculation formula of tumor volume (TV) was: $TV = a \times b^2/2$.

Capan-2 tumor cells were inoculated. When the tumor was grown to about 150 cubic millimeters, mice were divided into groups with 6 mice in each group. The day of grouping was regarded as day 0, and the drug was administered on the day of grouping. During the assay, the animal's body weight and tumor size were measured twice a week, and the animal's clinical symptoms were observed and recorded every day. For each administration, the most recently weighed animal body weight was referred to.

The evaluation index of anti-tumor activity is relative tumor proliferation rate T/C (%), wherein T/C (%)>40% means ineffective, and T/C (%)<40% and statistically P<0.05 means effective. The calculation formula of T/C (%) is: T/C (%)=$(T_{RTV}/C_{RTV}) \times 100\%$. $T_{RTV}$ is relative tumor volume of the treatment group, and $C_{RTV}$ is relative tumor volume of the negative control group. TGI (%)[b] tumor inhibition rate=(average tumor volume or weight of negative control group-average tumor volume or weight of administration group)/average tumor volume or weight of negative control group×100%. TGI (%)[a]=[(1−(average tumor volume of a certain administration group at the time of measurement-average tumor volume of the administration group at the beginning of the administration))/(average tumor volume of vehicle control group at the time of measurement-average tumor volume of the vehicle control group at the beginning of the administration)]×100%.

The assay results show that LGK974 and compounds of the present disclosure have an inhibitory effect on human pancreatic cancer Capan-2 xenograft tumor at a dose of 5 mg/Kg BID (twice a day) for 31 days. Data show that the effect of the compounds of the present disclosure is better than that of LGK974. The specific information is shown in Table 3 below:

TABLE 3

Anti-tumor efficacy of example compounds of the present disclosure in Capan-2 Xenograft model

| Compound | Dosage | TGI % | T/C % | P value |
|---|---|---|---|---|
| LGK974 | 5 mg/Kg, BID | 78.3 | 36.33 | <0.001 compared with vehicle group |
| Compound 1 | 5 mg/Kg, BID | 96.7 | 21.58 | <0.001 compared with vehicle group |
| Compound 11 | 5 mg/Kg, BID | 82.8 | 31.29 | <0.001 compared with vehicle group |
| Compound 30 | 2.5 mg/Kg, BID | 66.67 | 40.18 | <0.01 compared with vehicle group |
| Compound 30 (hydrochloride) | 5 mg/Kg, BID | 84.93 | 25.31 | <0.001 compared with vehicle group |
| Compound 33 | 5 mg/Kg, BID | 92.6 | 17.71 | <0.001 compared with vehicle group |
| Compound 36 (formate) | 5 mg/Kg, BID | 88.86 | 21 | <0.001 compared with vehicle group |

Assay 4: Pharmacokinetic Evaluation of Compounds

Assay purpose: Pharmacokinetics of compounds in Balb/c mice was assayed.

Assay Materials:

CD-1 mice (male, 7-9 weeks old, Shanghai Slack)

Assay Operation:

The pharmacokinetic characteristics of rodents after intravenous (IV) and oral (PO) administration of compounds were assayed by standard protocols. In the assay, mice were given a single intravenous injection and oral administration. The vehicle for intravenous injection was water. The oral vehicle was 0.5% hypromellose. Four male CD-1 mice were used in this project. Two mice were administered intravenously at a dose of 0.5 mg/kg, and plasma samples were collected at 0 h (before administration) and 0.083, 0.25, 0.5, 1, 2, 4, 8, and 24 h after administration. The other two mice were orally administered by gavage at a dose of 2.5 mg/kg, and plasma samples were collected at 0 h (before administration) and 0.25, 0.5, 1, 2, 4, 8, and 24 h after administration. Whole blood samples within 24 hours were collected, and centrifuged at 3000 g for 15 minutes. The supernatant was separated to obtain a plasma sample, and protein was precipitated by adding 4 times volume of acetonitrile solution containing internal standard. The mixture was centrifuged to obtain a supernatant, and an equal volume of water was added to the obtained supernatant. The mixture was then centrifuged to obtain a supernatant for injection. The blood drug concentration was quantitatively analyzed by LC-MS/MS analysis method, and pharmacokinetic parameters were calculated, such as peak concentration ($C_{max}$), clearance rate (CL), half-life ($T_{1/2}$), tissue distribution ($V_{dss}$), area under the drug-time curve ($AUC_{0\text{-}last}$), and bioavailability (F), etc.

The assay results are shown in Table 4: The compounds of the present disclosure have good pharmacokinetic properties.

TABLE 4

Pharmacokinetic evaluation results of the example compounds of the present disclosure in mice

| Compound | F (%) | $C_{max}$ (nM) | $T_{1/2}$ IV (hr) | Vdss (L/kg) | CL (mL/min/kg) | $AUC_{0\text{-}last}$ PO (nM · hr) |
|---|---|---|---|---|---|---|
| Compound 1 | 76.3 | 3027 | 2.23 | 0.633 | 5.05 | 16529 |
| Compound 22 | 71.9 | 1820 | 3.13 | 1.09 | 8.24 | 11949 |
| Compound 28 (hydrochloride) | 66.6 | 2340 | 2.6 | 0.553 | 4.16 | 15096 |
| Compound 29 (hydrochloride) | 89.0 | 2635 | 2.78 | 0.641 | 5.05 | 17300 |
| Compound 30 (hydrochloride) | 98.8 | 2580 | 2.5 | 0.666 | 5.75 | 16163 |
| Compound 33 | 37.4 | 107 | 3.69 | 9.52 | 35.1 | 975 |
| Compound 36 (formate) | 50.6 | 980 | 3.05 | 1.35 | 6.5 | 7226 |

What is claimed is:

1. A compound represented by formula (I), or a pharmaceutically acceptable salt thereof or isomer thereof,

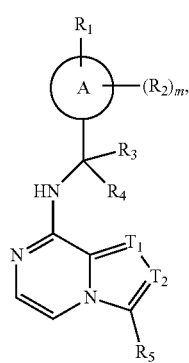

(I)

wherein:
$T_1$ and $T_2$ are each independently selected from CH or N;
ring A is 5- to 6-membered heteroaryl;

$R_1$ is pyrazolyl or 6-membered heteroaryl, wherein the pyrazolyl or 6-membered heteroaryl is optionally substituted with 1, 2 or 3 $R_a$;

each $R_a$ is independently selected from the group consisting of H, F, Cl, Br, I, CN, —OH, —OCH$_3$ and $C_{1-3}$ alkyl, wherein the $C_{1-3}$ alkyl is optionally substituted with 1, 2 or 3 substituents independently selected from the group consisting of F, Cl, Br, I, —OH and—CN;

each $R_2$ is independently selected from the group consisting of H, F, Cl, Br, I, CN, —OH,

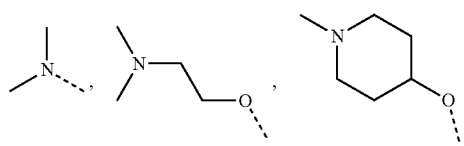

and $C_{1-3}$ alkyl, wherein the $C_{1-3}$ alkyl is optionally substituted with 1, 2 or 3 substituents independently selected from the group consisting of F, Cl, Br, I, —OH and—CN;

$R_3$ and $R_4$ are each independently H or $C_{1-3}$ alkyl, wherein the $C_{1-3}$ alkyl is optionally substituted with 1 or 2 substituents independently selected from the group consisting of F, Cl, Br, I and—OH;

$R_5$ is phenyl, wherein the phenyl is optionally substituted with 1, 2 or 3 $R_d$;

each $R_d$ is independently selected from the group consisting of H, F, Cl, Br, I, CN, —C(=O)—$C_{1-3}$ alkyl, $C_{1-3}$ alkyl and $C_{1-3}$ alkoxy, wherein the $C_{1-3}$ alkyl and $C_{1-3}$ alkoxy are optionally substituted with 1, 2 or 3 substituents independently selected from the group consisting of F, Cl, Br, I, —OH and—CN;

m is 0, 1, 2 or 3; and the 5- to 6-membered heteroaryl contains 1, 2, 3 or 4 heteroatoms independently selected from the group consisting of N, —O-and-S—.

2. The compound, pharmaceutically acceptable salt thereof or isomer thereof according to claim 1, wherein the compound has a structure as shown in formula (I-1) or (I-2):

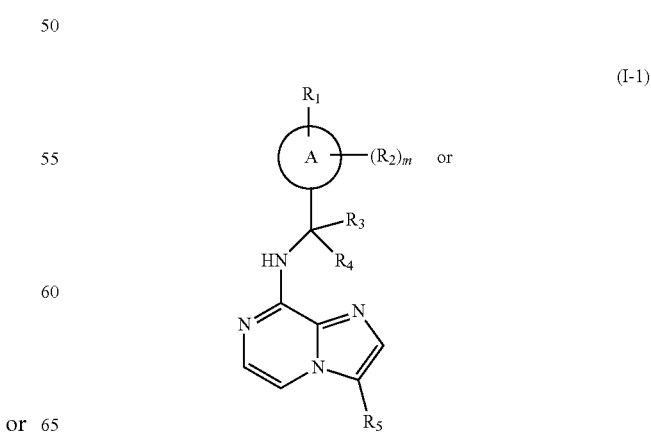

(I-1)

-continued (I-2)

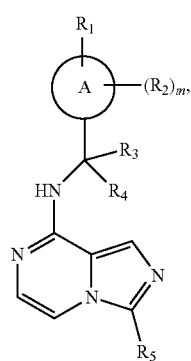

wherein ring A, $R_1$, $R_2$, $R_3$, $R_4$, $R_5$ and m are as defined in claim 1.

3. The compound, pharmaceutically acceptable salt thereof or isomer thereof according to claim 1, wherein $T_1$ is N, and $T_2$ is CH.

4. The compound, pharmaceutically acceptable salt thereof or isomer thereof according to claim 1, wherein ring A is pyridyl.

5. The compound, pharmaceutically acceptable salt thereof or isomer thereof according to claim 4, wherein the moiety

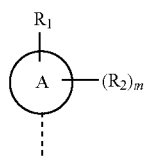

is; or wherein the moiety

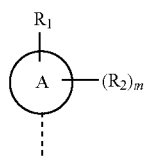

is; or wherein the moiety

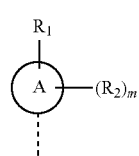

is

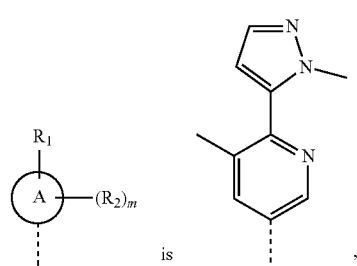

,

-continued

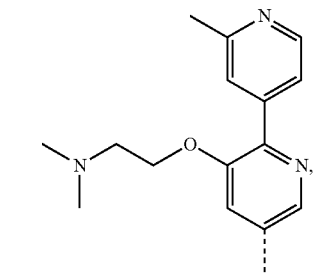

,

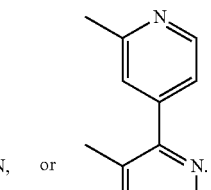

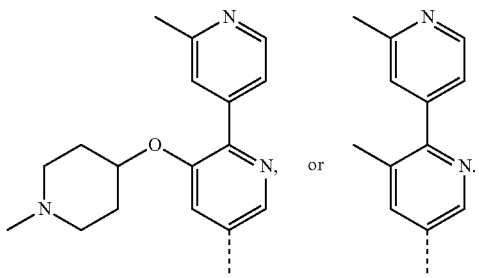

6. The compound, pharmaceutically acceptable salt thereof or isomer thereof according to claim 1, wherein the compound has a structure as shown in formula (I-3) or (I-4):

(I-3)

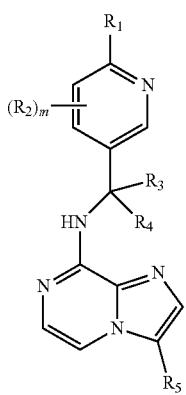

or (I-4)

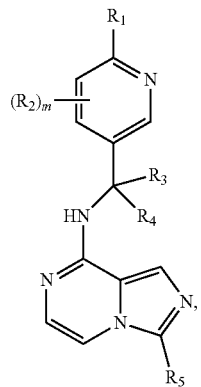

wherein $R_1$, $R_2$, $R_3$, $R_4$, $R_5$ and m are as defined in claim 1.

7. The compound, pharmaceutically acceptable salt thereof or isomer thereof according to claim 1, wherein $R_1$ is pyrazolyl or pyridyl, wherein the pyrazolyl and pyridyl are optionally substituted with 1, 2 or 3 $R_a$; or $R_1$ is

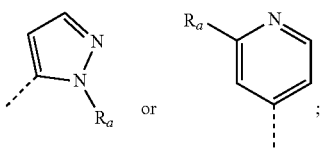

or $R_1$ is

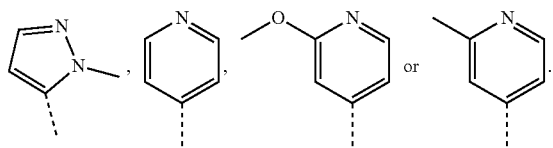

8. The compound, pharmaceutically acceptable salt thereof or isomer thereof according to claim 1, wherein the compound has a structure as shown in formula (I-5), (II-2), or (I-6):

(I-5)

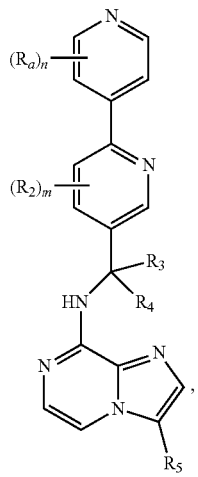

(II-2)

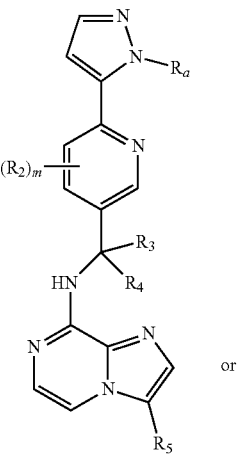

or

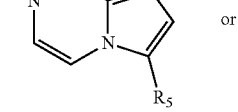

(I-6)

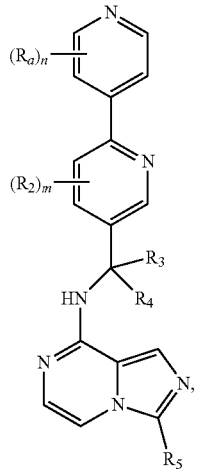

wherein $R_2$, $R_3$, $R_4$, $R_5$, m and each $R_a$ are as defined in claim 1, and n is 1 or 2.

9. The compound, pharmaceutically acceptable salt thereof or isomer thereof according to claim 1, wherein R₅ is selected from the group consisting of

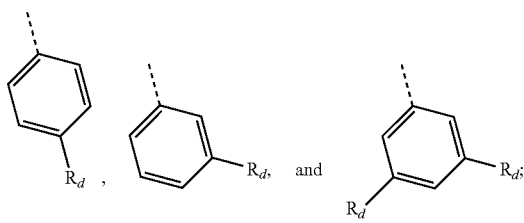

wherein R₅ is selected from the group consisting of

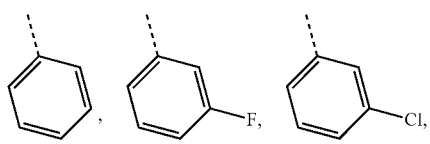

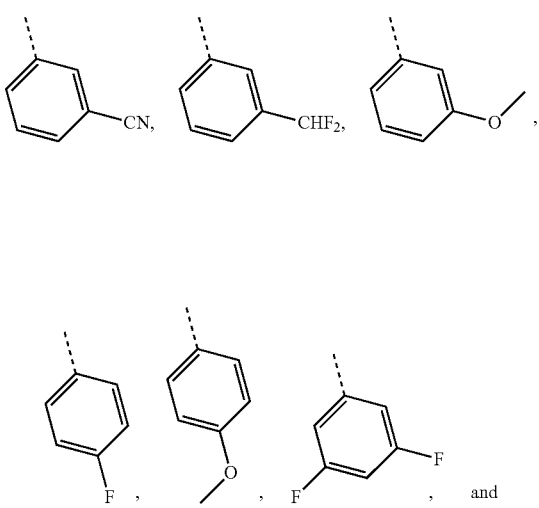

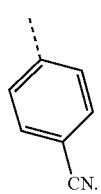

10. The compound, pharmaceutically acceptable salt thereof or isomer thereof according to claim 1, wherein the compound has a structure as shown in formula (I-7) or (I-13):

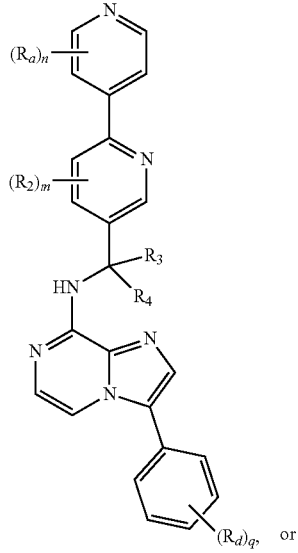

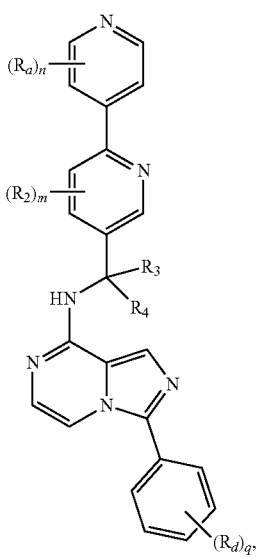

wherein R₂, R₃, R₄, m, n, $R_a$ and $R_a$ are as defined in claim 1, and q is 1 or 2.

11. The compound, pharmaceutically acceptable salt thereof or isomer thereof according to claim 1, wherein each R₂ is independently selected from the group consisting of H, F, Cl, Br, I, CN,

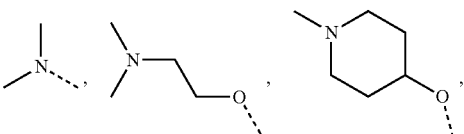

—CH₃, —CH₂CH₃ and —CF₃.

12. The compound, pharmaceutically acceptable salt thereof or isomer thereof according to claim 1, wherein R₃ and R₄ are each independently —H, —CH₃ or —CH₂OH.

13. A compound of the formula below, pharmaceutically acceptable salt thereof or isomer thereof:

1
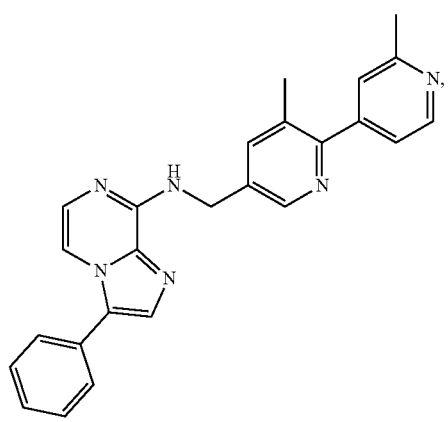
3
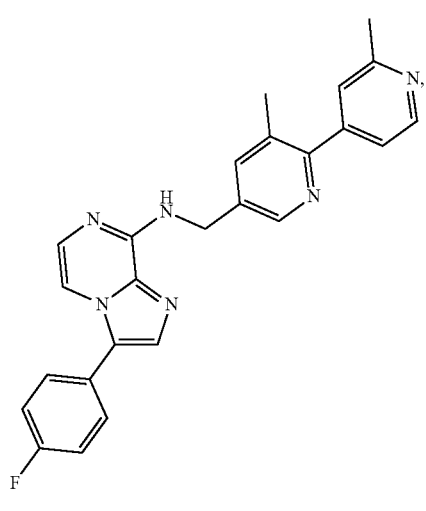
8
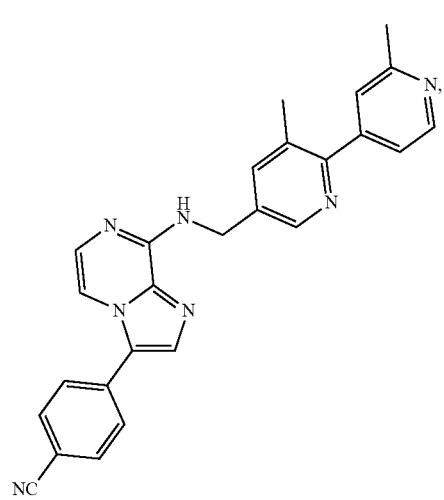
-continued
9
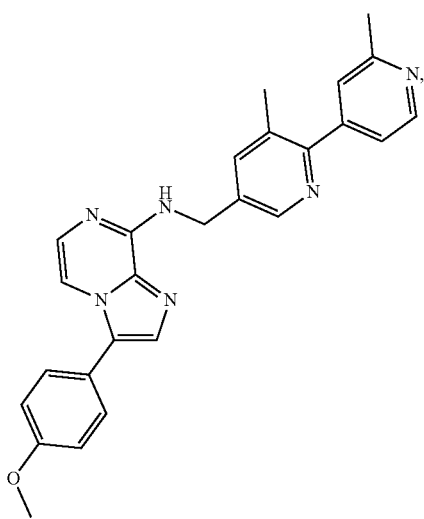
11
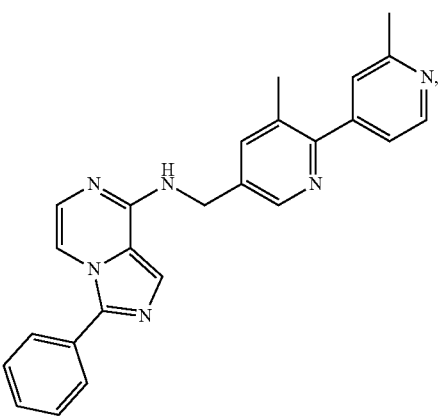
18
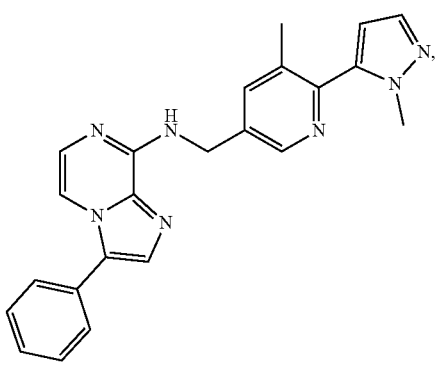

19
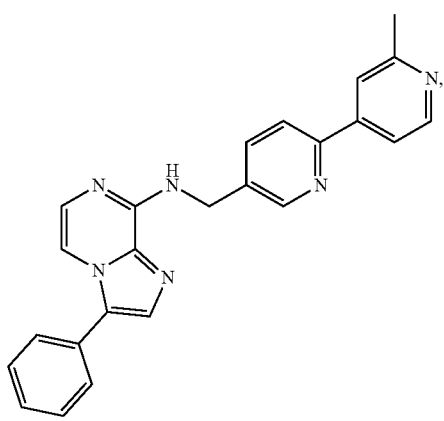
20
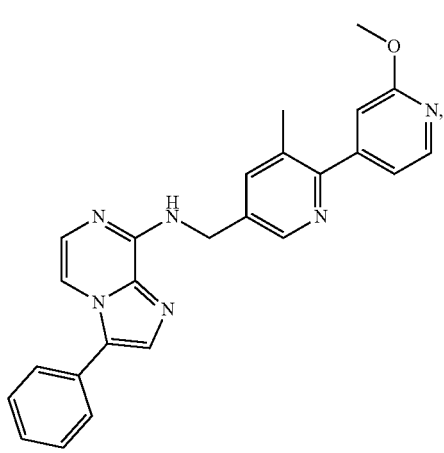
21
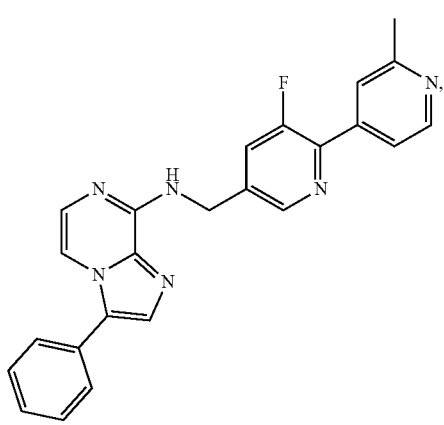
25
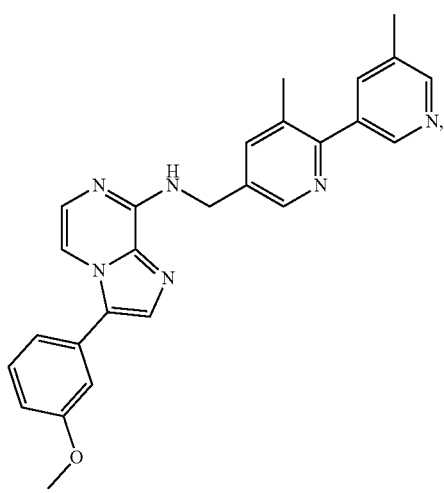
26
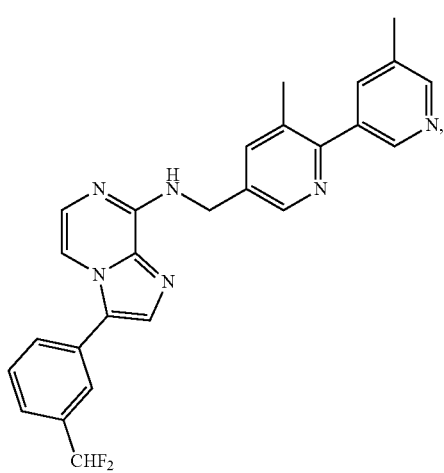
27

28
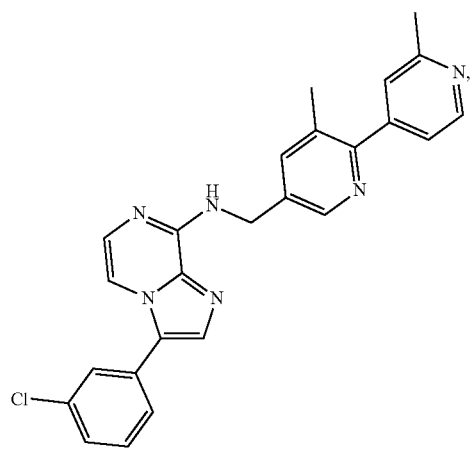
29
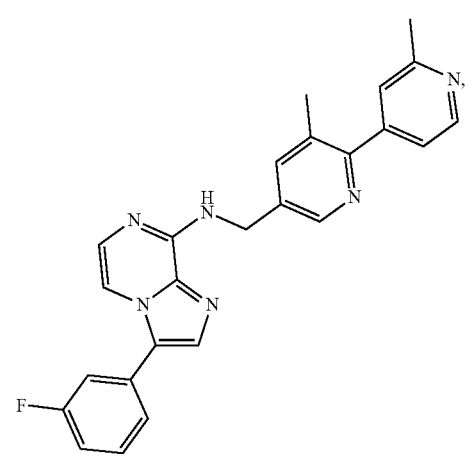
30
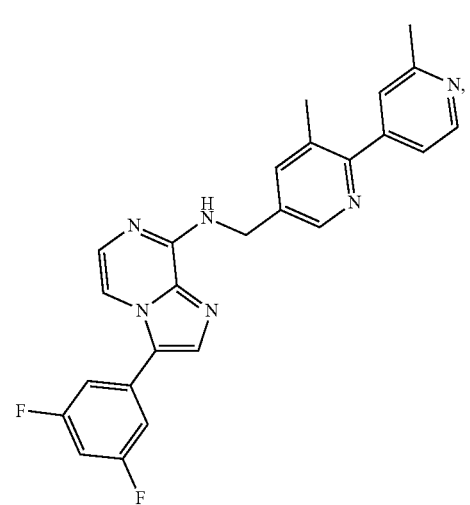
32
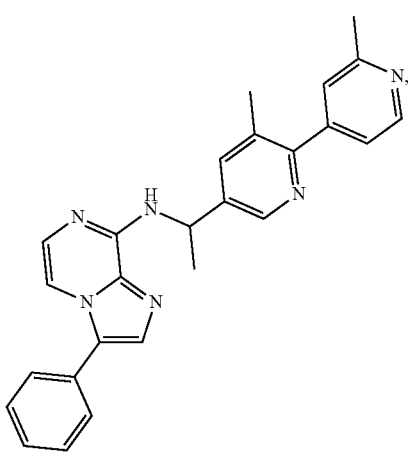
33
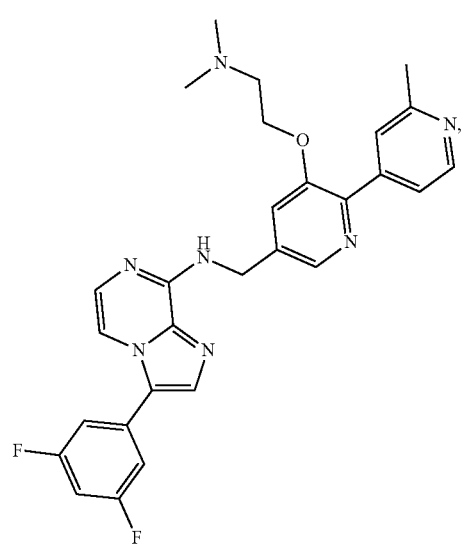

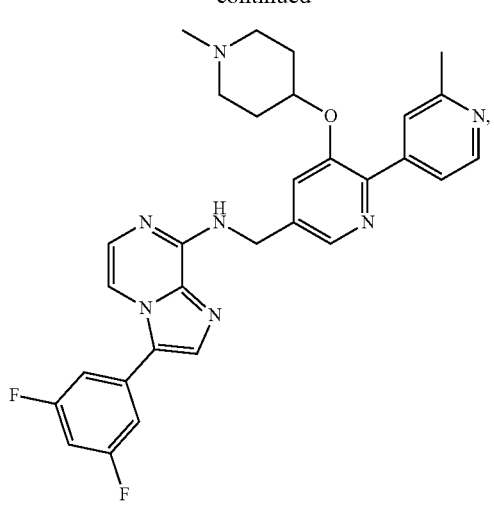

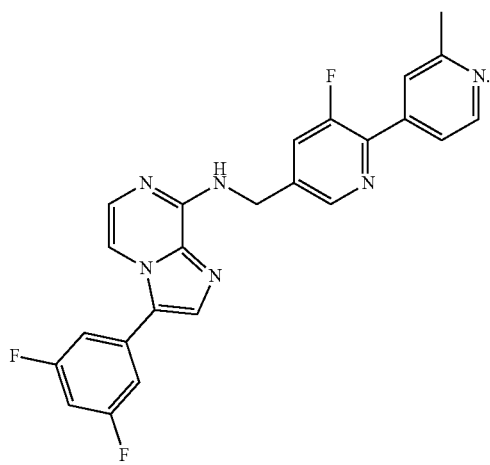

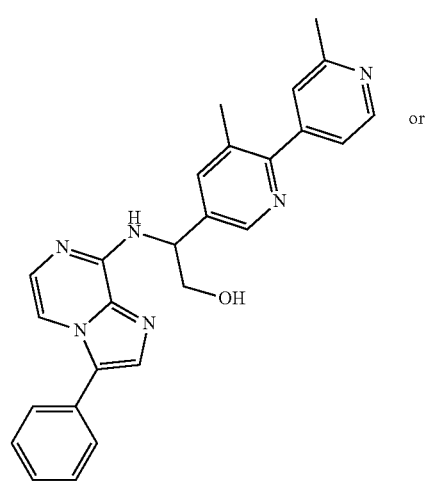

or

14. A pharmaceutical composition containing a therapeutically effective amount of the compound, pharmaceutically acceptable salt thereof or isomer thereof according to claim 1, and pharmaceutically acceptable carrier (s).

15. A method of treating a disease related to porcupine protein in a subject in need thereof, comprising administering to the subject the compound, pharmaceutically acceptable salt thereof or isomer thereof according to claim 1.

16. A method of treating a pancreatic cancer in a subject in need thereof, comprising administering to the subject the compound, pharmaceutically acceptable salt thereof or isomer thereof according to claim 1.

* * * * *